US012324295B2

(12) United States Patent
Harthcock

(10) Patent No.: US 12,324,295 B2
(45) Date of Patent: Jun. 3, 2025

(54) COMPLEX NANOSTRUCTURE FORMING A BIDIRECTIONAL NANOSTRUCTURE MULTIPLEXER OR ARTIFICIAL NEURON

(71) Applicant: Jerry D. Harthcock, Boerne, TX (US)

(72) Inventor: Jerry D. Harthcock, Boerne, TX (US)

( * ) Notice: Subject to any disclaimer, the term of this patent is extended or adjusted under 35 U.S.C. 154(b) by 993 days.

(21) Appl. No.: 17/350,805

(22) Filed: Jun. 17, 2021

(65) Prior Publication Data

US 2022/0376193 A1    Nov. 24, 2022

Related U.S. Application Data

(60) Provisional application No. 63/053,907, filed on Jul. 20, 2020.

(51) Int. Cl.
| | |
|---|---|
| B32B 9/00 | (2006.01) |
| H10K 10/00 | (2023.01) |
| H10K 85/00 | (2023.01) |
| H10K 85/20 | (2023.01) |
| B82Y 5/00 | (2011.01) |
| B82Y 30/00 | (2011.01) |
| B82Y 40/00 | (2011.01) |

(52) U.S. Cl.
CPC ........... H10K 10/00 (2023.02); H10K 85/221 (2023.02); H10K 85/761 (2023.02); *B82Y 5/00* (2013.01); *B82Y 30/00* (2013.01); *B82Y 40/00* (2013.01)

(58) Field of Classification Search
CPC .... Y10T 428/30; H10K 10/00; H10K 85/761; H10K 85/221; B82Y 5/00
USPC ....................................................... 428/408
See application file for complete search history.

(56) References Cited

FOREIGN PATENT DOCUMENTS

CN         102911912 A    *   2/2013

OTHER PUBLICATIONS

G.S. Paraoanu, "The quantum vacuum," 2014, Aalto University, Aalto, Finland.
O. Tapia, "Photonic Framework: Cues To Decode Quantum Mechanics," Uppsala University, Sweden.
Chang-Hua, et al., "A Fully Tunable Single-Walled Carbon Nanotube Diode," Nano Lett. 2011, 11, 1782-1785, ACS Publications, Washington, DC.

(Continued)

*Primary Examiner* — Daniel H Miller
(74) *Attorney, Agent, or Firm* — Steven W. Smith

(57) ABSTRACT

A complex nanostructure, which includes a first nanostructure component having at least one aperture in a side thereof; at least one second nanostructure component having a first end and a second end, wherein the first end of each of the at least one second nanostructure is inserted through a corresponding one of the at least one aperture in the first nanostructure, thereby forming at least one junction. Embodiments of the complex nanostructure include a bifurcated nanostructure transistor constructed of linear carbon nanotubes, a multiplexer constructed of a circular carbon nanotube and multiple linear carbon nanotubes, and an information unfolder constructed of linear or a combination of linear and circular carbon nanotubes. The nanotubes may optionally be decorated with genetic material such as single-strand or double-strand human DNA segments and/or may be modified by e-beam or ozone gas to add defects into the nanotubes to alter electrical/functional characteristics.

21 Claims, 54 Drawing Sheets

(56) References Cited

OTHER PUBLICATIONS

Cees Dekker, et al., "Electronic properties of DNA." Physicsworld, 2001, Bristol, UK.
Jerry D. Harthcock, "HedgeHog Fused Spiking Neural Network Emulator/Compute Engine," v1.02, 2020, Boerne, Texas.
Huajian Gao et al., "Simulation of DNA-Nanotube Interactions," Annual Reviews, 2004, Stuttgart, Germany.
Ken-ichi Sasaki, et al., "Characteristic Behavior of Toroidal Carbon Nanotubes," 2004, Institute for Materials Research, Sendai, Japan.
Lingjie Meng et al., "Advanced technology for functionalization of carbon nanotubes," Progress in Natural Science 19 (2009) 801-810.
Masahiro Nakajima et al., "Nanomanipulation and Nanoassembly of Carbon Nanotubes Inside Electron Microscopes," International Federation of Automatic Control, Seoul, Korea.
"Scientists make silver nanowires based on DNA molecules," Physics.org, 2016.
Prabhakar R. Bandaru, "Carbon Nanotube Y-Junctions," University of California, San Diego, California.
Ahi Chen, "Nanotubes for Nanoelectronics," 2004, University of Kentucky, Lexington, Kentucky.

* cited by examiner

COMPLEX NANOSTRUCTURE FORMING A BIDIRECTIONAL NANOSTRUCTURE MULTIPLEXER OR ARTIFICIAL NEURON

CROSS-REFERENCE TO RELATED APPLICATIONS

This application claims the priority benefit under 35 U.S.C. § 119(e) of U.S. Provisional Application No. 63/053,907 filed on Jul. 20, 2020, the disclosure of which is incorporated herein by reference in its entirety.

TECHNICAL FIELD

The present disclosure relates generally to nanostructures, and more particularly to a complex nanostructure constructed from carbon nanotubes and variously configured to function as a bifurcated nanostructure transistor, a nanostructure multiplexer, or an information unfolder.

BACKGROUND

From research done several decades ago up until the present by both private and government agencies primarily of the United States, Russia/USSR, China, and Japan, it has been established beyond any doubt that there exists a bidirectional psychotronic/psychoenergetic (these terms used interchangeably throughout the present disclosure) channel of communication. To demonstrate this fact, volumes of declassified, once secret and highly guarded research and corresponding documents relating to the United States Defense Intelligence Agency involvement in weaponizing (and defending against) this "phenomenon" can be located and freely downloaded at the public CIA.gov library reading room website using search terms such as, "Star Gate," "Grill Flame," "Center Lane," "psychoenergetics," "psychotronic," "remote viewing," "remote action," "SRI International," "Hal Puthoff," and "Ingo Swann," for example.

Chief among them is an article by respected physicists Dr. Hal Puthoff and Dr. Russell Targ published in the prestigious and peer-reviewed *Proceedings of the IEEE* (March 1976) journal entitled, "A Perceptual channel for information transfer over kilometer distances: Historical perspective and recent research."

Another article by Puthoff published in the prestigious *Journal of Scientific Exploration* (vol. 10, 1976) entitled, "CIA-Initiated Remote Viewing Program at Stanford Research Institute," can be found in the public online CIA.gov reading room.

Several declassified documents found online at the CIA.gov reading room website describe psychoenergetics as certain classes of human capabilities in the realm of parasychological or PSI phenomenon, further breaking it down into two general informational and energetic categories:

1. Remote viewing (RV)/Extrasensory Perception (ESP)—the ability to describe remote geographical areas or to describe concealed data via undefined transmission mechanisms.

2. Psychokinesis (PK)—the mental ability to influence physical or biological systems without use of known physical mechanisms.

Research has also been performed by quantum physicists on what is referred to as the "vacuum state" and information transfer within the vacuum state. Paraoanu, G. S., "The quantum vacuum," O. V. Lounasmaa Laboratory, School of Science, Aalto University, Finland, first provides a brief history of the vacuum up to the quantum era beginning with Greek atomists Leucippus and Democritus, all the way up to Einstein. Paraoanu then delves into the architecture of the vacuum discussing, among others, such topics as the observable effects, and their properties, due to the quantum vacuum, concluding by noting the fact that energy itself cannot be teleported within the quantum vacuum, but rather, the "information" about such energy is teleported. When a measurement is made, only then does it manifest as energy at the destination, and this has been called "quantum energy teleportation."

Paraoanu may explain the phenomenon called psychoenergetics, in that what may be happening is that "information" is what is really being psychoenergetically transferred, and when the target perceives the information (measures it) by whatever means, only then does the teleported information manifest as a physical "energetic." Paraoanu is hereby incorporated herein in its entirety.

Tapia, O., "Photonic Framework: Cues To Decode Quantum Mechanics," Chemistry Ångström, Uppsala University, Sweden, discusses photons, electrons, and other subatomic particles, especially as they relate to information transfer within a vacuum, e.g., the interior of carbon nanotubes. Tapia describes Quantum Electro Dynamics (QED), quantum entanglement, and information transfer at the quantum level. Tapia states that "vacuum states carry endless information" and "entanglement events integrate probing devices leading to q measurements seen as physical processes." This establishes further that electrons are subatomic particles and consequently are subject to entanglement and they supplement detection devices. Information is the "stuff" conveyed by quantum processes and "vacuum state information enters as labels re-normalizing the base set." Tapia is hereby incorporated herein in its entirety.

While it has been scientifically established beyond any doubt that there exists a psychoenergetic channel of information transfer, up until now, there has been no known repeatable means or method for a machine to reliably extract and exploit desired information from this vacuum state information channel. Some of the methods for "remote action" developed by researchers with modest success include remote mental perturbation of EEGs, true random number generators, piezo-electric sensors, and thermistors to name a few. However, one problem with all of these approaches is that none of them have direct access to the vacuum state, where all the information in the universe, past, present and future can be accessed. Another problem with these approaches is that, even if, arguendo, those methods could access the vacuum state where all the information is folded up into the tiniest bit of nothing, such methods have no way of unfolding this vacuum state information and thereby make use of it.

The present disclosure describes such an apparatus and method for not only accessing the folded up information from the vacuum state, but also unfolding such information and making use of it. The disclosure employs specially modified carbon nanotubes and carbon nanotori arranged and assembled on a special SiO2 substrate using an assembly jig etched into it to exploit this psychotronic channel of communication by way of a quantum information extractor or, more precisely, vacuum state information "unfolder" and thus can also be employed as a type of quantum computer with the potential to deliver information (in human readable form if necessary) directly to its outputs without intervening computations. The present disclosure can also be configured to provide data to a conventional convolutional or recurrent artificial neural network and/or spiking artificial neural network, which with proper training algorithm, can be employed to implement systems based on conscious computers and machines.

SUMMARY

The present invention is a complex nanostructure, which includes a first nanostructure component having at least one aperture in a side thereof; at least one second nanostructure component having a first end and a second end, wherein the first end of each of the at least one second nanostructure is inserted through a corresponding one of the at least one aperture in the first nanostructure, thereby forming at least one junction; and means for causing current to flow selectively through the first nanostructure or the at least one second nanostructure. For example, optional fields may enable current flow.

In one embodiment, the complex nanostructure is a bifurcated nanostructure transistor. In this embodiment, the first nanostructure component is a first linear carbon nanotube forming a nanostructure trunk having a first end, a second end, and the aperture in a side thereof. The at least one second nanostructure component is a second linear carbon nanotube forming a nanostructure L, wherein the first end of the nanostructure L is inserted through the side of the nanostructure trunk via the aperture, thereby forming a junction, and the nanostructure L is angled away from the first end of the nanostructure trunk. The bifurcated nanostructure transistor also includes a first electrical contact at the first end of the nanostructure trunk; a second electrical contact at the second end of the nanostructure trunk; and a third electrical contact at the second end of the nanostructure L. Whenever a voltage potential across two or more of the first, second, and third electrical contacts is present, current flows selectively from any of the electrical contacts having greater potential to any of the contacts having lesser potential, thereby providing a transistor effect.

Either or both nanotubes may optionally be decorated with genetic material such as single-strand or double-strand human DNA segments (especially that of a percipient donor) and/or may be modified by e-beam or ozone gas to add defects into the nanotubes to alter electrical/functional characteristics of the resulting transistor.

The bifurcated carbon nanotube transistor may be specially constructed using a substrate prefabricated with an assembly jig etched into it using either chemical etch or Focused Ion Beam (FIB), for example. During the assembly process, the first carbon nanotube may be positioned into a respective jig trench using, for example, an Atomic Force Microscope (AFM) or by using an AC dielectrophoresis (DEP) method. The first carbon nanotube, hereinafter referred to as the "trunk," is slightly wider in diameter than the second carbon nanotube, hereinafter referred to as the "L."

In the example 3D models provided in the present disclosure [6,6] metallic carbon nanotubes are employed as the trunk and [6,0] semiconducting carbon nanotubes are employed as the "L", which is described in greater detail below. With a [6,6] chirality, the metallic carbon nanotubes in the exemplary 3D models have a diameter of roughly 2.45 nanometers, while the [6,0] semiconducting carbon nanotubes have a diameter of roughly 1.5 nanometers.

Once the trunk is in position, an e-beam may be employed to burn an orifice/incision in the trunk's side large enough to accept one end of the "L" at approximately a 30-degree angle from perpendicular away from the input end of the trunk. Once joined in this manner, the result is a bifurcated carbon nanotube transistor that can be steered psychotronically using only the volition of a percipient directed at it.

In another embodiment, the complex nanostructure includes a circular carbon nanotorus made from a first carbon nanotube formed into a circle, the first carbon nanotube having a plurality of apertures in a side thereof facing radially outward from a center of the nanotorus. The nanostructure also includes a plurality of linear carbon nanotubes having first and second ends and a diameter smaller than a diameter of the first carbon nanotube, wherein the first end of each of the plurality of linear carbon nanotubes is inserted through one of the apertures in the first carbon nanotube, thereby forming a plurality of junctions. One of the plurality of linear carbon nanotubes is configured as an axion of a nanostructure multiplexer while the remaining linear carbon nanotubes are configured as dendrites of the nanostructure multiplexer. The multiplexer may also function as an information channel selector.

Like the bifurcated nanostructure transistor above, the multiplexer/information channel selector may be constructed using a substrate prefabricated with an assembly jig etched into it. The assembly jig resembles a bicycle hub with spokes coming out of it at a 30-degree angle from perpendicular. The nanotorus aspect, hereinafter referred to as the psyclotron, of the multiplexer is slightly wider in diameter than the "L" carbon nanotubes that are inserted into its sides at 30-degree angles, forming the dendrites and axion of the artificial neuron/multiplexer, the psyclotron.

The nanotorus for the psychlotron may be placed into position using an AFM or DEP so that it drops into its circular seat etched into the substrate. Once in position, an e-beam may be used to incise the outer sidewall of the psychlotron at each intersection where each "L" will be inserted using either an AFM or DEP method.

The psyclotron and/or nanotubes may optionally be decorated with genetic material such as single-strand or double-strand human DNA segments (especially that of a percipient donar) and/or may be modified by e-beam or ozone gas to add defects into the tubes to alter electrical/functional characteristics of the resulting multiplexer/information channel selector. The multiplexer/information channel selector may function as an artificial neuron.

In another embodiment the complex nanostructure is configured to unfold information carried by electrons. The complex nanostructure information unfolder includes an array of carbon nanotubes joined at points to form binary junctions within the array, the array having an input connection and a plurality of output connections; and a plurality of electron-detection spiker circuits connected to the plurality of output connections. Whenever a voltage potential is present across the array, electrons flow through the plurality of carbon nanotubes and at each junction, make a binary choice of which route to follow in order to arrive at a given electron-detection spiker circuit. A distribution of arriving electrons across the plurality of electron-detection spiker circuits is indicative of information carried by the electrons.

In one embodiment of the information unfolder, the array of carbon nanotubes includes one or more bifurcated carbon nanotube transistors connected to each dendrite "L" of the multiplexer described above. The outputs of the bifurcated carbon nanotube transistors go to a "spiker" circuit that generates a spike on its output when the charge coming in reaches a pre-programmed upper trigger point threshold. In parallel with each spike generator is a "spert" circuit that generates a single-clock pulse on its output when the charge coming in reaches a per-programmed lower trigger point threshold, which is less than the upper trigger point threshold of a "spike" trigger point.

The main purpose of the spert circuit is to provide an indicator for those outputs that do not reach the upper trigger point (but otherwise did reach the lower spert trigger point) as to whether they were deprived of energy, indicating that energy was somehow taken away and instead used to trigger a spike in a different spiker circuit. Stated another way, in a dead universe, none of the outputs should ever spike because they are never psychotronically perturbed into reaching the spike firing threshold, in that, in its quiescent, unperturbed state, there is only so much current entering the system over a given period of time, such that, in a dead universe (i.e., not perturbation arising out of a conscious volition), the current is evenly distributed among all the spiking circuits, in that the only way to produce a spike on a given output is for current to somehow be deliberately diverted to that or other particular spiking circuits. The spert circuit lower trigger point is set so that in a dead universe it will always (or at least almost always) produce a spert on its output during each synchronized frame period. If a spert does not happen during a particular synchronized frame, especially when a spike was generated on a different spiker output, this is an indicator that that particular spert circuit was deprived of energy during that cycle.

In another embodiment of the information unfolder, the array of carbon nanotubes includes a plurality of bifurcated nanostructure transistors configured in a plurality of rows. Each of the bifurcated nanostructure transistors includes a carbon nanotube trunk having a first end, a second end, and an aperture in a side thereof; and a carbon nanotube L having a first end and a second end, wherein the first end of the carbon nanotube L is inserted through the side of the carbon nanotube trunk via the aperture, thereby forming a junction, and the carbon nanotube L is angled away from the first end of the carbon nanotube trunk. The bifurcated nanostructure transistors also include an electrical input contact at the first end of the carbon nanotube trunk; a first electrical output contact at the second end of the carbon nanotube trunk; and a second electrical output contact at the second end of the carbon nanotube L.

A first row of the array includes a single bifurcated nanostructure transistor, and the electrical input contact of the single bifurcated nanostructure transistor provides an input for the entire array. Succeeding rows of the array include twice as many bifurcated nanostructure transistors as a preceding row, and the first and second electrical output contacts of each transistor in the preceding row are electrically connected to the electrical input contact of first and second transistors in the succeeding row. A last row of the array includes a plurality of bifurcated nanostructure transistors, and the first and second electrical output contacts of each transistor in the last row are electrically connected to corresponding electron-detection spiker circuits of the plurality of electron-detection spiker circuits. Whenever the voltage potential is present across the array, electrons flow through the plurality of bifurcated nanostructure transistors making binary choices of which route to follow at each junction of each transistor in order to arrive at a given electron-detection spiker circuit. Each spiker circuit of the plurality of electron-detection spiker circuits generates a spike on an output when a charge arriving from a respective bifurcated nanostructure transistor reaches a pre-programmed upper trigger-point threshold, thereby indicating a distribution of arriving electrons across the plurality of electron-detection spiker circuits, the distribution being indicative of information carried by the electrons.

The spike train produced by the information unfolder may be fed into the input of an artificial spiking neural network for further processing, the network being part of a information processing system run on a computer. Alternatively, the analog output of each instrumentation amplifier inside each spiker and spert circuit may be brought out and quantized with an analog-to-digital (A/D) converter and fed into a conventional convolutional or recurrent artificial neural network in lieu of a spiking neural network. For purposes of the instant disclosure, these two variations are herein referred to interchangeably as electron-detection spiker circuits.

Further features and benefits of embodiments of the disclosed apparatus will become apparent from the detailed description below.

BRIEF DESCRIPTION OF THE DRAWINGS

In the following section, the invention will be described with reference to exemplary embodiments illustrated in the figures, in which:

FIG. 13l is similar to FIG. 1, except it is showing single-stranded DNA alone being employed as the "L", the ssDNA optionally being impregnated with silver and/or nickel nanoparticles;

DETAILED DESCRIPTION

The present disclosure will now be described more fully hereinafter with reference to the accompanying drawings, in which preferred embodiments of the disclosure are shown. In the below, for purposes of explanation and not limitation, specific details are set forth in order to provide a thorough understanding of the present disclosure. It will be apparent to one skilled in the art that the present disclosure may be practiced in other embodiments that depart from these specific details.

Figure 1A:
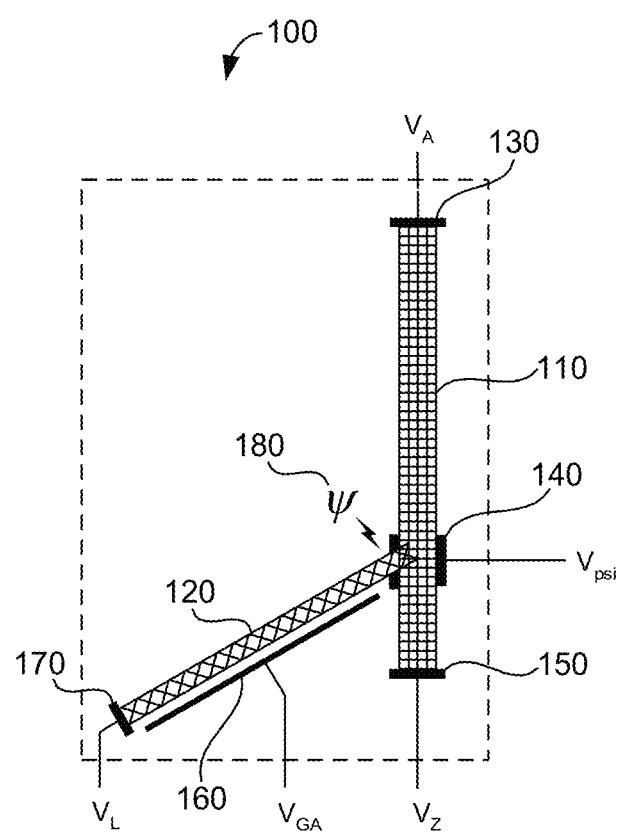
FIG. 1a is a diagram of a psychotronically-steerable, bifurcated "L-field" conscious-gate transistor built from two carbon nanotubes, having a metallic "trunk" and a semiconducting "L"

FIG. 1a is a diagram of the disclosed embodiment of the psychotronically-steerable, bifurcated "L-field" conscious-gate transistor built from two carbon nanotubes, having a metallic "trunk" and a semiconducting "L". The psychotronically steerable, bifurcated carbon nanotube (CNT) transistor 100 includes a carbon nanotube trunk 110, carbon nanotube "L" 120, an electrical contact 130 for the $V_A$ end of the trunk, an electrical contact 150 for the $V_Z$ end of the trunk, an electrical contact 170 for the $V_L$ end of the "L," a field 160 for the "L", and an optional electrical contact 140 for the trunk/"L" junction 180 having a canted aspect ratio that facilitates vacuum state information transfer. In the disclosed exemplary embodiment, the trunk of FIG. 1a is metallic and the "L" is semiconducting. The trunk of FIG. 1a does not require a gate to conduct current because it is metallic. Since the "L" of FIG. 1a is semiconducting, a charge with field strength sufficient enough to allow current to flow must be present at 160, otherwise, current will not flow through the "L."

As can be seen from FIG. 1a, when a voltage potential is applied across electrical contacts 130, 150, and 170 such that contact 130 is at a higher potential than contacts 150 and 170, current flow has to choose between contacts 170 and 150 in terms of which path to take (and by how much for each path) to complete the circuit. Assuming it is the volition of a percipient directed at the vacuum state information unfolder and perhaps any percipient ssDNA that decorates 100, that, in essence, makes that choice for the current that passes through 100. Stated another way, because of the percipient's volition, the current really has no choice, in that it already knows what path to take before it ever reaches junction 180. An analogy here would be the human body where a person manifests the volition to raise his left arm. How do the electrons that cause the proteins constituting his muscles to contract or expand know which path to take? Why does the person's right arm or leg not raise instead? The simple answer is that certain "instructions" or "information" is imposed on those electrons, possibly via DNA or RNA, while in flight. Those electrons already know, long before they arrive, not only where to go, but also how to get there.

Figure 1B:
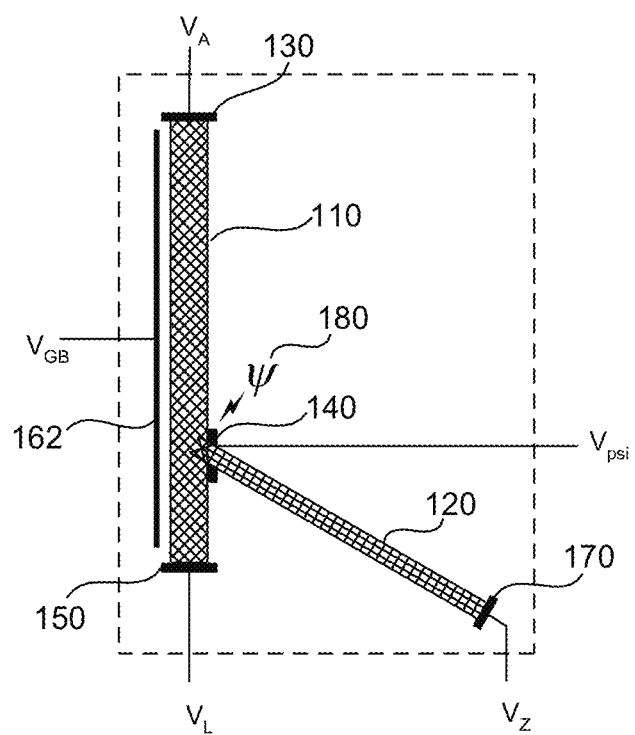
FIG. 1b is a diagram of a psychotronically-steerable, bifurcated "trunk-field" conscious-gate transistor built from two carbon nanotubes, having a semiconducting "trunk" and a metallic "L"

FIG. 1b is a diagram of a psychotronically-steerable, bifurcated "trunk-field" conscious-gate transistor built from two carbon nanotubes, having a semiconducting "trunk" and a metallic "L". FIG. 1b is similar to FIG. 1a, except the trunk of FIG. 1b is semiconducting and the "L" is metallic. Since the trunk is semiconducting, it requires a field 162.

Figure 1C:
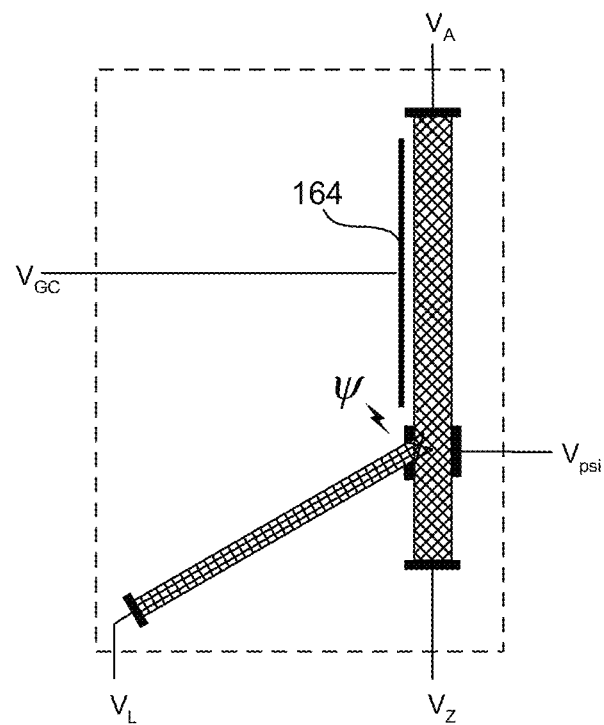
FIG. 1c is a diagram of a psychotronically-steerable, bifurcated "partial trunk-field" conscious-gate Field-Effect Transistor built from two carbon nanotubes, having a semiconducting "trunk" and a metallic "L"

FIG. 1c is a diagram of a psychotronically-steerable, bifurcated "partial trunk-field" conscious-gate Field-Effect Transistor built from two carbon nanotubes, having a semiconducting "trunk" and a metallic "L". FIG. 1c is similar to FIG. 1b, except its field 164 does not extend past the junction 180 of FIG. 1b.

Figure 1D:
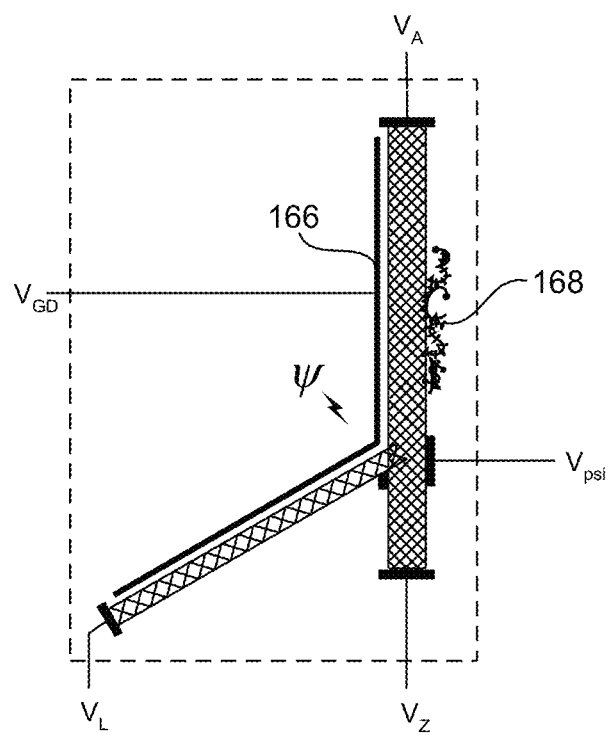
FIG. 1d is a diagram of a psychotronically-steerable, bifurcated "partial trunk/L-field" conscious-gate transistor built from two carbon nanotubes, having a semiconducting "trunk", a semiconducting "L", and optional DNA decoration, single or double-stranded.

FIG. 1d is a diagram of a psychotronically-steerable, bifurcated "partial trunk/L-field" conscious-gate transistor built from two carbon nanotubes, having a semiconducting "trunk" and "L", and optional DNA decoration, single or double-stranded. FIG. 1d is similar to FIG. 1a, except the trunk and "L" are both semiconducting and share the same field 166, in addition to the CNT transistor 100 being optionally decorated with dsDNA or ssDNA 168.

Figure 1E:
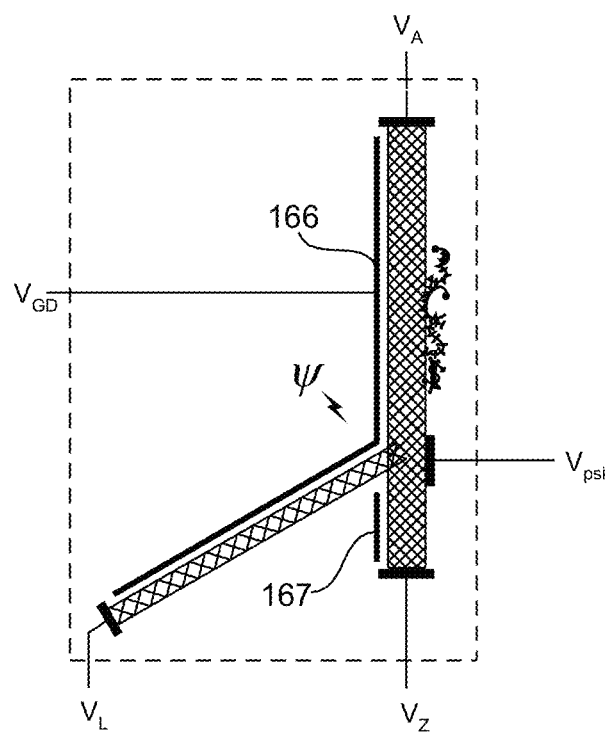
FIG. 1e is a diagram of a psychotronically-steerable, bifurcated "full trunk/L-field" conscious-gate transistor built from two carbon nanotubes, having a semiconducting "trunk", a semiconducting "L", and optional DNA segment, single or double-stranded.

FIG. 1e is a diagram of a psychotronically-steerable, bifurcated "full trunk/L-field" conscious-gate transistor built from two carbon nanotubes, having a semiconducting "trunk" and "L", and optional DNA segment, single or double-stranded. FIG. 1e is similar to FIG. 1d, except the entire trunk and entire "L" share the same field. Alternatively, field section 167 can be split from field 166 so that different potentials can be applied to them so as to essentially cause the trunk portion to behave similarly to a P-N junction diode.

Figure 1F:
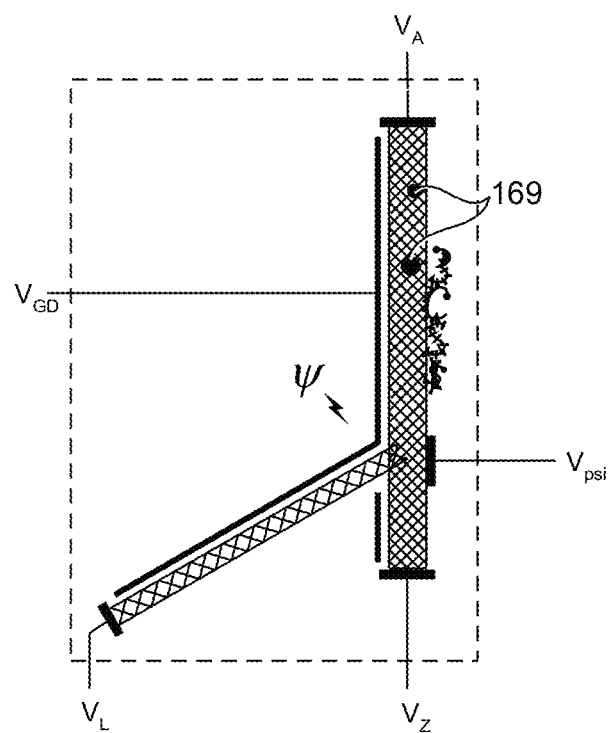
FIG. 1f is a diagram of a psychotronically-steerable, bifurcated "full trunk/L-field" conscious-gate transistor built from two carbon nanotubes, having a semiconducting "trunk", a semiconducting "L", and optional DNA segment, single or double-stranded, and deliberate defects.

FIG. 1f is a diagram of a psychotronically-steerable, bifurcated "full trunk/L-field" conscious-gate transistor built from two carbon nanotubes, having a semiconducting "trunk" and "L", and optional DNA segment, single or double-stranded, and deliberate defects. FIG. 1f is similar to FIG. 1e, except the trunk (and/or optionally the "L") is intentionally modified by e-beam or ozone during the assembly process to incorporate defects 169, which alter the electrical characteristics/sensitivity of the CNT transistor 100.

Figure 1G:
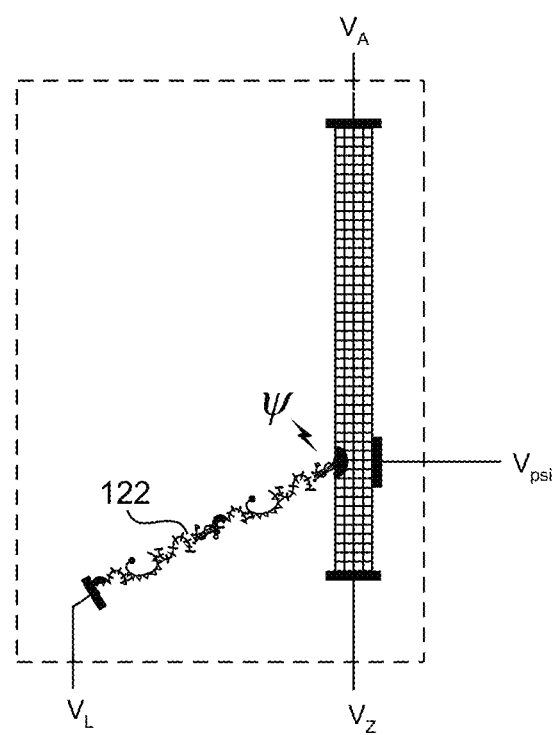
FIG. 1g is a diagram of a psychotronically-steerable, bifurcated conscious-gate transistor built from one metallic carbon nanotube as the trunk and DNA segment acting as a wire for the "L" after being inserted into the metallic carbon nanotube trunk, the DNA being either single or double stranded and, optionally, impregnated with silver and/or nickel nanoparticles.

FIG. 1g is a diagram of a psychotronically-steerable, bifurcated conscious-gate transistor built from one metallic carbon nanotube as the trunk and a DNA segment acting as a wire for the "L" after being inserted into the metallic carbon nanotube trunk, the DNA segment being either single or double stranded and, optionally, impregnated with silver and/or nickel nanoparticles. FIG. 1g is similar to FIG. 1a, except it has no field and the "L" is a segment of ssDNA 122 used in lieu of a CNT. To enhance rigidity and to also alter electrical characteristics, the ssDNA 122 may be impregnated with, for example, silver (and/or nickel) nano-particles.

Figure 1H:
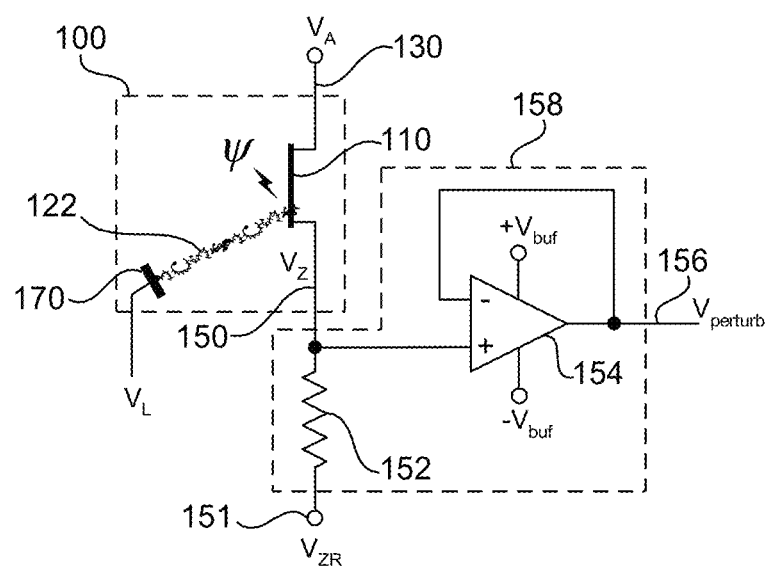
FIG. 1h is a schematic diagram showing a voltage follower method for buffering the output of an "L-field" conscious-gate transistor using an operational amplifier.

FIG. 1h is a schematic diagram showing a voltage follower method for buffering the output of an "L-field" conscious-gate transistor using an operational amplifier. FIG. 1h shows a method for buffering the $V_Z$ 150 output of the bifurcated CNT transistor 100. In this instance, the trunk 110 is a metallic carbon nanotube and the "L" 122 is ssDNA segment, but transistor 100 may be built from any of the previously described combinations of metallic and/or semiconducting carbon nanotubes. When a potential is applied across $V_A$ input 130 and $V_{ZR}$ 151, current will flow through the trunk 110 and resistor 152. If $V_L$ contact 170 is at the same or similar potential as $V_{ZR}$ 151, a portion of the current flowing through trunk 110 will also flow through "L" 122. When no current is flowing through trunk 110, the voltage drop across resistor 152 is zero and thus the output voltage 156 of operational amplifier 154 will be the same as 151. If current is flowing through trunk 110, the voltage drop across resistor 152 will be proportional to the amount of current flow and such will be reflected on the output 156 of op-amp 154. In this instance, op-amp 154 is configured as a voltage follower buffer 158 with unity gain. Assuming current is simultaneously flowing through both the trunk 110 and the "L", any fluctuation of the current through "L" 122, such as would be the case in a psychotronic perturbation of transistor 100, will affect the current flow through resistor 152 and be reflected on the output 156 of op-amp 154.

Figure 1I:
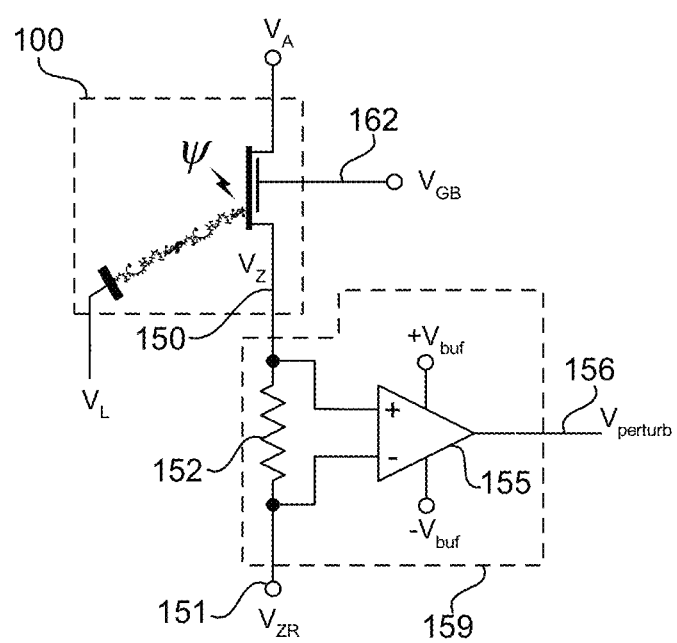
FIG. 1i is a schematic diagram showing an instrumentation amplifier method for buffering the output of a trunk-field conscious-gate transistor.

FIG. 1i is a schematic diagram showing an instrumentation amplifier method for buffering the output of a trunk-field conscious-gate transistor. FIG. 1i shows a method for buffering and amplifying the $V_Z$ 150 output of transistor 100. In this instance, transistor 100 of FIG. 1i is the same as transistor 100 of FIG. 1h, except the trunk of FIG. 1i has a field 162, i.e., the trunk is semiconducting. The buffer/amplification circuit 159 of FIG. 1i employs an instrumentation amplifier 155 for its high common mode rejection ratio and extremely high input impedance. Instrumentation amplifier 155 measures the difference between the potential of $V_Z$ 150 and $V_{ZR}$ 151. If no current is flowing through resistor 152, the output 156 of amplifier 155 will be zero. If current is flowing, then the output 156 will be the voltage drop across resistor 152 times the preset gain of instrumentation amplifier 155. Like the previously described buffer circuit of FIG. 1h, any perturbation of transistor 100 will appear on the output 156 of amplifier 155, except amplified/multiplied by a factor determined by the gain of amplifier 155.

Figure 1J:
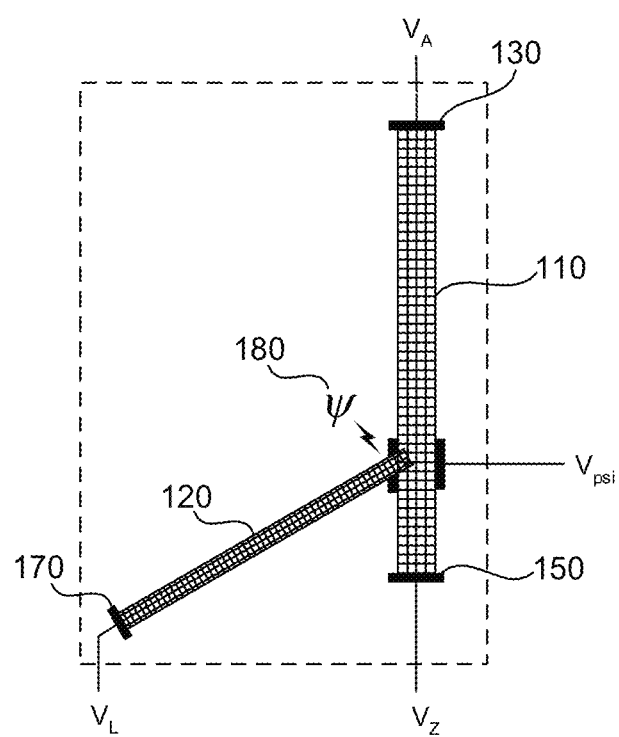
FIG. 1j is a diagram showing a conscious-gate transistor built from two metallic carbon nanotubes.

FIG. 1j is a diagram showing a conscious-gate transistor built from two metallic carbon nanotubes. FIG. 1j is similar to FIG. 1a, except both the trunk 110 and the "L" 120 are metallic carbon nanotubes. Consequently, there is no field for either. At first glance, some might argue that because there is no field (i.e., no gate), then this cannot be a "transistor" in the commonly understood meaning of the term. On the contrary, this is in fact a transistor, because any psychoenergetic perturbation of junction 180 will affect which path (and how much) current will flow through $V_L$ 170 and/or $V_Z$ 150 at any given instant. Like the previously described transistors, this all metallic transistor may be decorated with DNA (single or double strand segment), RNA (folded or unfolded), enzymes, proteins, nanoparticles, and/or modified to include defects using e-beam or ozone.

Figure 2:
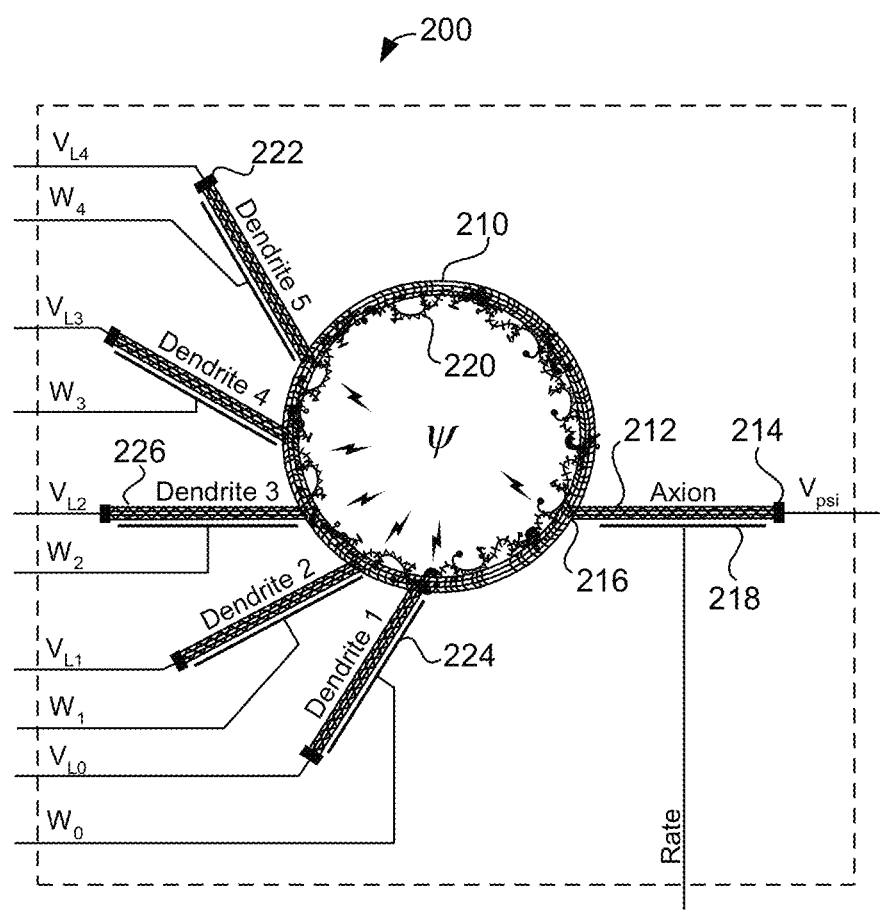
FIG. 2 is a diagram of a bidirectional, multi-channel conscious-gate multiplexer/psyclotron that can also function as a pseudo-neuron, built from one metallic carbon nanotorus with six smaller radius semiconducting carbon nanotubes inserted into the nanotorus outer radius wall, and, optionally decorated with DNA.

FIG. 2 is a diagram of a bidirectional, multi-channel conscious-gate multiplexer/psyclotron that can also function as a pseudo-neuron, built from one metallic carbon nanotorus with six smaller radius semiconducting carbon nanotubes inserted into the nanotorus outer radius wall, and, optionally decorated with DNA or RNA. The bidirectional conscious-gate multiplexer/channel-selector/combiner/distributor/neuron, hereinafter referred to as a "psyclotron" 200, can be employed in several different ways. For example, the psyclotron can be employed as a channel multiplexer, an artificial neuron, and a current distributor to name just a few uses. The psyclotron includes two or more dendrite "L(s)" 226, two or more dendrite "L" electrical contact(s) 222, two or more optional dendrite "L" field(s) 224, a metallic or semiconducting carbon nanotori 210, an axion "L" 212, an axion "L" electrical contact 214, and an optional axion "L" field 218. The junctions where the "L"s are inserted into the carbon nanotori may optionally have electrical contacts 216, which if present, should be symmetric, meaning they should all be the same material. In addition, the nanotori and/or "L"s may be decorated with ssDNA, RNA (folded or unfolded), enzymes, proteins, or nanoparticles. The dendrite "L"s 226 may be metallic (in which case no field 224 is required) or semiconducting (in which case a field is required), or the dendrite "L"s may be built from ssDNA and optionally impregnated with silver and/or nickel nanoparticles. The axion "L" 212 may be metallic (in which case no field 218 is required) or semiconducting (in which case field 218 is required), or the axion "L" may be built from ssDNA and optionally impregnated with, for example, silver or nickel nanoparticles.

The optional fields of the dendrite "L"s and/or the axion "L"s may be split-gate, meaning instead of one field per dendrite or axion, there are two or more fields, which operate at different potentials, which can be made to have the effect of a P-N junction diode. Although not specifically shown in 200, the carbon nanotori 210 may be semiconducting or metallic. If metallic, then no field is required. If semiconducting, then a field is required.

Certain metallic nanotori have been shown to exhibit a persistent current phenomenon. Certain semiconducting nanotori have also been shown to exhibit a persistent current in the presence of a field. As an analogy of how the psyclotron 200 might be used, think of a traffic circle in the middle of a city where there are no stop signs, only yield signs. As you drive in one direction in the circle, you see not only informational or cautionary signs, which advise you which street to turn onto and what to look out for, but you also may see advertisements, which attempt to influence your purchasing choices. This is the main idea with the toroid in the instant invention. With the ssDNA decoration, the DNA passes instructions (subtle potentialities) to the electrons and any other subatomic or virtual particles that may be playing a role in the process. The DNA or RNA may also have the ability to alter or influence the electrons' spin while in such close proximity to it. The DNA or RNA translates the volition of the donor percipient into instructions the electrons and subatomic/virtual particles can carry out, in this case, where to turn or which dendrite "L" to enter into or exit from (since the psyclotron 200 can be used in either direction, which will be explained later in the present disclosure), similar to the way information transfer occurs in the human body.

At this point, it should be made very clear that the present invention is not intended to be implanted into the body. Although it could be implanted, it does not need to be implanted. The ssDNA (or segment thereof) is a stand-alone molecule and can survive indefinitely outside the body so long as it is protected from exposure to elements that would alter its chemistry.

So now the question is: "How does the ssDNA or RNA know that the donor percipient had a volition directed at it?" The simple answer: something akin to quantum entanglement. And because of that, such communication is instantaneous. Assuming that because the ssDNA decoration is so closely coupled to the vacuum state by way of the "tiniest bit of nothing" occupying the space inside the nanotube, where classical mechanics goes out the window, quantum physics comes into play, and, as a result, communication does not travel through classical space-time as we understand it. The tiniest bit of nothing inside one CNT is the same identical tiniest bit of nothing inside another CNT, meaning they occupy the same virtual point (which is not even a point) within the vacuum state, which is why information transfer between two different CNTs via this channel, no matter how distant the separation between them, is instantaneous.

This gives rise to the question, "Well then, since humans do not have, per se, carbon nanotubes within their body for DNA to couple onto, how does a human psychotronically transmit or receive information via the vacuum state communication channel?" Closest answer: via certain microtubules residing in neurons within the human body, which determine its shape and structure and provide, among other things, a channel of informational communication. While one of the roles of microtubules is to deliver materials and information into the neuron which continually alter its shape and structure, there are most likely microtubules that have sections that remain completely hollow, like the carbon nanotube. Furthermore, there may be some microtubules within a given neuron whose entire purpose is information transfer via the vacuum state communication channel, in that their interior diameter is typically on the order of only 17 nm, which, relatively speaking, is about 7 times larger than that of trunk CNTs employed in the instant disclosure 3D models.

From FIG. 2, it can be seen that when semiconducting CNTs are employed as dendrite "L"s, their respective fields 224 can control the amount of conductance through that "L" proportional to the magnitude of that field, which can be used to apply, by way of a digital-to-analog (D/A) converter or fixed voltage reference, a weight to the VL 222, which allows that dendrite "L" to mimic that aspect of a biological neuron. The same is true for the axion "L" 212 when semiconducting CNTs are employed for that purpose. Furthermore, when not explicitly being employed to mimic a biological neuron, 200 can be employed as a bidirectional multiplexer, provided, of course, that the dendrite "L"s are semiconducting CNTs and have respective fields. When axion 212 is a semiconducting CNT, its field 218 can be used to control the amount of current entering or exiting axion 212.

Figure 3:
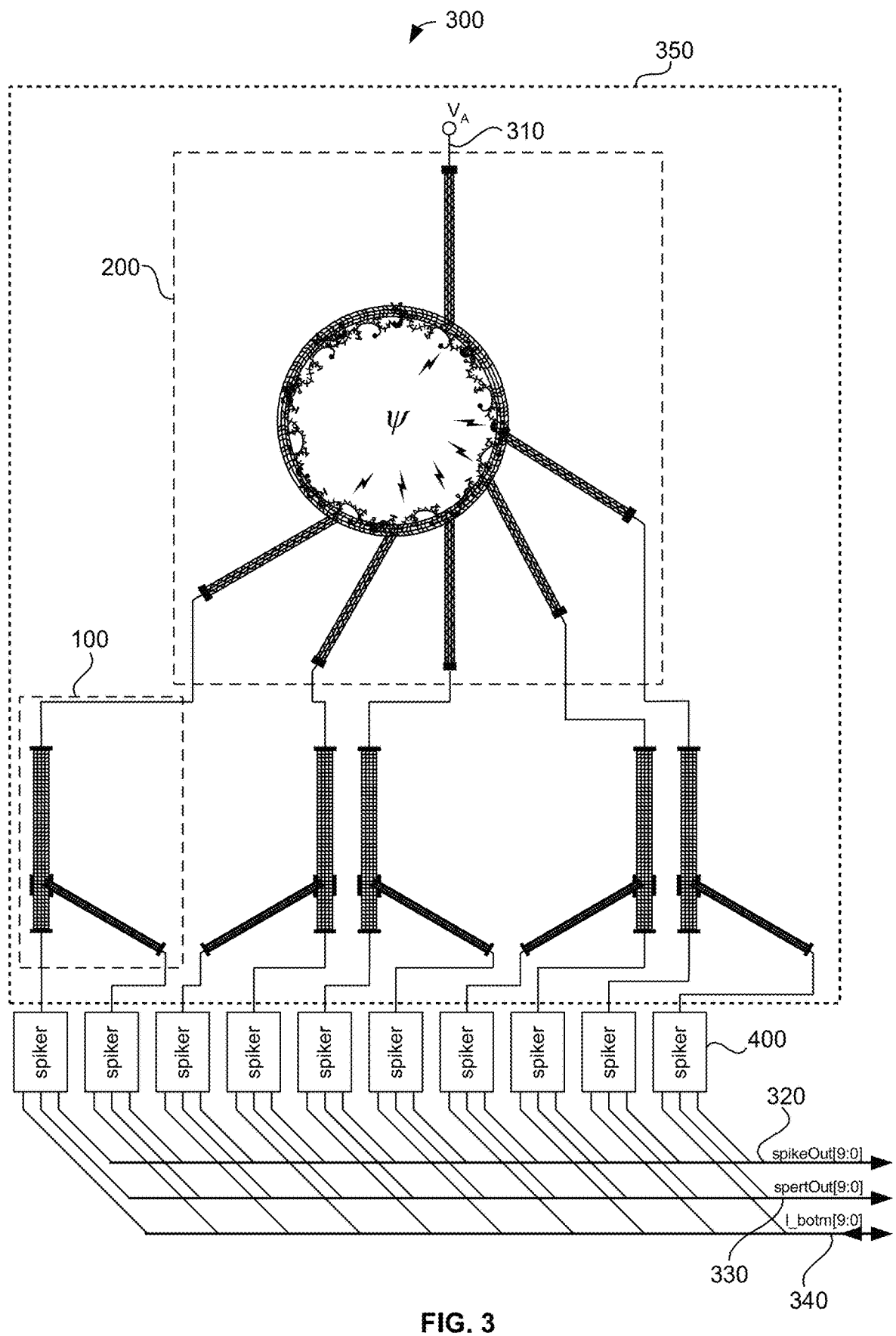
FIG. 3 is a diagram of the top portion of a vacuum state information unfolder built from a carbon nanotorus and five conscious-gate transistors binning-out into their respective spike generators.

FIG. 3 is a diagram of the top portion of a vacuum state information unfolder built from a carbon nanotorus and five conscious-gate transistors binning-out into their respective spike generators. FIG. 3 shows the upper half 350 of a 10-bit, bidirectional, conscious-gate, psychcotronically steerable, vacuum state information unfolder 300 comprising an ssDNA-decorated, all-metallic psyclotron 200, five bifurcated conscious-gate transistors 100, and ten spike/spert generators 400. As can be seen from FIG. 3, electrical current enters psyclotron VA contact 310 and eventually merges into the carbon nanotorus traffic circle where it receives information from the ssDNA decoration and eventually exits the traffic circle according to its informational instructions by way of one of the dendrite "L"s. The current then enters the prescribed "L" trunk 100 where the current then either continues down the trunk past the "L" junction or exits via the "L" of bifurcated transistor, all according to the instructions it received while in the traffic circle of 200. After exiting either the trunk or "L" of 100, it then enters the respective "spiker" circuit 400. If the charge at that moment (or at any moment within a given "sync" frame of 400) is greater than the pre-programmed lower trigger point (LTP), a "spert" pulse exactly one clock in duration will be produced on its respective spert output 330, otherwise the spert output will remain a logic 0 for at least one clock cycle. Simultaneous with the sampling of the LTP, if the charge at that moment is greater than the pre-programmed upper trigger point (UTP), a "spike" pulse exactly one clock in duration will be produced on its spike output 320, otherwise the spike output will remain a logic 0 for at least one clock cycle. Each current that exits the bottom of the trunk or "L" of 100 enters their respective spiker 400 circuit, where it flows through a series resistor used for measuring potential and then exits the resistor as I_botm 340.

Figure 4:
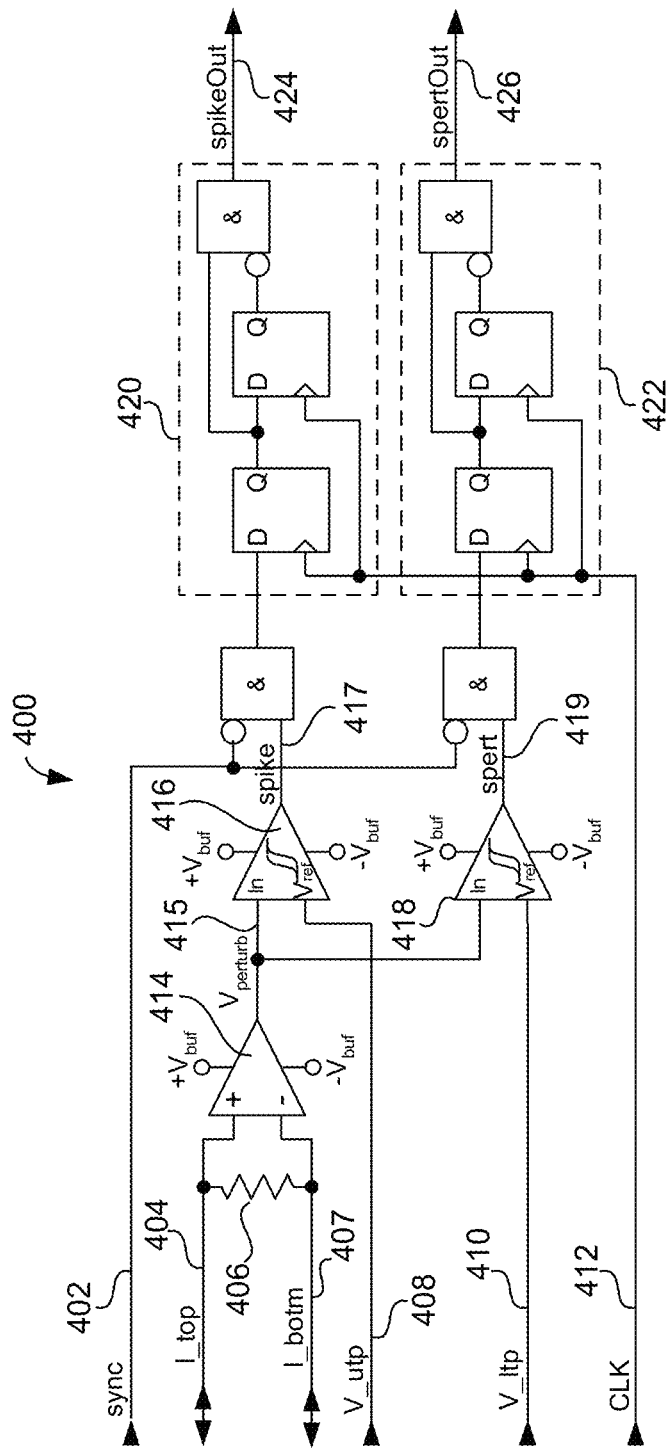
FIG. 4 is a schematic diagram for a spike generator.

FIG. 4 is a schematic diagram for a spike generator 400. The circuit includes series resistor 406, instrumentation amplifier 414, programmable Schmitt triggers 416 and 418, and two synchronous one-shot circuits 420 and 422, one for generating a spike on spikeOut 424 and one for generating a spert on spertOut 426.

Current from either a trunk or "L" from a bifurcated transistor 100 of 350 enters resistor 406 via I_top 404. The current then flows through resistor 406 and exits as I_botm 407. This I_botm 407 current continues on and enters the bottom half of the system, where the information it carries is eventually re-folded back into the vacuum state.

As can be seen from circuit 400, if the difference in potential between I_top 404 and I_botm 407 presented by amplifier 414 to its output as Vperturb 415, is greater than the lower trigger point reference voltage 410, then Schmitt trigger 418 will go to logic 1 and present itself as signal spert 419, indicating the lower trigger point 408 has been reached. Spert signal 419 is gated with a periodic, active high, sync pulse that is synchronous with the system clock, CLK 412, such that when sync 402 is at a logic 1, the gated spert signal will a be a logic 0. Only when sync 402 is a logic 0 (i.e., no sync taking place) will spert 419 pass through to its respective on-shot circuit 422. This periodic synchronization provides a frame of reference for the resulting spike/spert train generated by disclosed vacuum state information unfolding system. As a final step, the gated spert signal then enters a synchronous digital one-shot circuit 422 where a single pulse, one-clock in duration, is generated each time spert 419 transitions from a logic 0 to a logic 1 anytime sync 402 is not active, i.e., not at a logic 1 state, presenting itself as spertOut 426.

SpikeOut 424 is generated exactly the same way as spertOut 426, except its reference voltage, V_utp 408, will usually be somewhat greater than the lower trigger point V_ltp 410. If Vperturb 415 is greater than V_utp 408, then Schmitt trigger 416 output, spike 417, will go active high, but only if there is no sync 402 cycle during that time. If synchronous one-shot circuit 420 detects that spike 417 is active high, it will produce an active high pulse on its output and present it as spikeOut 424.

At this point it should be understood that the current entering and exiting I_top 404 and I_botm 407 (respectively) can be swapped, such that current enters via I_botm 407 and exits via I_top 404. This optional feature is intended mainly to provide a means to essentially "flush" the system periodically if desired or needed. With this particular circuit 400, if the input current comes in from I_botm 407 instead of I_top 404, the polarity of amplifier 414 output will be inverted, and, consequently will prevent the Schmitt triggers from triggering properly. Thus, a flush should only be performed when sync is active high. One way to make 400 truly bidirectional is to employ instrumentation amplifiers whose output is the 'absolute value' of the difference input.

Figure 5:
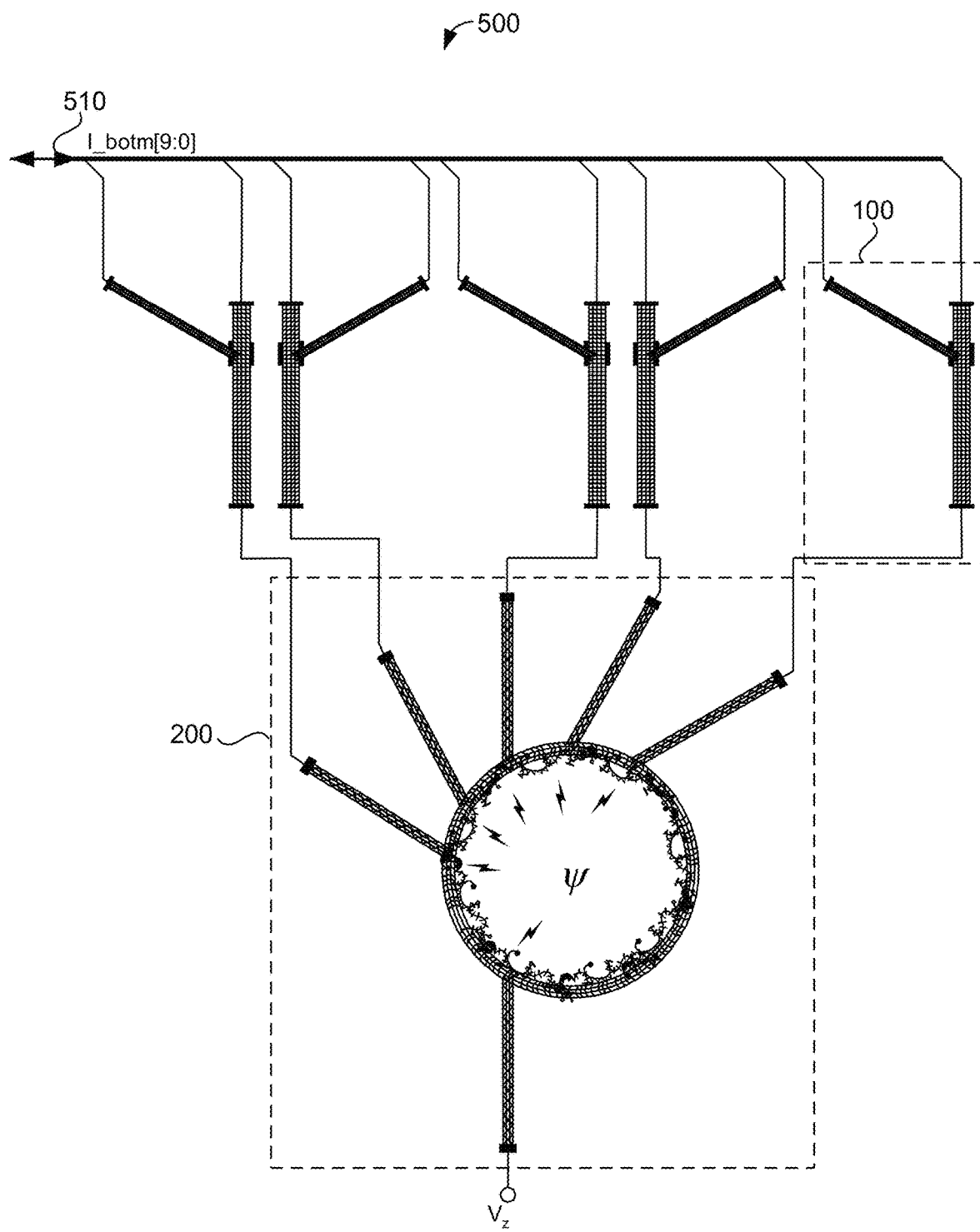
FIG. 5 is a diagram of the bottom half of a vacuum state information re-folder built from a carbon nanotorus and five conscious-gate transistors with their inputs flipped in relation to their corresponding conscious-gate transistors in the top portion of the vacuum state information unfolder.

FIG. 5 is a diagram of the bottom half of the a vacuum state information re-folder built from a carbon nanotorus and five conscious-gate transistors with their inputs flipped in relation to their corresponding conscious-gate transistors in the top portion of the vacuum state information unfolder. FIG. 5 shows the bottom half 500 of the vacuum state information unfolder 300. One of its functions is to re-fold the information that was unfolded by the upper half 350. Another function is to act as a potentiality ballast or gimbal from the perspective of the electrons flowing through it, in that as they pass through the network, they all make at least one pass through a bifurcated transistor's "L". Otherwise, some electrons flowing through it will pass through only the trunk and never an "L". The bottom half includes a psyclotron traffic circle 200 similar to the one in the upper half, except, in this instance, the dendrite "L"s are inputs instead of outputs. The bottom half also includes the same number of psychotronically steerable bifurcated transistors 100 as the upper half. Current coming out of resistor 406 of the spiker circuit 400 enters the lower half via bus 510.

Note that current exiting the trunk from the upper half always enters an "L" in the lower half and current exiting an "L" in the upper half always enters a trunk in the lower half. It should also be noted that current in the psyclotron traffic circle of the upper half flows in one direction while the current in the psyclotron of the lower half flows in the opposite direction.

Figure 6:
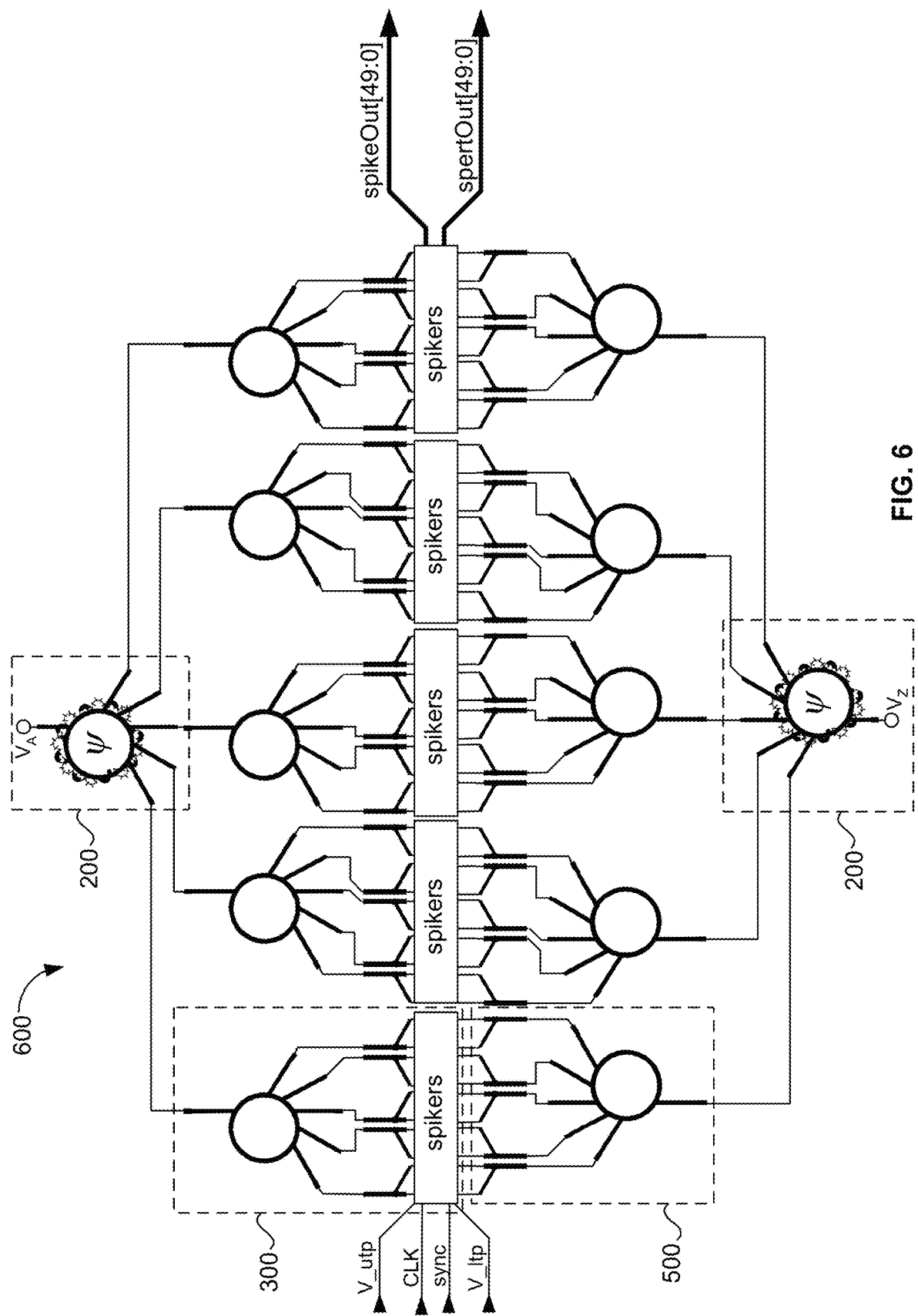
FIG. 6 is a diagram of the vacuum state information unfolder showing the relationship between the upper half unfolder and the bottom half re-folder and spike generators.

FIG. 6 is a diagram of the vacuum state information unfolder showing the relationship between the upper half unfolder and the bottom half re-folder and spike generators. FIG. 6 shows how to nest multiple 10-bit vacuum state information unfolders to create a 50-bit vacuum state information unfolder 600, which provides fifty spike bits and fifty spert bits. With this approach, there is only one entrance point and only one exit point through which current enters and exits the network.

Figure 7:
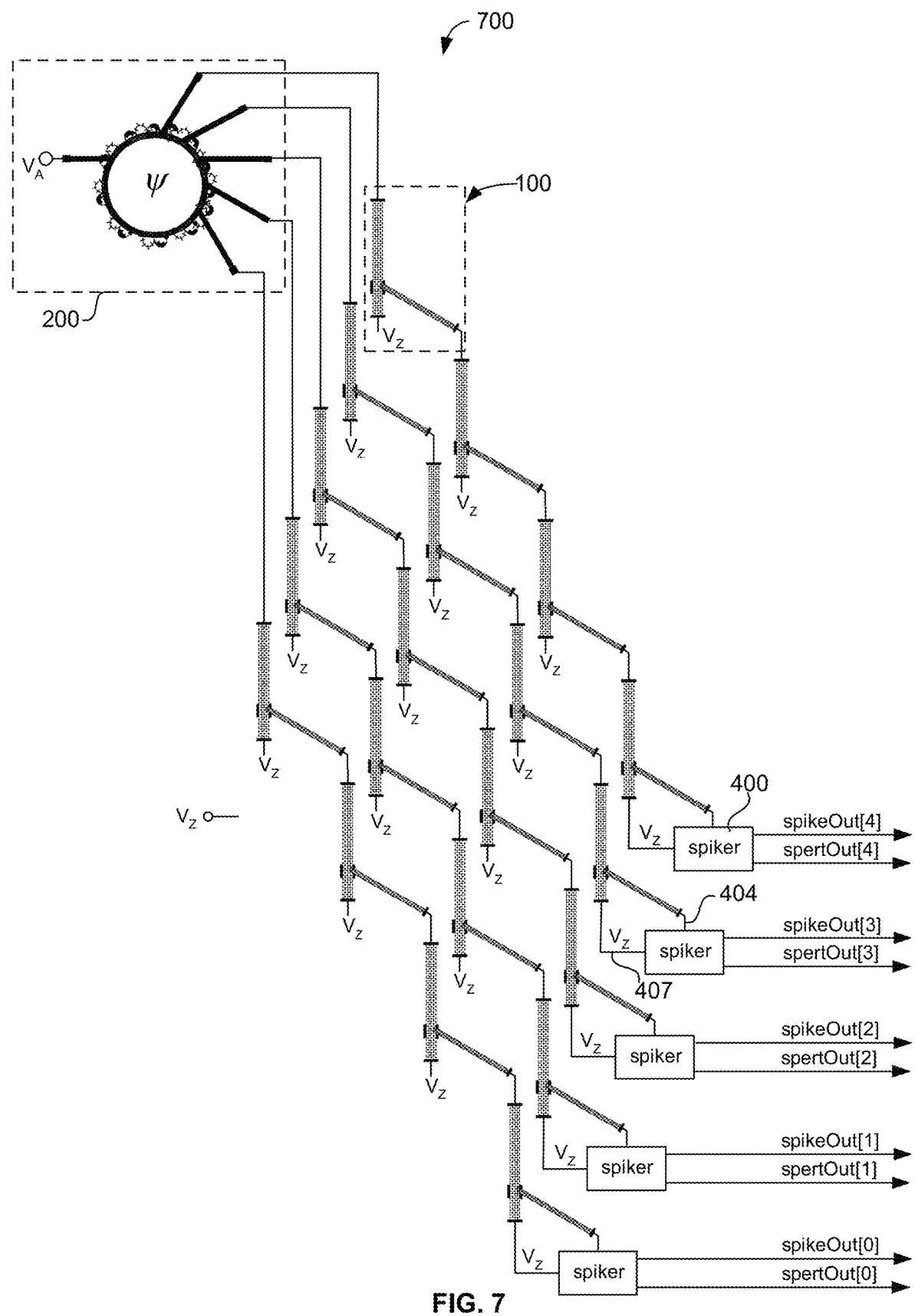
FIG. 7 is a diagram of a different version of a vacuum state information unfolder that uses a gradual charge shedding method of information extraction.

FIG. 7 is a diagram of a different version of a vacuum state information unfolder that uses a gradual charge shedding method of information extraction. FIG. 7 is a slightly different kind of vacuum state information unfolder referred to as an information sifter 700. There is one point through which current enters the system at $V_A$ of psyclotron 200. However, unlike the information unfolder of FIG. 6, the information sifter of FIG. 7 has multiple current exit points. This approach is suitable for certain applications. It has the advantage of being more simplistic and cheaper to manufacture, calibrate, and test. While it may appear that most of the current that enters the system will go directly to the $V_Z$ terminal, it is important to consider the fact that the nanotubes will eventually saturate, limiting the amount of current that passes through them. Note that the "L" junction is located about 25 percent of the way up the length of the trunk. Consequently, while the trunk is in saturation mode, self-limiting the amount of current that flows through its entire length, a certain percentage of the current will have an opportunity to carry out its programming by going down the "L", which has more conductance because it is not yet saturated.

Figure 8:
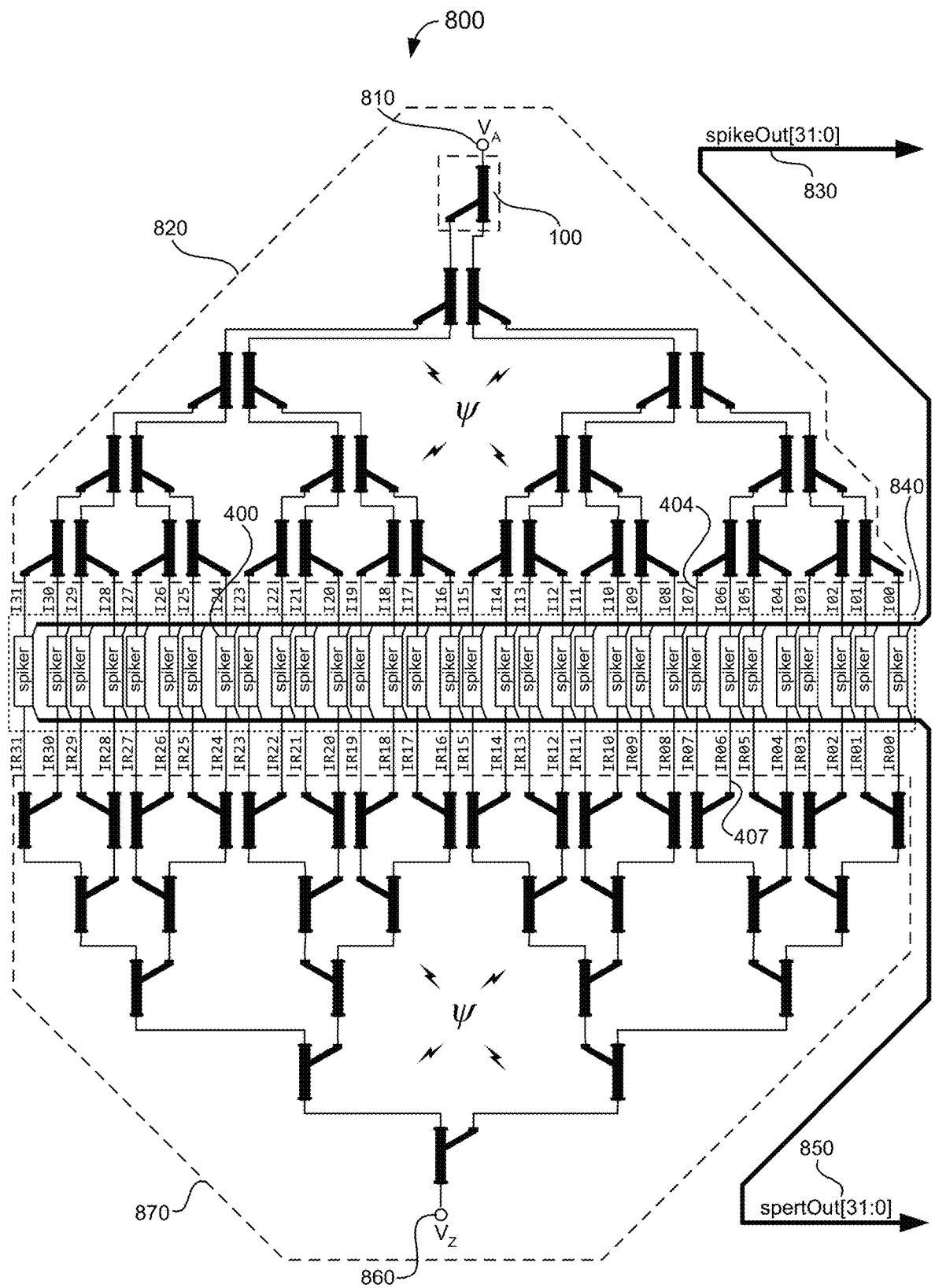
FIG. 8 is a diagram of a vacuum state information unfolder/re-folder with 64-bit spike train output (32 bits of which are spikes and the other 32 bits sperts) showing the relationship between upper unfolder portion to the lower re-folder portion, both comprising bifurcated conscious-gate carbon nanotube transistors, all metallic in this instance, and having bidirectional unfolding/re-folding ability.

FIG. 8 is a diagram of a vacuum state information unfolder/re-folder with 64-bit spike train output (32 bits of which are spikes and the other 32 bits sperts) showing the relationship between an upper unfolder portion to a lower re-folder portion, both comprising bifurcated conscious-gate carbon nanotube transistors, all metallic in this instance, and having bidirectional unfolding/re-folding ability. The information unfolder circuit 800 comprises an upper half 820 and a lower half 870 of a 32-bit information unfolder, having a single current input 810 and a single current output 860 into and out of the system. Like the information unfolder of FIG. 6, the input 810 and output 860 can be swapped such that input 810 then becomes an output and output 860 becomes an input and circuit 820 becomes the lower half and circuit 870 becomes the upper half. Circuits 820 and 870 each comprise thirty-two psychotronically steerable bifurcated conscious-gate carbon nanotube transistors 100, in this instance, all metallic. The transistors 100 may be decorated with ssDNA, RNA (folded or unfolded), enzymes, proteins, and/or nanoparticles, and may be intentionally modified to have defects.

Moreover, the carbon used to synthesize the CNTs incorporated into the information unfolder circuit 800 may have been extracted from a specific percipient's blood/body tissues, so as to take advantage of quantum entanglement phenomena. This way, the information unfolder 800 and donor percipient have a more "natural," symbiotic relationship and thus 800 is more likely to perform at its peak and without the percipient having to exert as much volitional psychotronic energy at the information unfolder 800 to get it to yield the information being sought by the donor percipient, close relative, or member of the same genome.

Similar to the information unfolder of FIG. 6, the current 404 coming out of a trunk or "L" of the transistors 100 of the upper half 820 that directly interface to the spikers 840 where a spikeOut 830 or spertOut 850 may or may not be generated during a given clock cycle, passes through that spiker's series resistor 406 of FIG. 4 and this current 407 continues to the bottom half 870 by entering a trunk or "L" of a transistor 100 interfacing to the spiker output.

As can be seen from the information unfolder circuit 800, current enters a $V_A$ 810 where it is continually split according to the instructions it is carrying and eventually winds up "binning-out" at the one or more spikers prescribed in the instructions programmed into it by way of phsycotronic perturbation, ssDNA, or RNA, according to the percipient's intention/volition. If enough electrons bin-out at their corresponding spiker circuit, a spikeOut pulse will be generated for that specific bin. A spikeOut pulse 830 will always have a corresponding spertOut pulse 850 that occurs either prior to or simultaneously with the spikeOut during a synchronized frame. If a spiker does not produce a spertOut pulse throughout a synchronized frame, this means another spiker in the information unfolder circuit 800 is depriving it of its share of current. In a dead universe, all (or almost all) spikers of the information unfolder circuit 800 will produce one spertOut pulse and no spikeOut pulse every synchronized frame. The only way for spikeOut to be produced is for some conscious entity to direct a volition at it commanding the information unfolder circuit 800 to respond by yielding information from the vacuum state. In this manner, information from the vacuum state is said to be unfolded, in that the binning-out process yields meaning either directly or with the aid of adequately trained artificial neural networks.

Once the current 407 exits the spiker circuit, it enters the lower half 870 by entering the trunk or "L" of bifurcated transistor 100. It then begins the unfolding process in reverse—re-folding. Eventually the current (and information it carries) is completely re-folded back into the vacuum state by the time it exits at $V_Z$ 860.

Similar to the previously described 10-bit vacuum state information unfolder 600 of FIG. 6, the transistors 100 of the information unfolder circuit 800 are oriented such that the current flowing through the upper half sees the same number of trunks and "L"s when it flows through the lower half. This symmetry creates something similar to buoyancy or ballast/balance across the entire network. When psychotronically perturbed with a volition directed at the information unfolder circuit 800, it can also function as a quantum gimbal.

Figure 9:
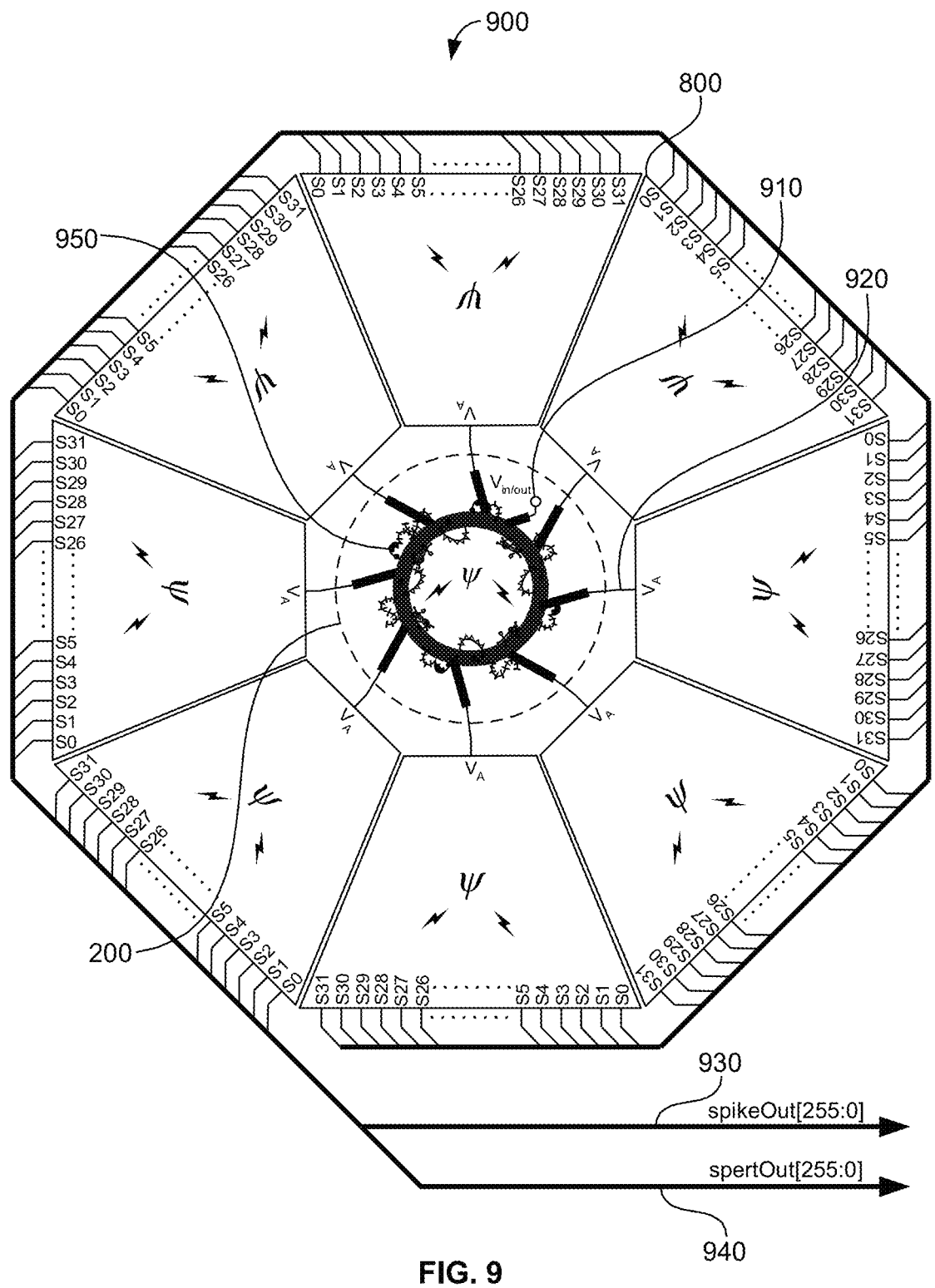
FIG. 9 is a diagram of a bidirectional vacuum state information unfolder/re-folder with 512-bit spike train output (256 bits of which are spikes and the other 256 bits sperts) built from eight unfolder/re-folders of FIG. 8 and two carbon nanotorus conscious-gate psyclotrons (the second psyclotron not shown in this diagram because it's underneath)

FIG. 9 is a diagram of a bidirectional vacuum state information unfolder/re-folder with 512-bit spike train output (256 bits of which are spikes and the other 256 bits sperts) built from eight unfolder/re-folders of FIG. 8 and two carbon nanotorus conscious-gate psyclotrons (the second psyclotron is not visible in this diagram because it is underneath the one shown). FIG. 9 shows a 256-bit psychotronic vacuum state information unfolder 900 comprising eight 32-bit psychotronic vacuum state information folders 800 and two eight-dendrite versions of the psyclotron 200, one for the eight upper halves of the information unfolder circuit 800 and one for the eight lower halves of the information unfolder circuit 800, which may be decorated with a percipient's ssDNA or RNA 950. Current enters the axion 910 of the psyclotron 200 and enters the traffic circle of persistent currents, receiving directions/instructions from the ssDNA and information from the vacuum state existing at the interior of the psyclotron 200. Then the current exits at the prescribed psyclotron dendrite and enters the upper half $V_A$ 920 and begins the information unfolding and re-folding process, eventually producing synchronized spike trains spikeOut 930 and spertOut 940, which may be in human-readable form (ASCII alpha-numeric characters and/or decimal character sequences) or may eventually be submitted to an artificial spiking neural network for processing by a conventional computer for further processing and storage.

The current then exits the spiker circuit of the information unfolder circuit 800 and begins the information re-folding process until it exits via $V_Z$ 860 and then enters the corresponding dendrite of bottom half psyclotron 200 (not shown) and eventually exits the bottom half psyclotron via its axion "L" 212.

Figure 10:
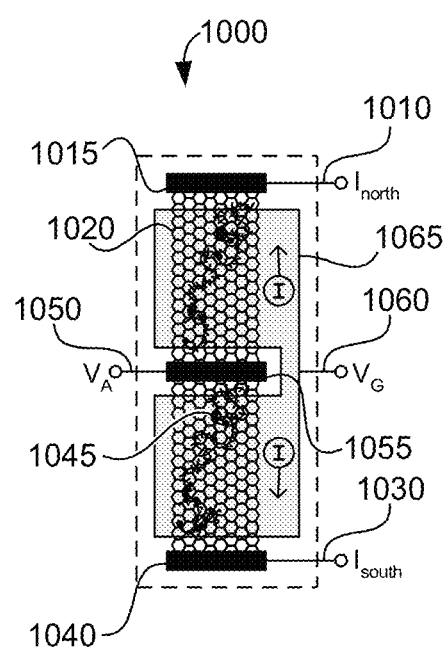
FIG. 10 is a diagram of an alternative to the bifurcated carbon nanotube conscious-gate transistor, this one being built from two strips of graphene with optional DNA decoration and which might be substituted for use in the bidirectional vacuum state information unfolder/re-folder of FIG. 9.

FIG. 10 is a diagram of an alternative to the bifurcated carbon nanotube conscious-gate transistor, this one being built from two strips of graphene with optional DNA decoration and which might be substituted for use in the bidirectional vacuum state information unfolder/re-folder of FIG. 9. FIG. 10 shows a bifurcated conscious-gate transistor 1000 constructed, for example, from a flat strip of graphine 1020 rather than two carbon nanotubes of transistor 100, in an alternative embodiment of the conscious-gate transistor 100. A single carbon nanotube may also be substituted for the single flat strip of graphine 1020, which can optionally be decorated with ssDNA, RNA (folded or unfolded), enzymes, proteins, and/or nanoparticles, and/or modified to have defects, including by way of crumpling.

Current enters by way of the $V_A$ terminal 1050 and can turn north and/or south, across graphine strip 1020 until reaching respective contacts 1015 and/or 1040 and exiting via their respective Inorth 1010 and/or Isouth 1030 terminals. If graphine strip 1020 is metallic (i.e., "armchair"), then no field (backgate) 1065 is required. If graphine strip 1020 is semiconducting (i.e., zigzag), then a field/backgate is required, the field potential of the back-gate being applied at VG terminal 1060.

This alternative embodiment of transistor 100 is presented because the technology for synthesizing carbon nanotubes to have a desired diameter and chiralty (i.e., metallic or semiconducting), sorting and assembling them, etc., is still in its infancy.

While transistor 1000 has the advantage of being easier to manufacture and embed within a substrate, it does not appear to have direct access to the information within the vacuum state as is the case with transistor 100. The closest approach to that would be to substitute a single carbon nanotube for graphine strip 1020, but even then, there is still no direct access to the vacuum state absent modification of the carbon nanotube by incorporation of voids/defects into it by way of e-beam or ozone modification.

Because transistor 1000 would most likely be susceptible to psychotronic perturbation, especially if decorated with a percipient's ssDNA or RNA, it is expected that transistor 1000 could be used for such applications as psychotronically steerable directional control input devices and flipping on LEDs and such, but it does not appear that it would work as well when used for "natural knowing" kinds applications when substituted for transistor 100 in vacuum state information unfolder 800, for example. With that said, transistor 1000 can be directly substituted for transistor 100 in vacuum state information unfolder 800. After doing so, at a very minimum, one may wind up with a psychotronically perturbable directional control device that a percipient with at least some ability can employ to remotely control machines with only his or her volition.

Figure 11:
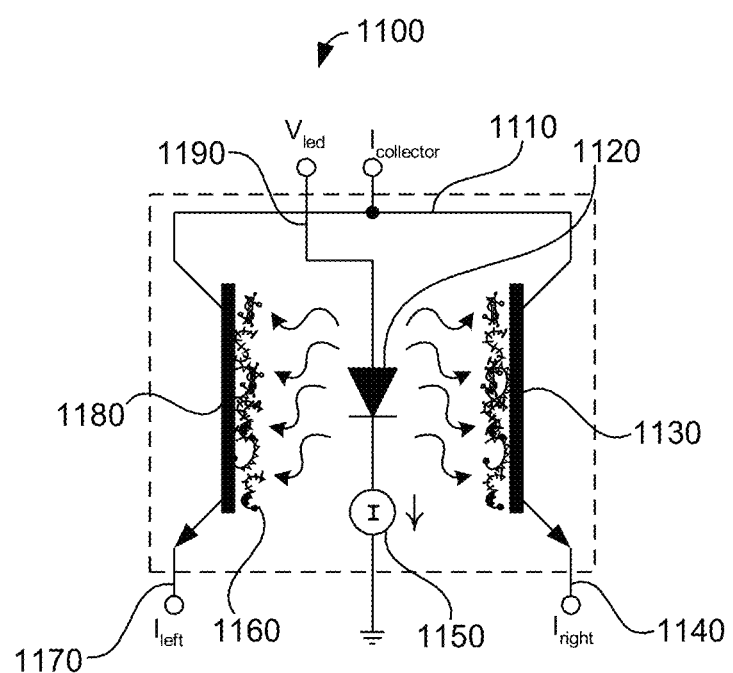
FIG. 11 is a diagram of another alternative to the bifurcated carbon nanotube conscious-gate transistor, this one being built from a light-emitting diode (LED) and two bi-polar junction transistor (BJT) photo-transistors optionally decorated with DNA through which photons emitted by the LED penetrate, impacting the photo-sensitive base of the BJTs.

FIG. 11 is a diagram of another alternative to the bifurcated carbon nanotube conscious-gate transistor, this one being built from a light-emitting diode (LED) and two bi-polar junction transistor (BJT) photo-transistors optionally decorated with DNA through which photons emitted by the LED penetrate, impacting the photo-sensitive base of the BJTs. FIG. 11 is another alternative embodiment of transistor 100, for the same reasons as transistor 1000. A dual photo-transistor 1100 includes a built-in LED 1120 as a photon source, which includes its own constant current source 1150, such that with a sufficient potential supplied at its $V_{led}$ terminal 1190, it emits a constant stream of photons, which penetrate and pass through the ssDNA or RNA decorating the bases of photo-transistor 1180 and matching photo-transistor 1130.

As the light passes through the percipient's ssDNA or RNA, instructions/information contained in the dsDNA, ssDNA or RNA (folded or unfolded) are imposed on the photons before impacting the base of transistors 1180 and 1130, such that when the photons knock electrons loose in these bases, the information/instructions are transferred to the electrons before being emitted through transistors 1180 and 1130 and their respective emitters 1170 and 1140 of photo-transistors 1180 and 1130, such that the electrons will follow the instructions thereby imposed on them as they traverse the maze of pathways to their respective prescribed destinations. To employ transistor 1100 as a substitute for transistor 100 in a circuit such as that of the upper half 820 of vacuum state information unfolder circuit 800, collector terminals 1110 of transistor 1100 must be tied together and the respective emitter terminals 1170 and 1140 must be separated. To employ transistor 1100 as a substitute for transistor 100 in a circuit such as that of the lower half 870 of vacuum state information unfolder circuit 800, collector terminals 1110 of transistor 1100 must be separated and the respective emitter terminals 1170 and 1140 must be tied together.

Like transistor 1000, while transistor 1100 would be susceptible to psychotronic perturbation, it does not appear that it would have direct access to the infinite information folded up in the vacuum state as in the case of transistor 100. As such, it is expected that transistor 1100 may nonetheless be used for such applications as psychoenergetically steerable directional control input devices and flipping on LEDs, but it does not appear that it could be used for "natural knowing" kinds applications when substituted for transistor 100 in vacuum state information unfolder 800, for example. Fortunately, in this respect, transistor 1100 can be directly substituted for transistor 100 in vacuum state information unfolder 800. After doing so, at a very minimum, one may wind up with a psychoenergetically perturbable directional control device that a percipient with at least some ability can employ to remotely control machines with only his or her volition.

Figure 12:
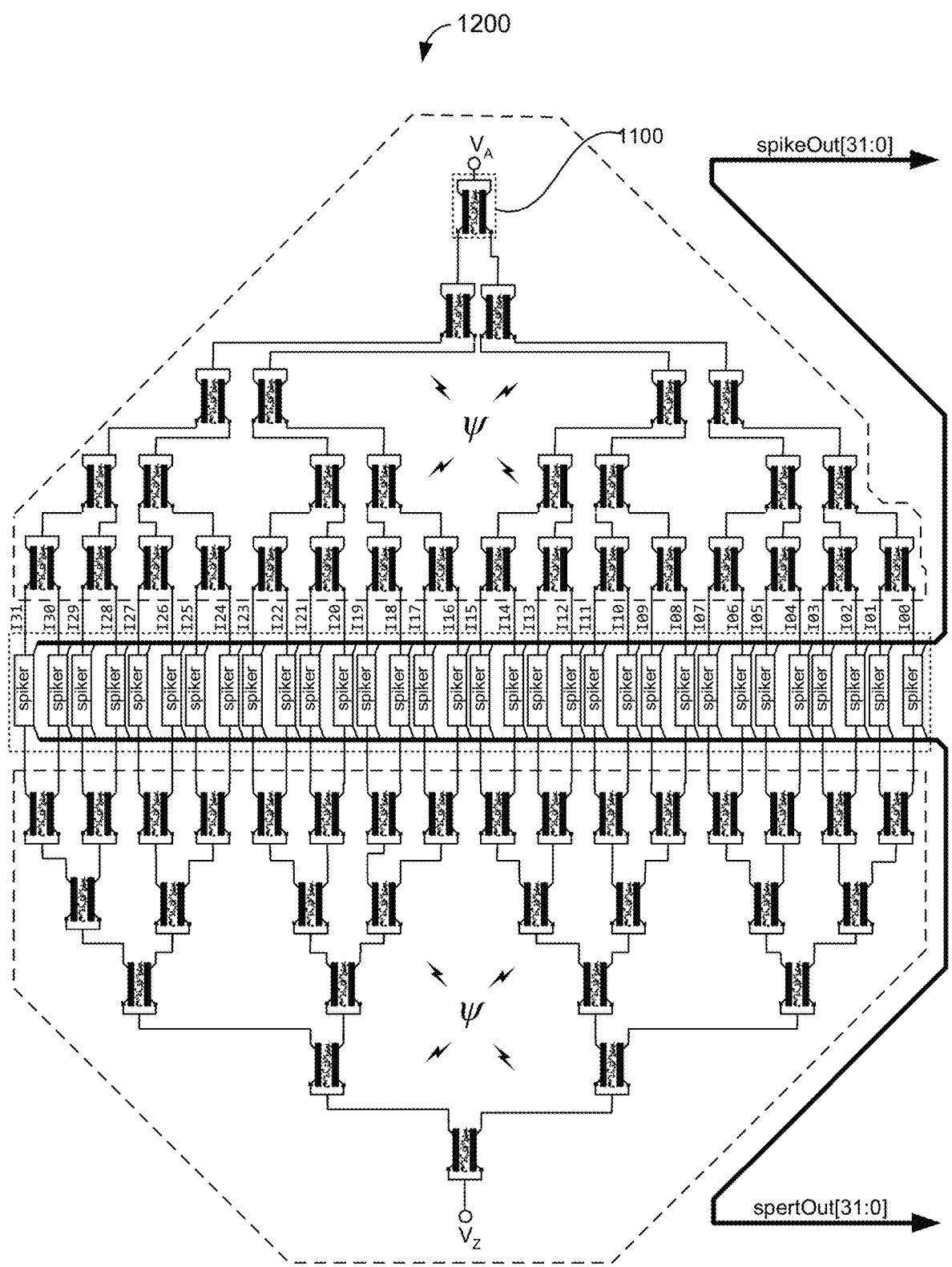
FIG. 12 is a diagram of a unidirectional alternative to the 512-bit, bidirectional vacuum state information unfolder/re-folder of FIG. 9, but which employs the bifurcated conscious BJT of FIG. 11.

FIG. 12 is a diagram of a unidirectional alternative to the 512-bit, bidirectional vacuum state information unfolder/refolder of FIG. 9, but which employs the bifurcated conscious BJT of FIG. 11. FIG. 12 is a diagram of a circuit 1200 showing what the circuit of 800 would look like with its transistor 100 substituted with dual photo-transistor 1100. Note that because the photo-transistors of 1100 are based on silicon BJT-type photo-transistors, current can only flow in one direction, unlike circuit 800 populated with transistor 100.

Figure 13A:
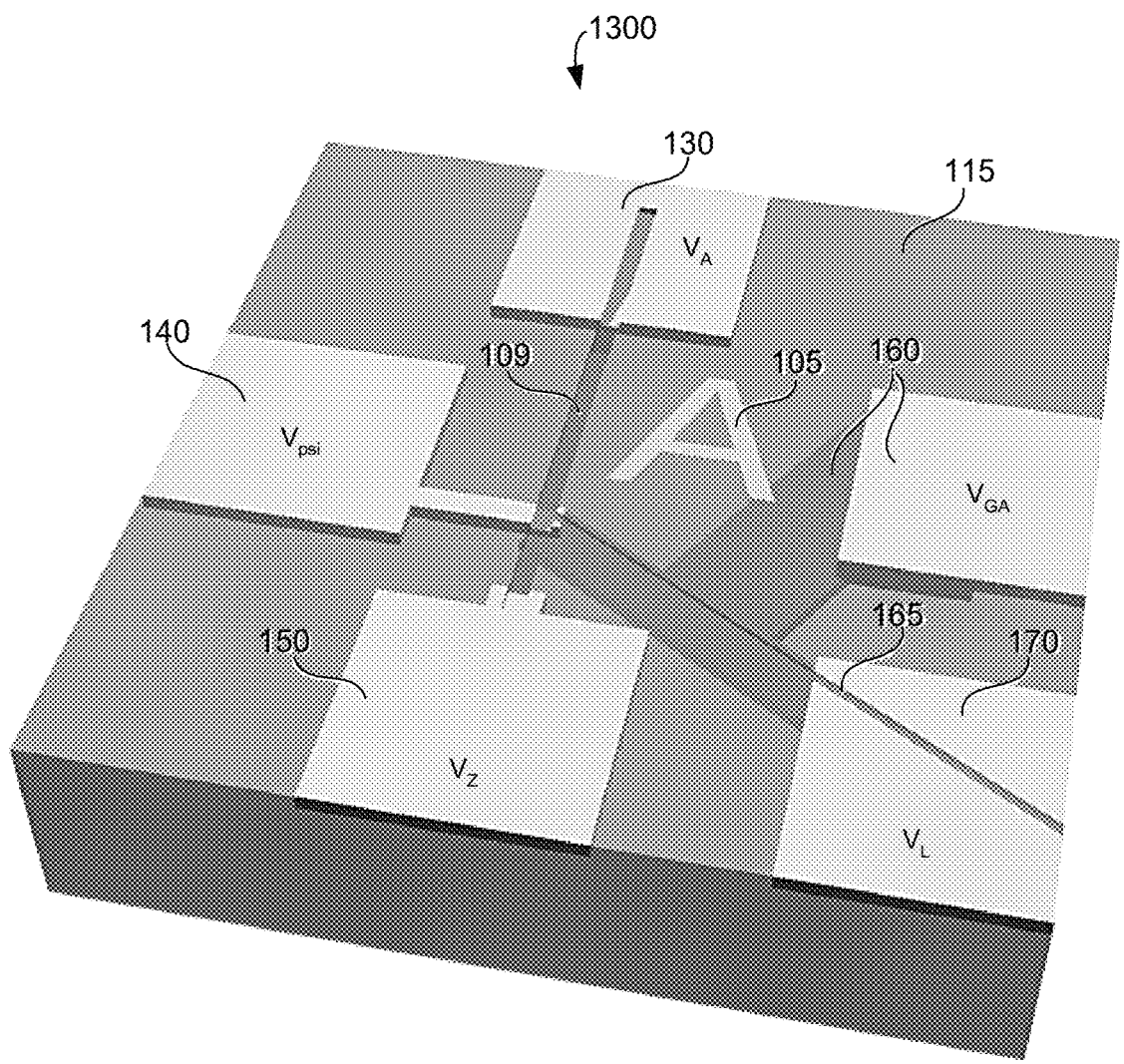
FIG. 13a is a 3D model/rendering of a silicon substrate fabricated as a jig for assembling a bifurcated conscious-gate transistor and which also shows an optional reference character/symbol which might be used as an address or coordinate specifier.

FIG. 13*a* is a 3D model/rendering of a silicon substrate fabricated as a jig for assembling a bifurcated conscious-gate transistor and which also shows an optional reference character/symbol which might be used as an address or coordinate specifier. FIG. 13*a* is a computer-generated 3D model 1300 showing silicon substrate 115 with combination contact and pads for transistor 100 (FIG. 1*a*), $V_{psi}$ 140, $V_Z$ 150, $V_L$ 170, $V_{GA}$ 160, and $V_A$ 130. Also shown is a jig etched into substrate 115, which is used to assemble transistor 100. The jig includes a trench 109 for the trunk to lay in and a trench 165 for the "L" to lay in. Trench 109 is etched deep enough and wide enough so that the center axis of the trunk is flush with the surface of the substrate 115. Trench 165 is etched deep enough and wide enough such that the center axis of the "L" is flush with the surface of the substrate 115. Ideally, there should be just a little excess width of both 109 and 165 to make it easier to manipulate the carbon nanotubes into them after depositing them onto the substrate 115. For semiconducting "L"s, a back-gate (or side-gate) 160 is necessary, which can be applied utilizing an ion-beam.

Additionally, a symbol or character 105 is either etched or added to the substrate. In some applications, this symbol can be employed as a sort of psychic marker, making a specific device easier to find or home in on by electrons.

Finally, note the angle or aspect ratio of the "L" trench 165 in relation to trunk trench 109. In this instance, it is angled 30 degrees from perpendicular to trunk trench 109. One reason for this is because it is desired to actually penetrate the trunk 110 such that the entire tip of "L" 120 resides internal to trunk 110. Coming in at an angle makes one side of the tip of "L" more like a sharp scoop rather than a blunt end of a telephone pole, as would be the case if it was attempted to penetrate perpendicular to the trunk.

Another reason for penetrating at this 30 degrees from perpendicular angle, is that it is desirable to have an electron scooper/flange inside the trunk. This is because electron flow through the CNT is ballistic (depending on current density) and, as such, they would have a tendency to fly right by the "L" exit, absent a scooper or on-ramp to exit onto.

Figure 13B:
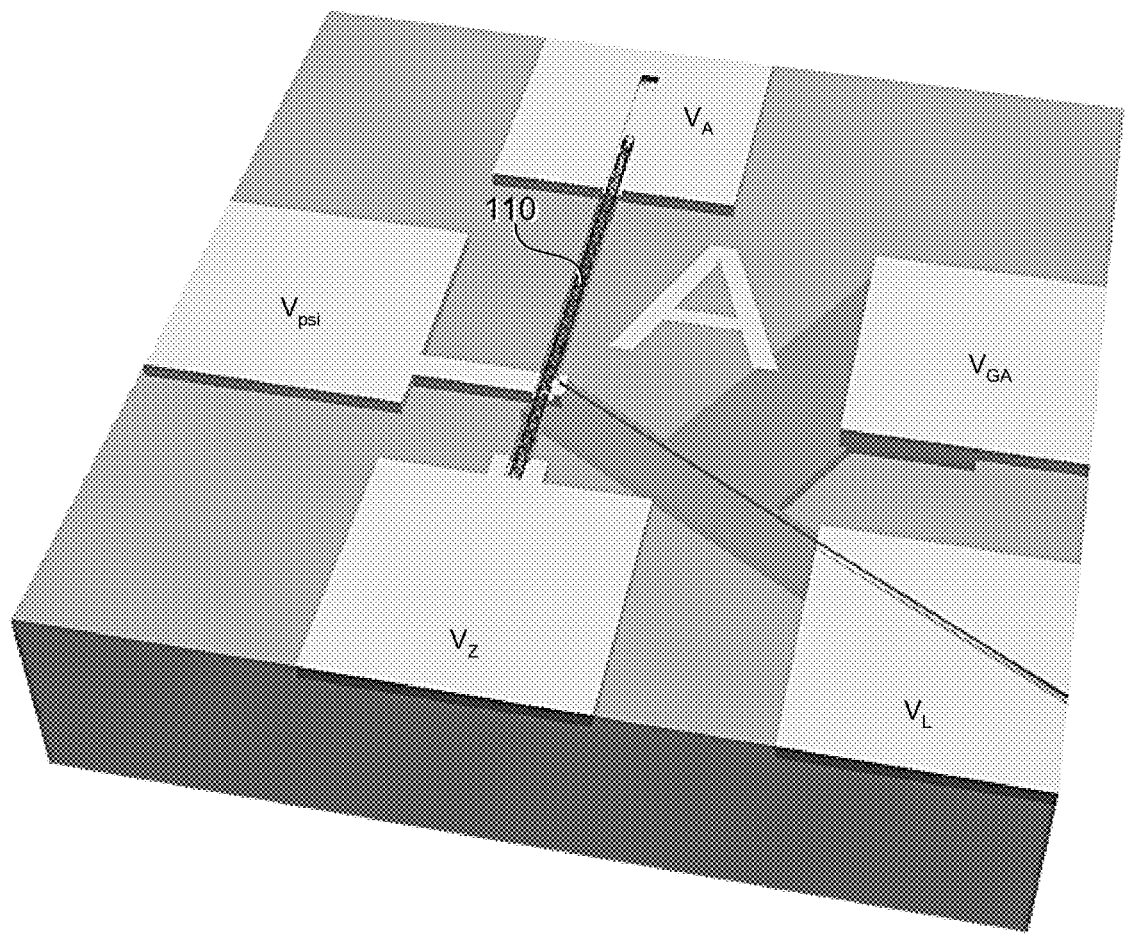
FIG. 13b is the 3D model/rendering of FIG. 13a showing how the substrate is employed as a jig, but with a "trunk" carbon nanotube laid in place as a first step in the assembly process.

FIG. 13*b* is the 3D model/rendering of FIG. 13*a* showing how the substrate is employed as a jig, but with a "trunk" carbon nanotube laid in place as a first step in the assembly process. FIG. 13*b* is a computer-generated 3D model showing trunk 110 after manipulation using either an AFM or DEP so that it is positioned inside its respective trench 109 as a first step in the assembly process.

Figure 13C:
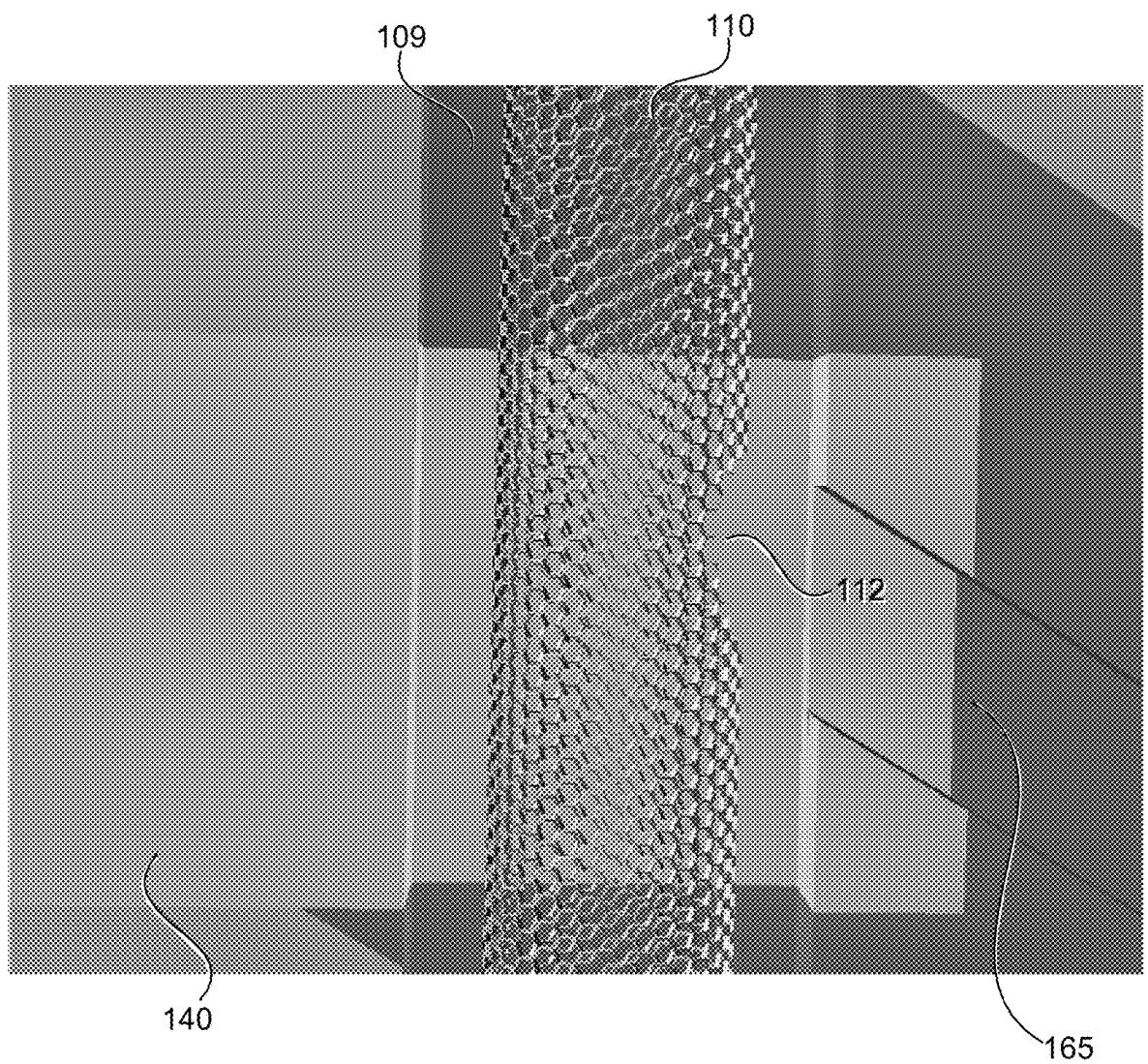
FIG. 13c is the 3D model/rendering of FIG. 13b, zoomed-in over the location where, using the e-beam of a Transmission Electron Microscope (TEM), the trunk carbon nanotube is modified to accept insertion of one end of a smaller diameter carbon nanotube or DNA strand to form the "L" of the bifurcated conscious-gate transistor and also showing the etched jig trenches where the carbon nanotubes and/or DNA strand will eventually rest.

FIG. 13*c* is the 3D model/rendering of FIG. 13*b*, zoomed-in over the location where, using the e-beam of a Transmission Electron Microscope (TEM), the trunk carbon nanotube is modified to accept insertion of one end of a smaller diameter carbon nanotube or DNA strand to form the "L" of the bifurcated conscious-gate transistor and also showing the etched jig trenches where the carbon nanotubes and/or DNA strand will eventually rest. FIG. 13*c* is a computer-generated 3D model showing an overhead view of trunk 110 and an orifice 112 created with a Transmission Electron Microscope (TEM) e-beam at the intersection of the trunk trench 109 and "L" trench 165 as a second assembly step. Vpsi tap contact 140 is optional.

Figure 13D:
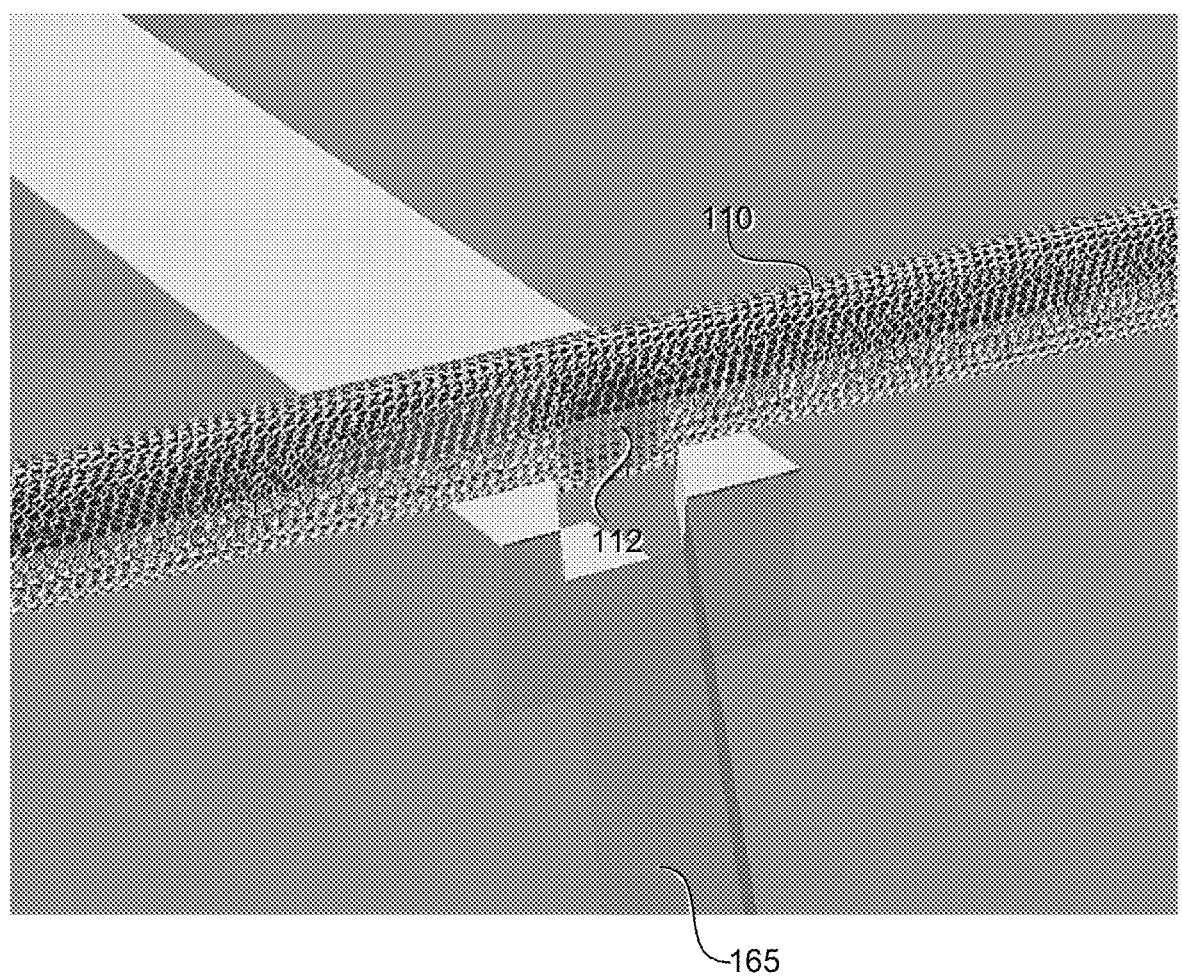
FIG. 13d is similar to FIG. 13c, but viewed from a different angle to show the orifice created in the side of the trunk carbon nanotube where the "L" will be inserted during assembly.

FIG. 13*d* is similar to FIG. 13*c*, but viewed from a different angle to show the orifice created in the side of the trunk carbon nanotube where the "L" will be inserted during assembly.

Figure 13E:
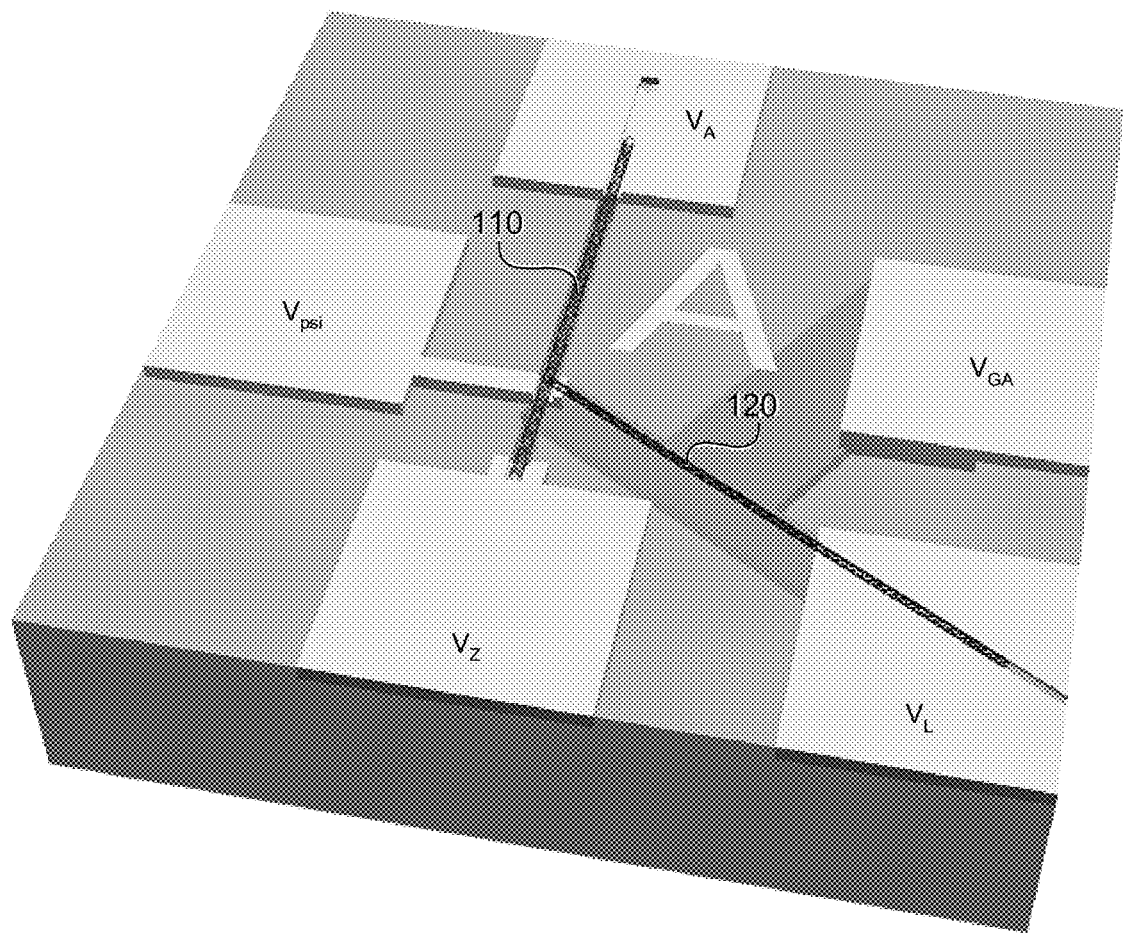
FIG. 13e is similar to FIG. 13b, except showing both the trunk carbon nanotube and the "L" carbon nanotube laid in place and positioned within their respective trenches of the assembly jig in the silicon substrate.

FIG. 13*e* is similar to FIG. 13*b*, except showing both the trunk carbon nanotube and the "L" carbon nanotube laid in place and positioned within their respective trenches of the assembly jig in the silicon substrate. FIG. 13*e* is a computer-generated 3D model showing a view of trunk 110 and an orifice 112 created with a TEM e-beam at the intersection of the trunk trench 109 and "L" trench 165 as a second step. Also shown is the "L" CNT 120 after being manipulated and positioned into its respective trench as a third step in the assembly process.

Figure 13F:
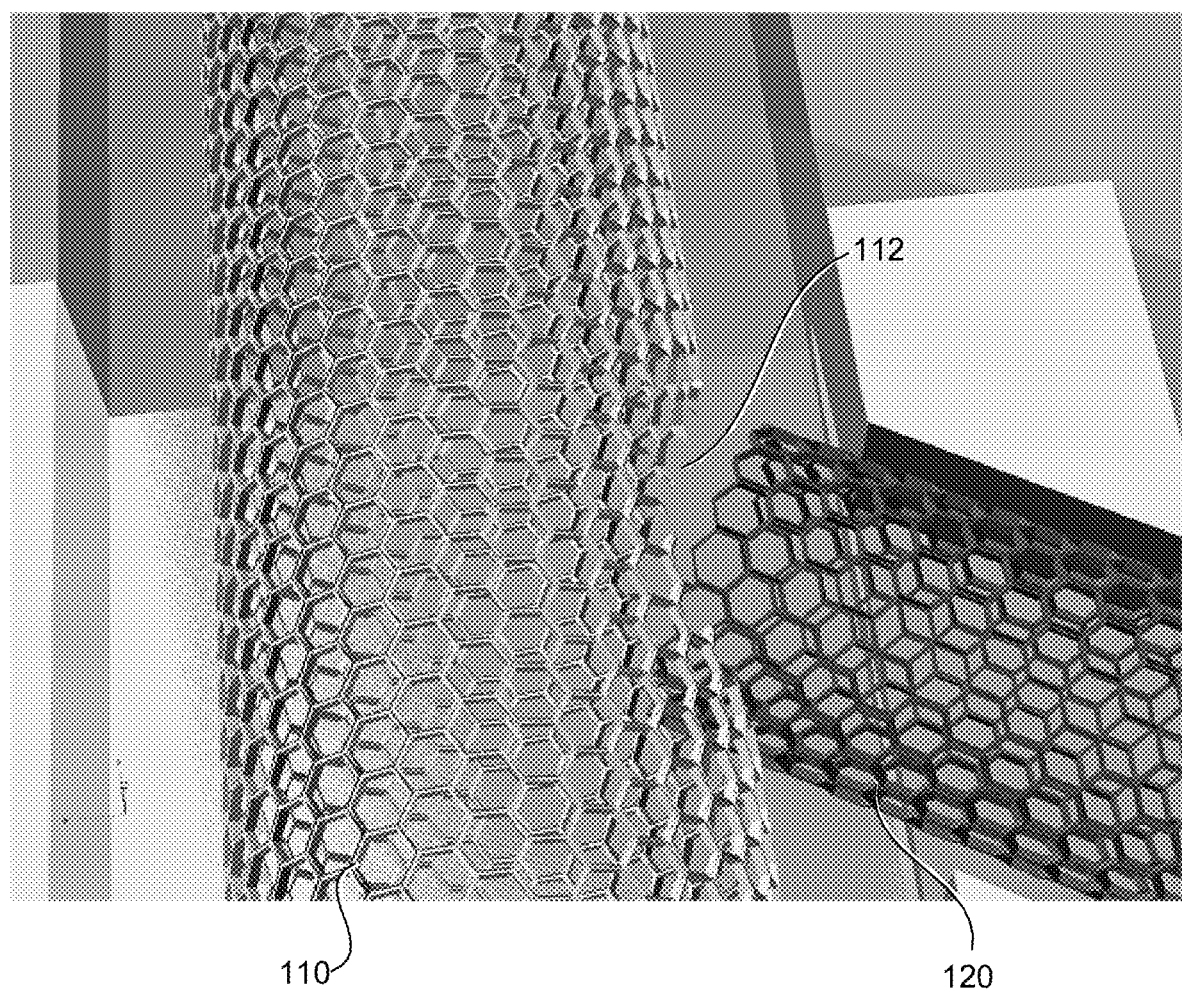
FIG. 13f is a 3D rendering showing a trunk metallic carbon nanotube resting in its assembly trench and the "L" semiconducting carbon nanotube resting in its assembly trench, both in position immediately prior to the business end of the "L" being inserted into the orifice of the trunk created by TEM e-beam.

FIG. 13*f* is a 3D rendering showing a trunk metallic carbon nanotube resting in its assembly trench and the "L" semiconducting carbon nanotube resting in its assembly trench, both in position immediately prior to the business end of the "L" being inserted into the orifice of the trunk created by a TEM e-beam. FIG. 13*f* is similar to FIG. 13*e*, except from a much closer perspective. Note that at this point, trunk 110 has not yet been penetrated by "L" 120.

Here, it can be seen how the jig etched into the substrate can be used to properly align the two components to facilitate complete penetration.

Figure 13G:
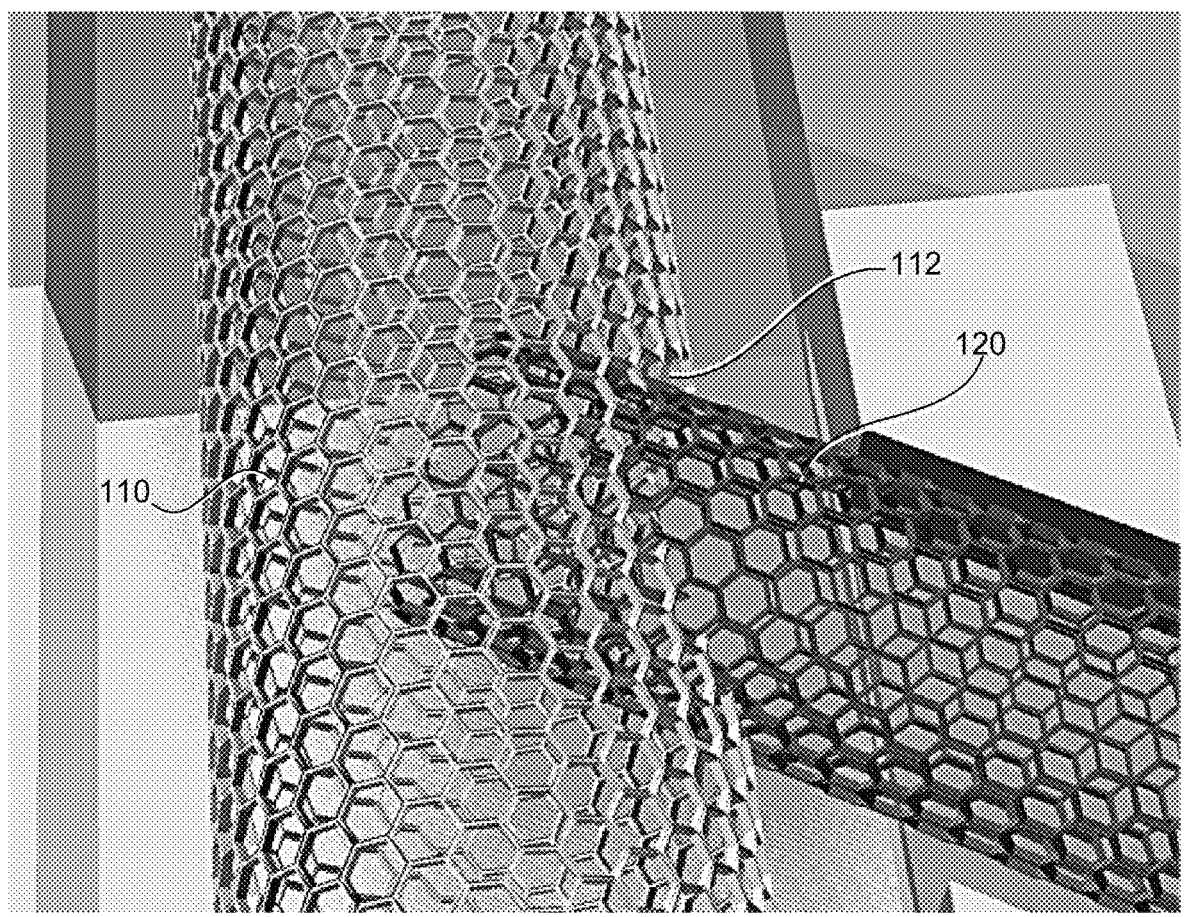
FIG. 13g is similar to FIG. 13f, except showing the conscious junction forming the conscious-gate transistor after insertion of the "L" into the trunk.

FIG. 13g is similar to FIG. 13f, except showing the conscious junction forming the conscious-gate transistor after insertion of the "L" into the trunk. FIG. 13g is similar to FIG. 13f, except as the fourth step in the assembly process, the "L" 120 has been made to completely penetrate the trunk 110 via orifice 112, wherein its respective trench 165 is employed as a skid or chute and such manipulation being done with an AFM or HEP to slide "L" 120 into the trunk orifice 112 so that the tip of "L" 120 penetrates the orifice 112 so that the tip is completely inside trunk 110.

Figure 13H:
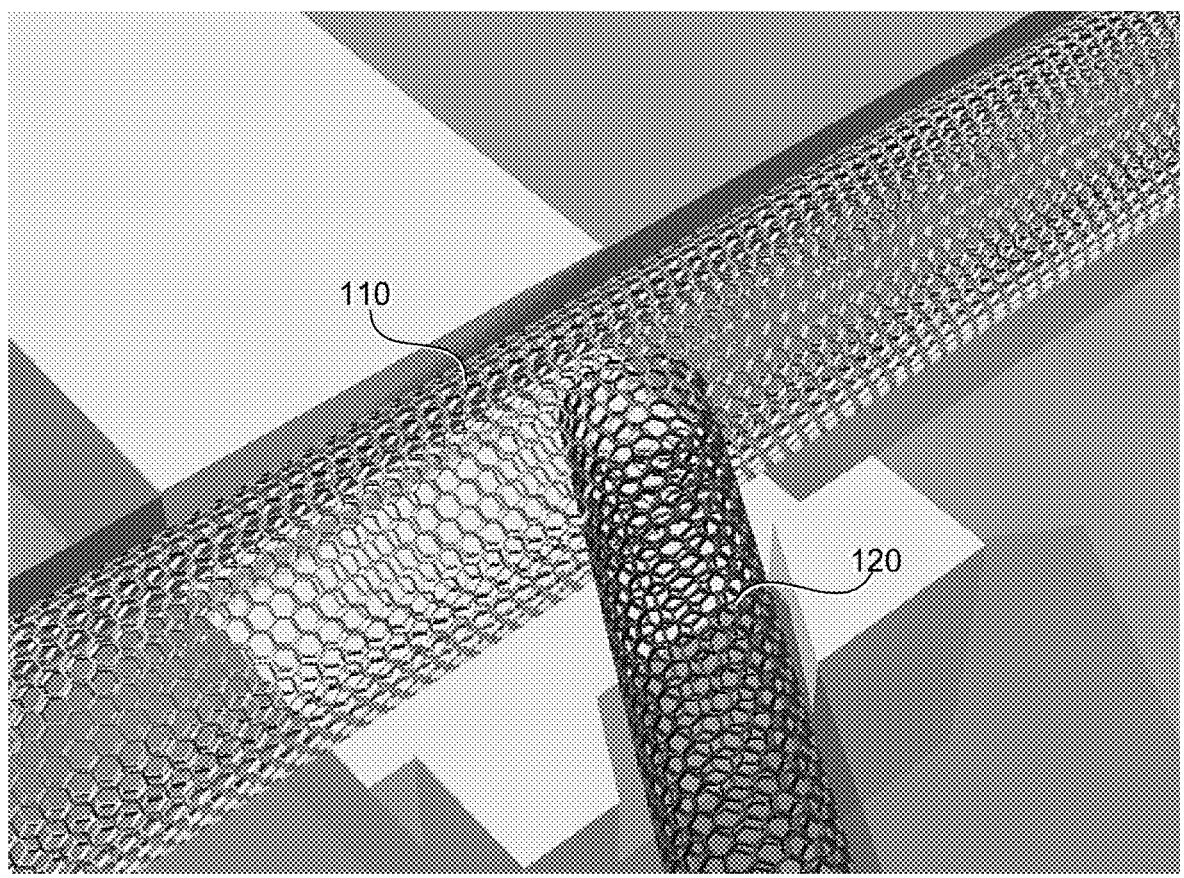
FIG. 13h is similar to FIG. 13g, except viewed from a different perspective.

FIG. 13h is similar to FIG. 13g, except viewed from a different perspective.

At this point, as an optional fifth step in the assembly process, top contacts may be deposited on top of each bottom contact described previously. Ideally, the contacts should be symmetric, meaning that all contacts are made of the same material.

Figure 13I:
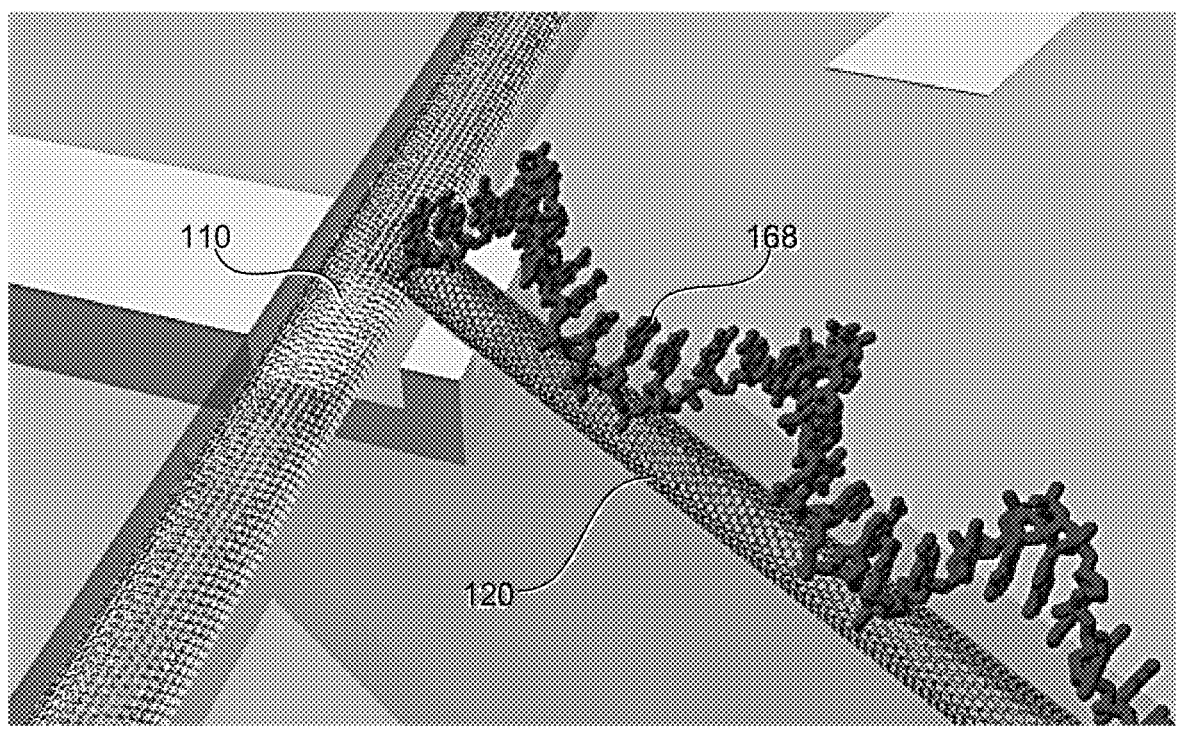
FIG. 13i is similar to FIG. 13f, except viewed from a wider perspective and also showing the "L" carbon nanotube after being decorated with single-strand DNA.

FIG. 13i is similar to FIG. 13f, except viewed from a wider perspective and also showing the "L" carbon nanotube after being decorated with dsDNA or ssDNA. FIG. 13i shows optional decoration of "L" 120 with ssDNA 419 as an optional sixth step in the assembly process. To hold the entire assembly in place, vapor deposition similar to a non-reactive epoxy may be utilized, especially if the deposition could be achieved at a relatively low temperature for vapor deposition. This would avoid possible chemical reactions and, consequently, undesired modification of the electrical properties of the components.

Figure 13J:
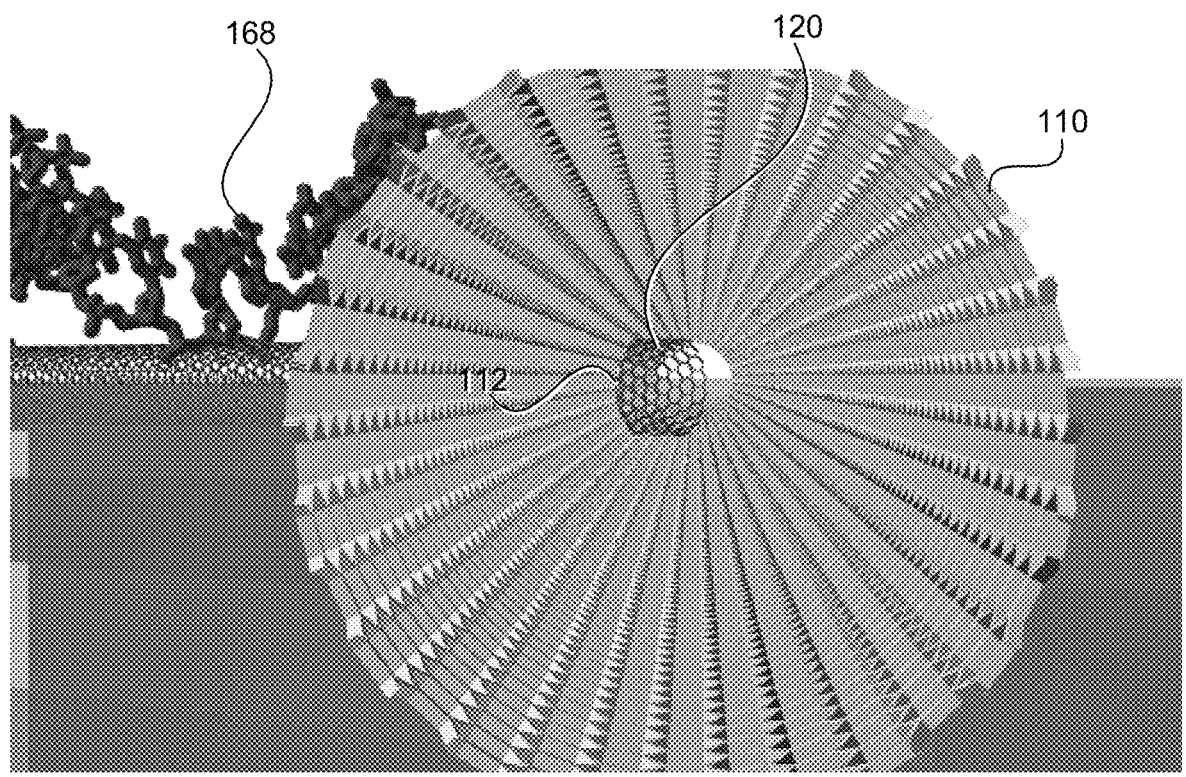
FIG. 13j is similar to FIG. 13i, except with a view down the interior of the trunk carbon nanotube.

FIG. 13j is similar to FIG. 13i, except with a view down the interior of the trunk carbon nanotube 110. Note the electron "scooper"/exit ramp formed by the tip of "L"120. As can be seen from this perspective, it is likely that not all electrons in the left or center lane of traffic are going to be successful at getting onto the exit ramp and will either tunnel through, giving up energy, and/or cause a carbon atom there to emit a photon as a result of a head-on collision with subject electron. Electrons in the far right, top, and bottom lanes will most likely quietly pass right on by the exit ramp, unless they are carrying instructions to do otherwise. In other words, the scooper used as an exit ramp helps the electrons carry out their instructions.

Figure 13K:
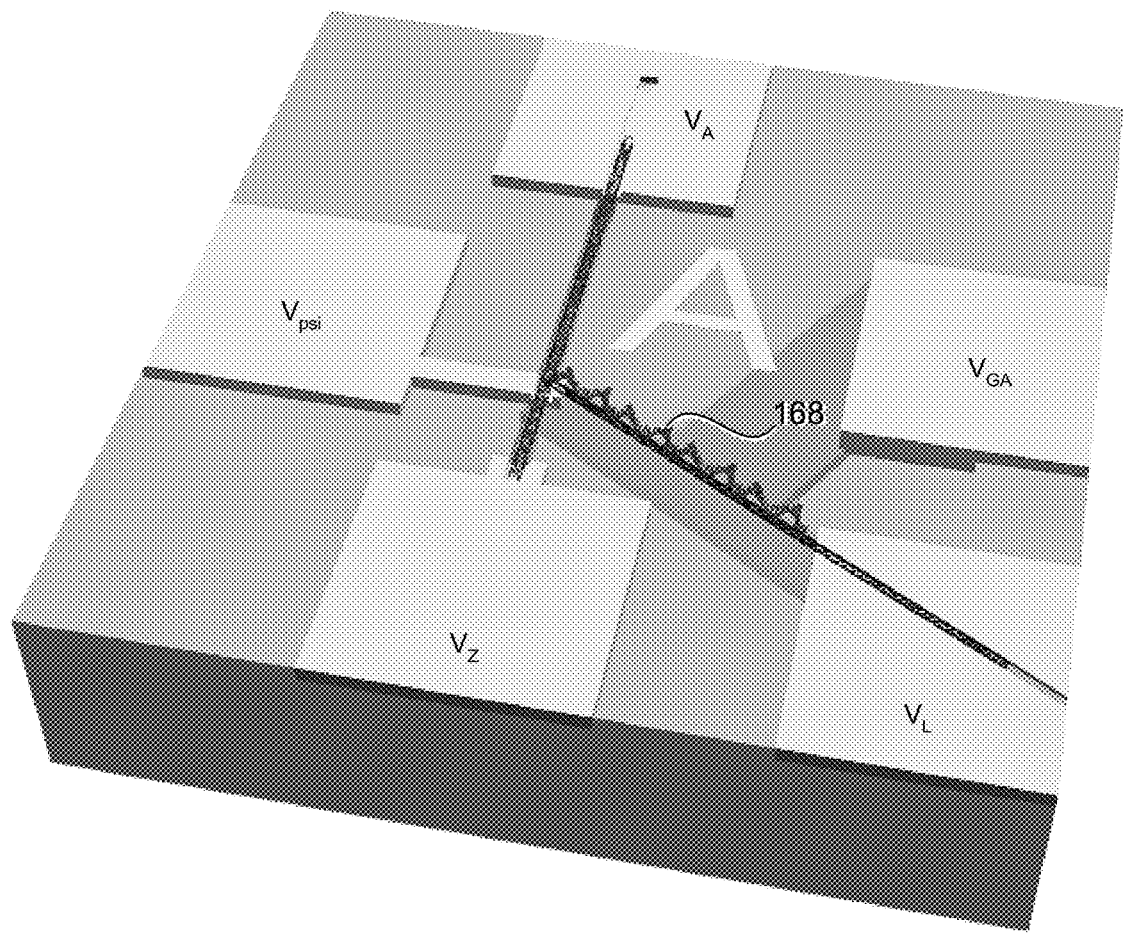
FIG. 13k is similar to FIG. 1, except this time viewed from a wider perspective.
Figure 13I:
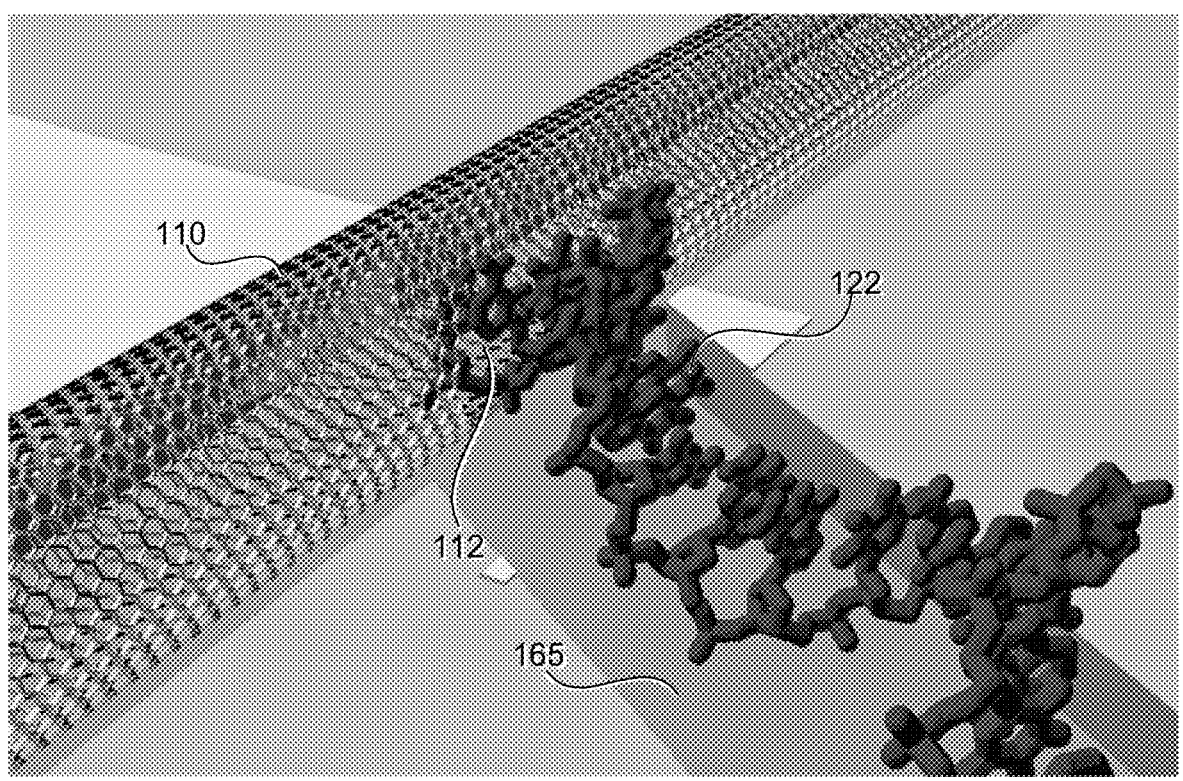

FIG. 13k is similar to FIG. 13i, except viewed from a wider perspective.

FIG. 13l is similar to FIG. 13i, except it is showing single-stranded DNA alone being employed as the "L", the ssDNA optionally being impregnated with silver and/or nickel nanoparticles. FIG. 13l is similar to FIG. 13h, except that, to form the "L" 120 of transistor 100, a segment of ssDNA 419 has been substituted for the carbon nanotube. The ssDNA 419 forming "L" 120 can be stand-alone or can be impregnated with, for example, silver and/or nickel nanoparticles.

Figure 13M:
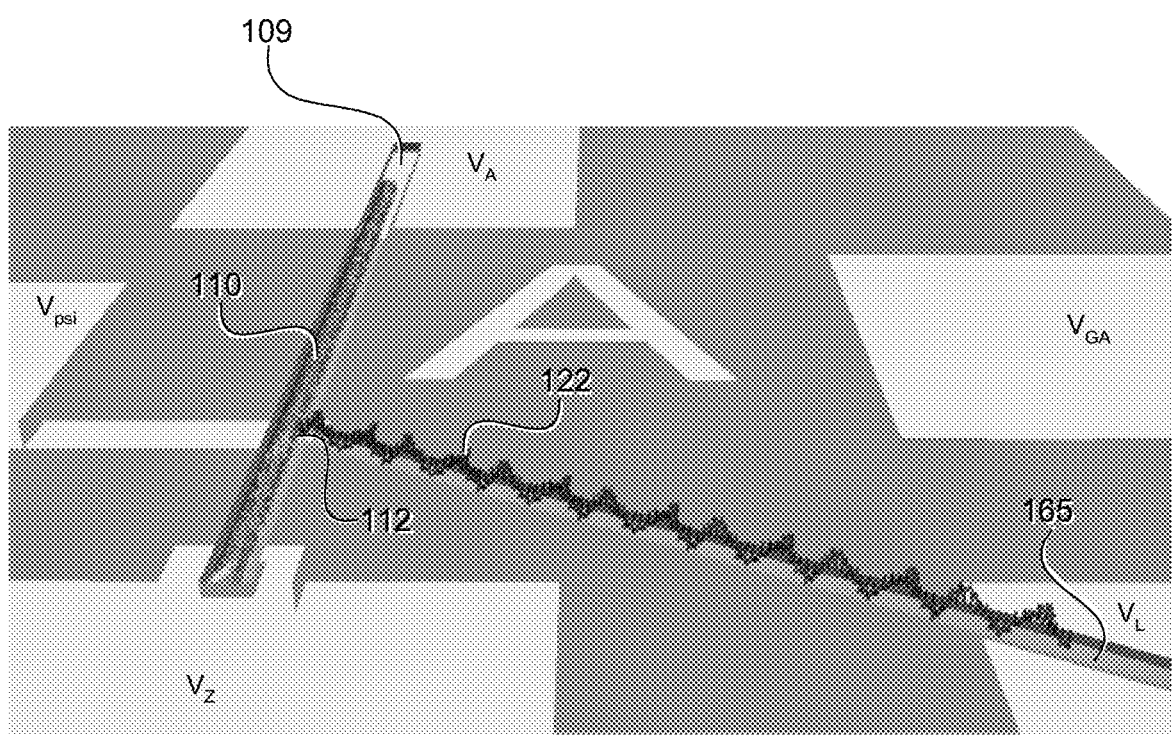
FIG. 13m is similar to FIG. 13l, except viewed from a wider perspective.

FIG. 13m is similar to FIG. 13l, except viewed from a wider perspective.

Figure 14A:
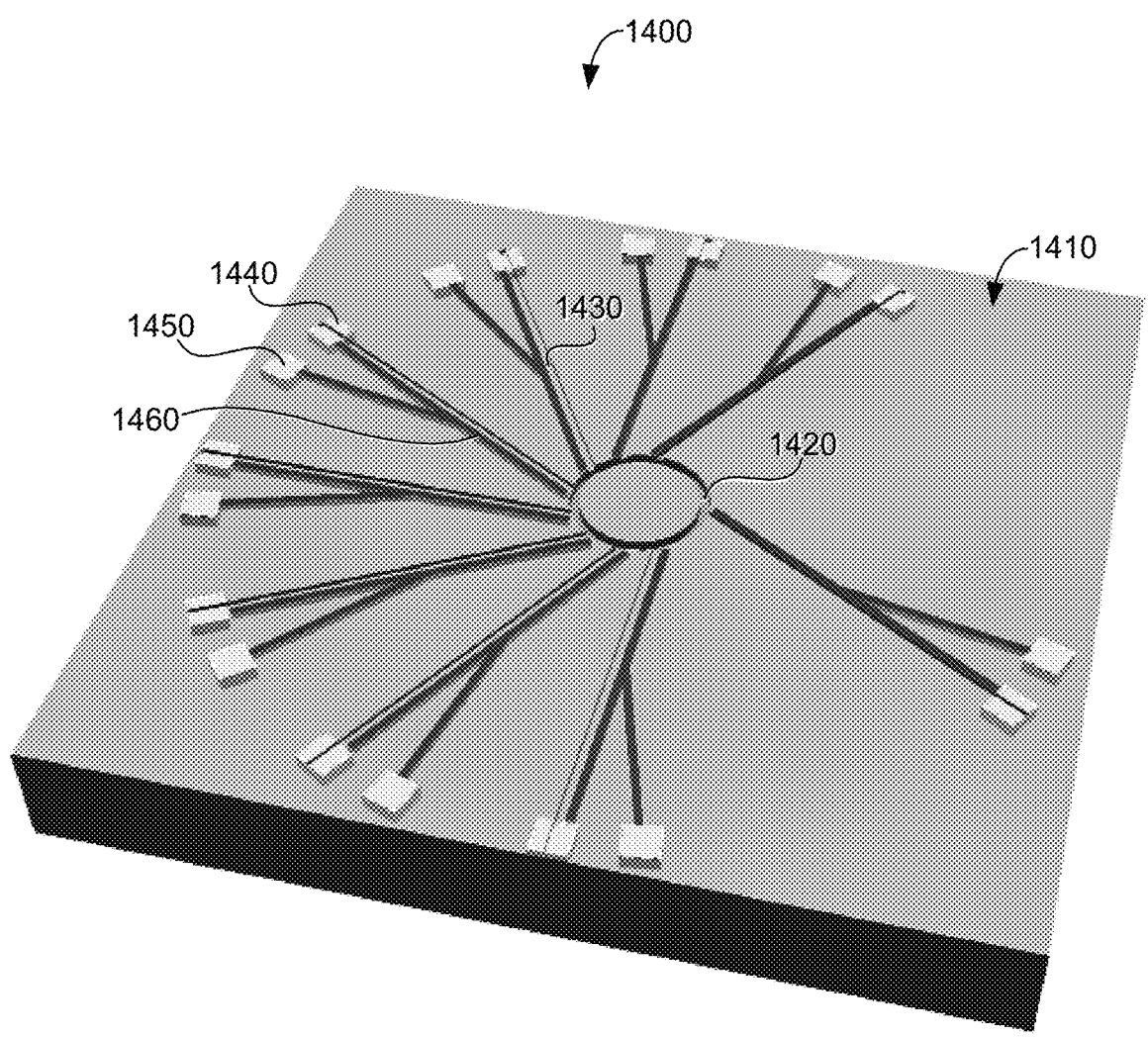
FIG. 14a is a 3D model/rendering showing the trenches forming an assembly jig etched into a silicon substrate to ultimately be used to form a an artificial conscious-gate multiplexer/neuron ("psyclotron") built from a carbon nanotorus and carbon nanotubes.

FIG. 14a is a 3D model/rendering showing the trenches forming an assembly jig etched into a silicon substrate to ultimately be used to form an artificial conscious-gate multiplexer/neuron ("psyclotron") built from a carbon nanotorus and carbon nanotubes. FIG. 14a illustrates a computer-generated 3D model 1400 showing silicon substrate 1410 with a jig for assembling an eight-dendrite psyclotron etched into the substrate in the same manner as for transistor 100 substrate 1300 (FIG. 13a). In this embodiment, there are nine "L" trenches 1430 (one for each dendrite "L" and one axion "L") where the "L"s will rest and one ring trench 1420 where the carbon nanotorus will rest. Substrate 1410 also includes a combination contact/pad 1440 and gate/field pad 1450 for all nine corresponding gate/fields 1460. If the "L" CNTs are all metallic, the gate/field pad 1450 and the corresponding gate/fields 1460 are not necessary. Likewise, if the carbon nanotorus to be used is semiconducting rather than metallic, a back or side-gate and corresponding pad must be added.

Figure 14B:
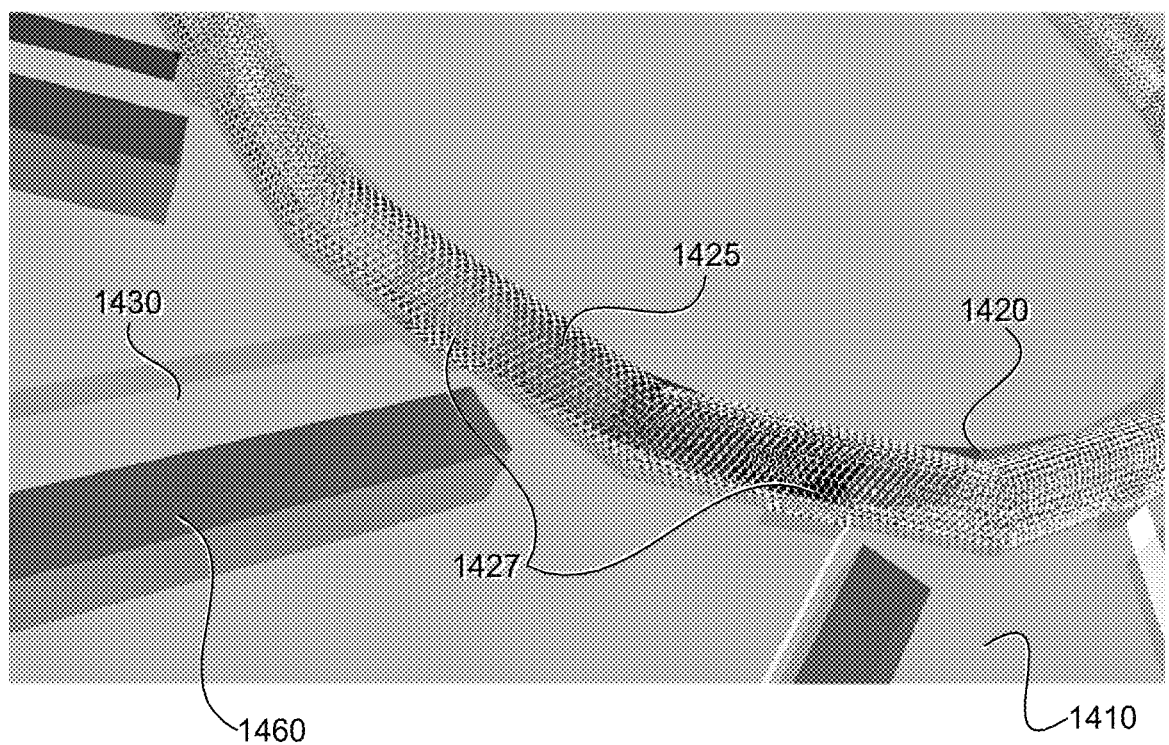
FIG. 14b is similar to FIG. 14a, except also showing the psyclotron's carbon nanotorus resting in its trench and subsequently modified by TEM e-beam to create the orifices the "L" carbon nanotubes or DNA wires will be inserted into during assembly.

FIG. 14b is similar to FIG. 14a, except also showing the psyclotron's carbon nanotorus resting in its trench and subsequently modified by a TEM e-beam to create the orifices the "L" carbon nanotubes or DNA wires will be inserted into during assembly.

Figure 14C:
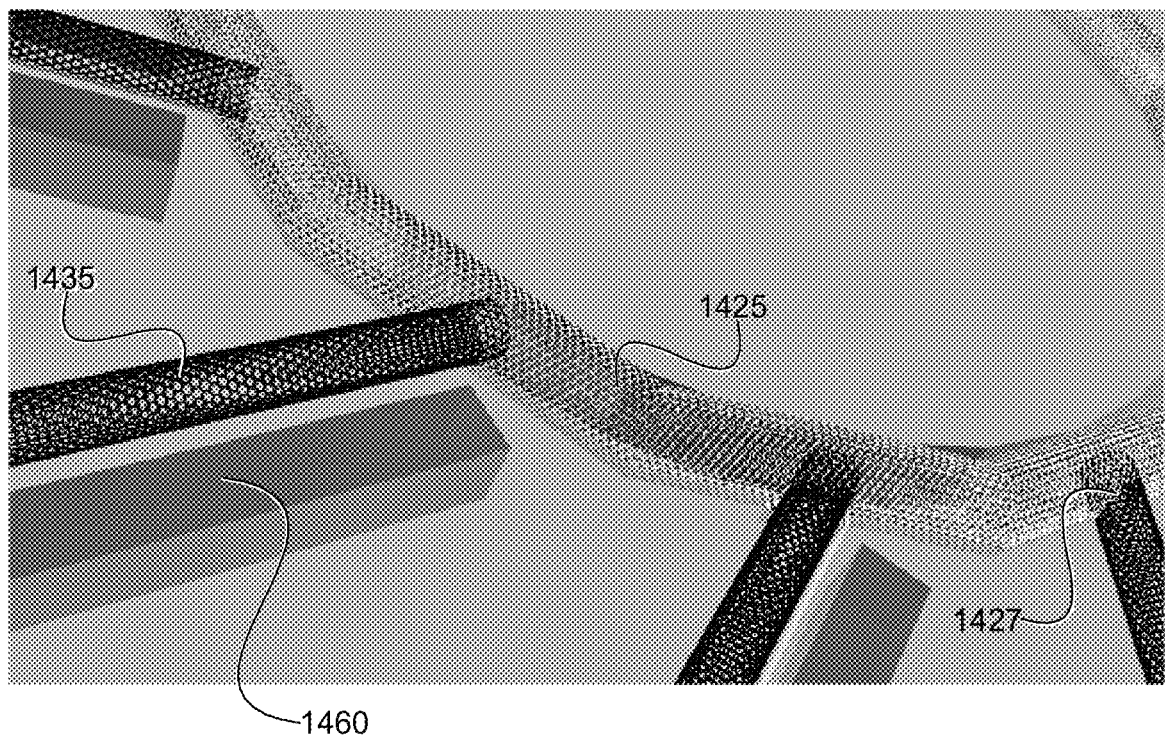
FIG. 14c is similar to 14b, except showing the "L" carbon nanotubes after insertion into their respective orifices.

FIG. 14c is similar to 14b, except showing the "L" carbon nanotubes after insertion into their respective orifices. FIG. 14b is a closer-in perspective of FIG. 14a showing a metallic nanotorus 1425 after being positioned into its jig trench 1420 as a first step in the psyclotron assembly process. Also shown are the orifices 1427 created by e-beam in the side-wall of 1425 at each "L"—nanotorus trench intersection of substrate 1410.

FIG. 14c is similar to 14b, except showing the "L" carbon nanotubes after insertion into their respective orifices. FIG. 14c shows the "L" CNTs 1435 after being manipulated into their respective jig trenches and subsequently coaxed by way of AFM or DEP to completely penetrate, via their respective orifices 1427, the nanotorus 1425 side-wall. Also shown are the respective optional side-gates 1460, which, in this instance, indicate that the "L" CNTs are semiconducting.

Figure 14D:
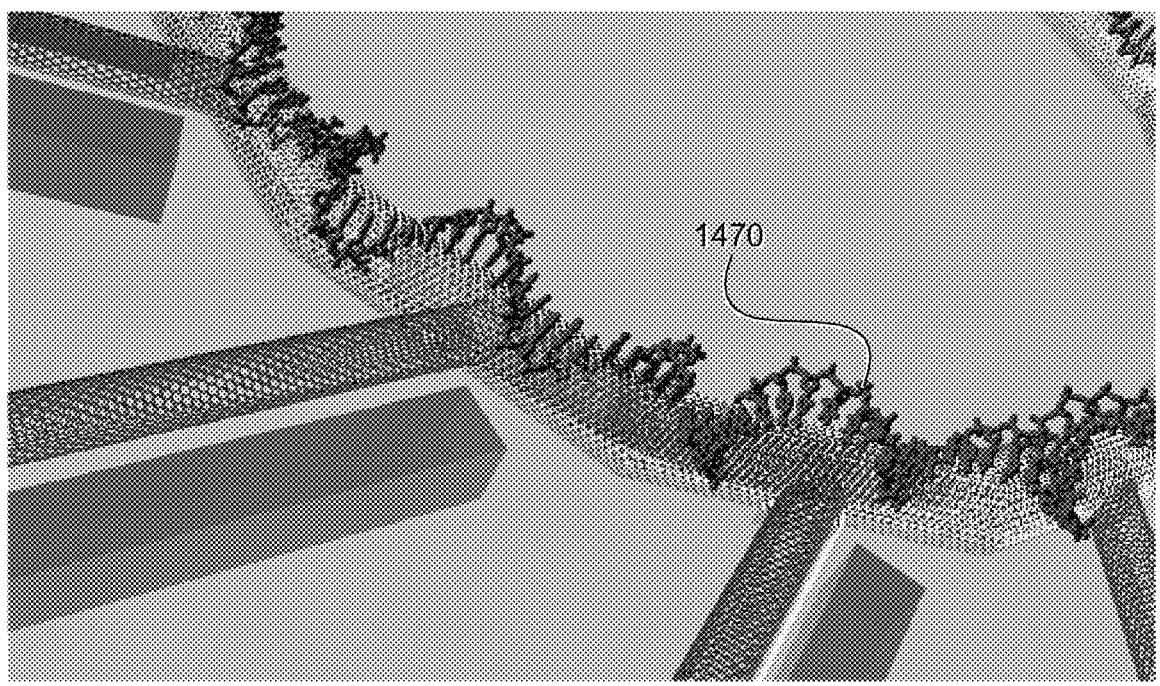
FIG. 14d is similar to FIG. 14c, except showing the psyclotron after being decorated with single-strand DNA.

FIG. 14d is similar to FIG. 14c, except showing the psyclotron after being decorated with single-strand DNA. FIG. 14d is a top view of carbon nanotorus 1425 after optional decoration with ssDNA segment 1470.

Figure 14E:
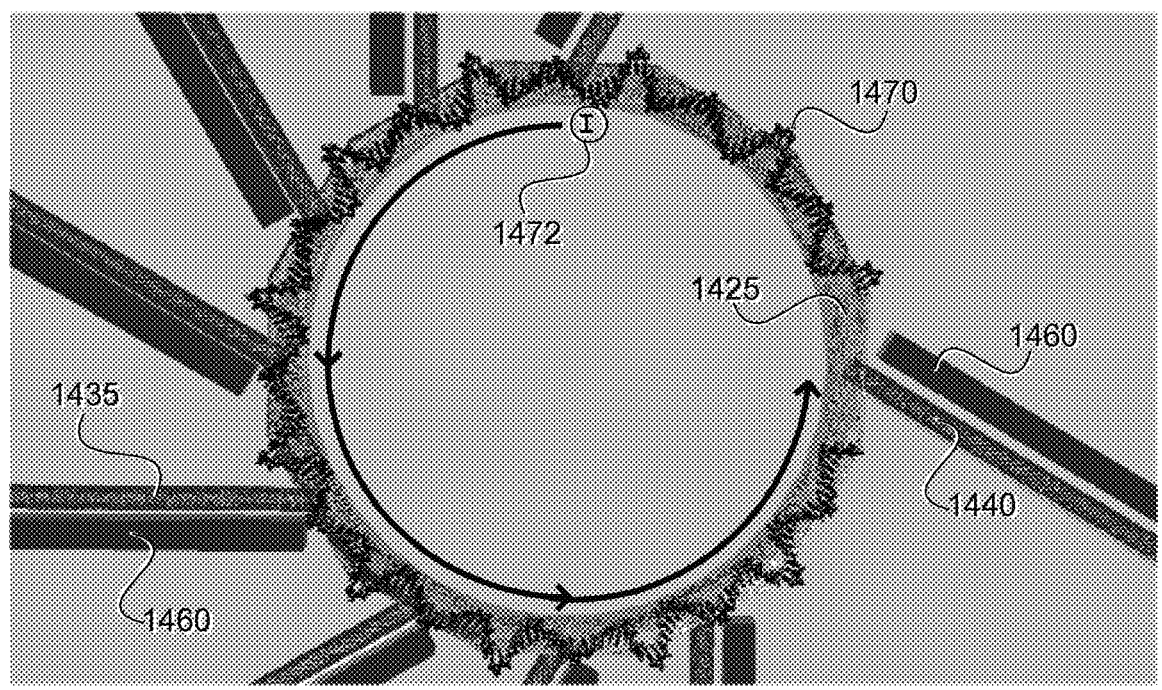
FIG. 14e is similar to FIG. 14d, except from an overhead view showing the aspect angles of the "L" dendrite nanotubes in relation to the aspect angle of the "L" axion nanotube and also showing current flow direction when the "L" dendrites are functioning as inputs, with the "L" axion functioning as an output or vice-versa.

FIG. 14e is similar to FIG. 14d, except from an overhead view showing the aspect angles of the "L" dendrite nanotubes in relation to the aspect angle of the "L" axion nanotube and also showing current flow direction when the "L" dendrites are functioning as inputs, with the "L" axion functioning as an output or vice-versa. Also shown is a circular arrow showing intended direction of current flow 1472. "L" 1440 is the axion, while the other "L"s are dendrites. Side-gate 1460 is the side-gate for axion CNT 1440, indicating that axion 1440 is semiconducting. CNT "L" 1435 is a dendrite with corresponding side-gate 1460. Note that if current circulating as shown decides to exit, most will have to tunnel through the back side of the "scooper", similar to trying to get onto a highway on-ramp going in the wrong direction. Also note that all the "L"s are canted in the same direction 30 degrees from perpendicular of the nanotorus 1425 sidewall. In this configuration, some energy will be lost due to tunneling through the back side of the scooper and/or emission of photons from such collisions. Also note that with both dendrite "L"s and axion "L"s canted the same direction, there's really no way to tell which are inputs and which are supposed to be outputs.

Figure 14F:
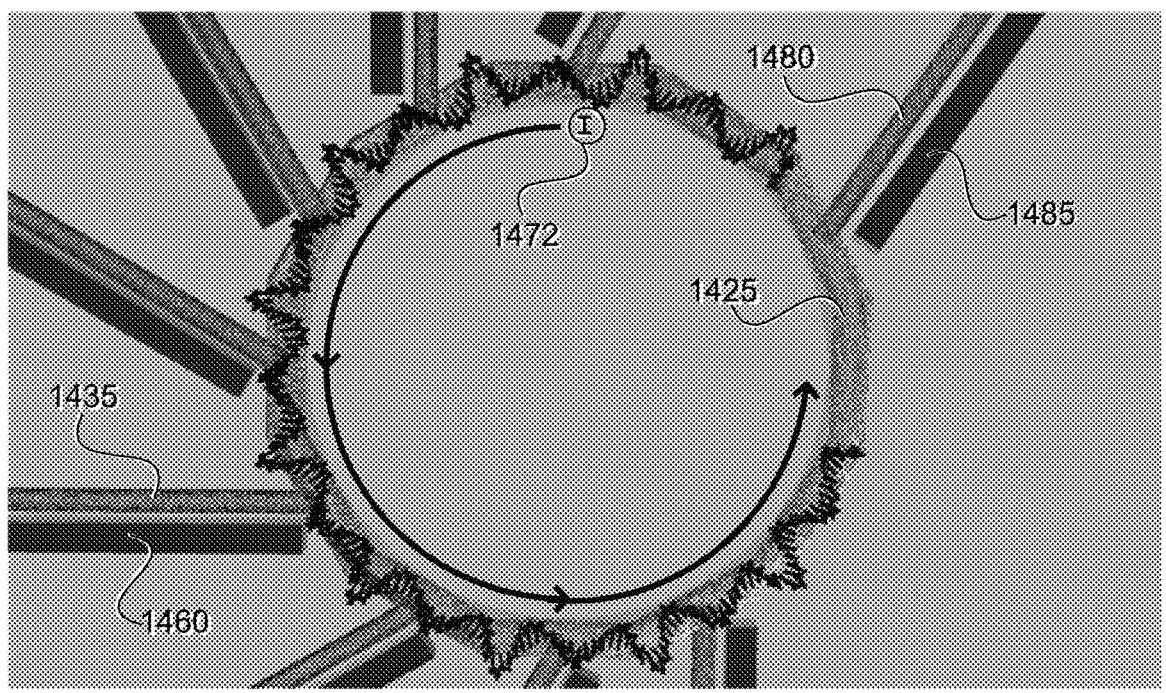
FIG. 14f is similar to FIG. 14e, except showing the "L" axion carbon nanotube at a higher position and a different aspect angle.

FIG. 14f is similar to FIG. 14e, except showing the "L" axion carbon nanotube at a higher position and a different aspect angle. FIG. 14f shows the axion "L" 1480 and its respective side-gate 1485 canted thirty degrees off perpendicular in the opposite direction of the dendrite "L"s. As such, with respect to indicated current flow direction 1472, it can be seen that in this configuration, the dendrite "L"s 1435 are inputs and axion "L" 1480 is functioning as an output.

Figure 14G:
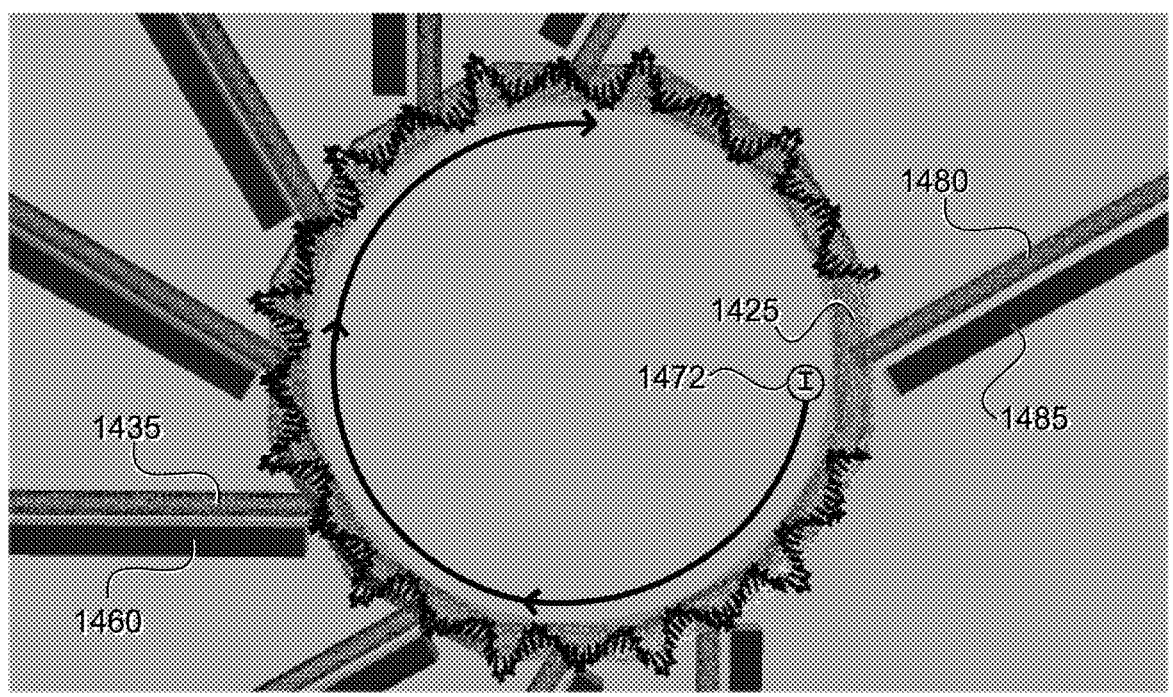
FIG. 14g is similar to FIG. 14f, except showing the "L" axion carbon nanotube at a middle position and being used as an input and the other "L" carbon nanotubes being employed as outputs as indicated by the circular arrow showing current flow direction, thereby forming a conscious-gate multiplexer/psyclotron.

FIG. 14*g* is similar to FIG. 14*f*, except showing the "L" axion carbon nanotube at a middle position and being used as an input and the other "L" carbon nanotubes being employed as outputs as indicated by the circular arrow showing current flow direction, thereby forming a conscious-gate multiplexer/psyclotron. FIG. 14*g* shows axion "L" 1480 and its respective side-gate 1485 are positioned more equidistant between the dendrite "L"s 1435. From the current flow direction indicator, it can be surmised that, at this instant, the dendrite "L"s are functioning as outputs and the axion "L" 1480 is functioning as an input, indicating that psyclotron 1400 can function bidirectionally.

Figure 15:
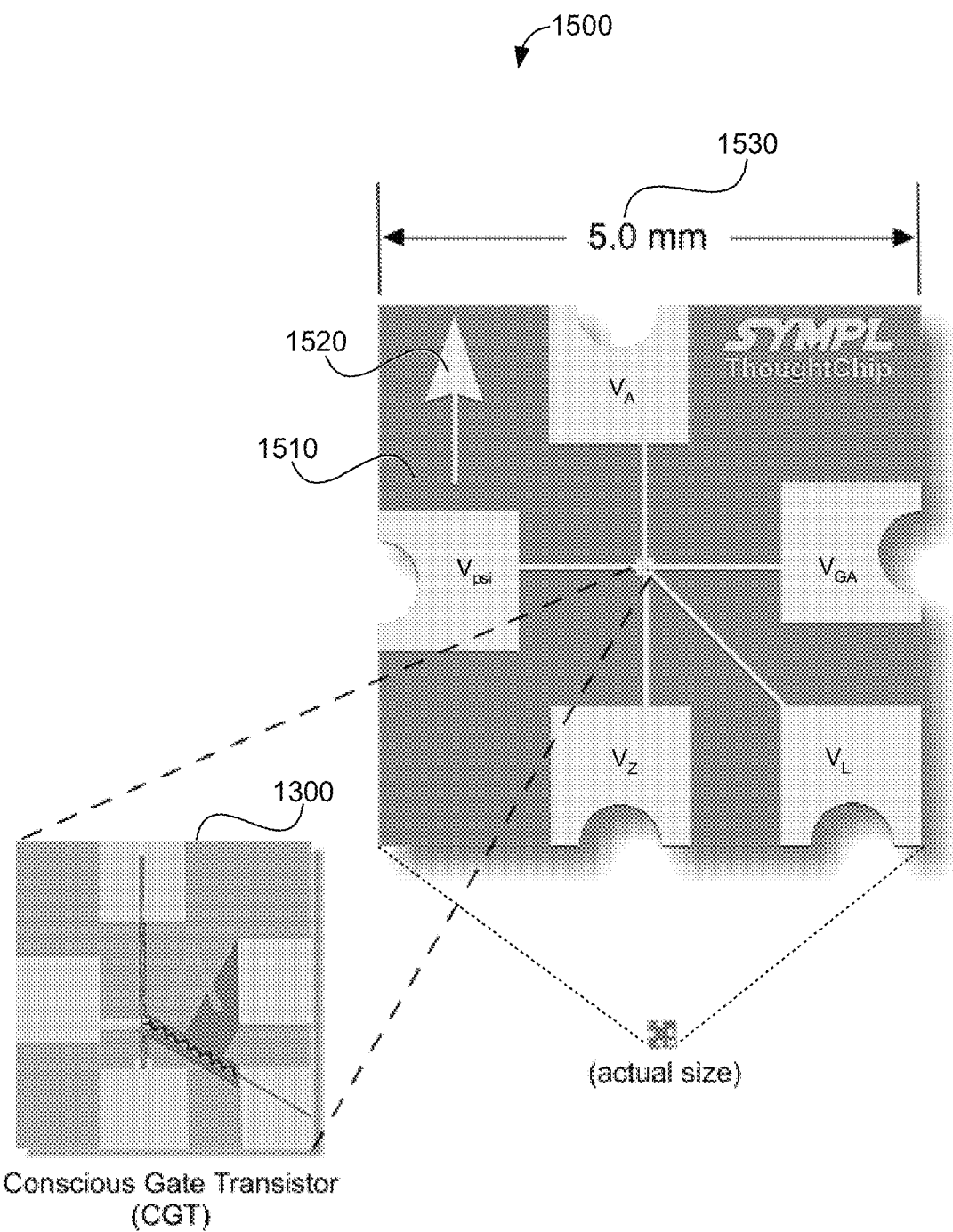
FIG. 15 is a computer rendering of a proposed carrier for mounting the conscious-gate transistor onto either before, after, or during assembly of the actual conscious-gate transistor onto its substrate/jig to form a functioning, surface-mount, "ThoughtChip", which can then be used in a conscious system/machine.

FIG. 15 is a computer rendering of a proposed carrier for mounting the conscious-gate transistor onto either before, after, or during assembly of the actual conscious-gate transistor onto its substrate/jig to form a functioning, surface-mount, "ThoughtChip" 1500, which can then be used in a conscious system/machine. A single bifurcated conscious-gate transistor die 1300, assembled or unassembled, can be mounted on the novel ThoughtChip surface-mountable chip carrier 1510. The purpose of the chip carrier is to provide something larger than a single substrate die 1300 that can be handled by humans and/or robots during the manufacturing process. For example, the chip carrier may be on the order of at least 5.0 mm on a side 1530. For a single transistor, most of the substrate would not be used, except for providing a work surface on which to place, sort, and manipulate the carbon nanotubes and nanotoroids used to form the transistor. Note the up-pointing arrow 1520 etched into the surface of the chip carrier 1510. It is used essentially for the same reasons as symbol 105 of transistor 1300, except instead of being a psychotronic address, it is for providing psychotronic vector/direction reference. It is also used during the assembly process as a reference for properly orienting the chip carrier onto a circuit board prior to permanent mounting.

Figure 16:
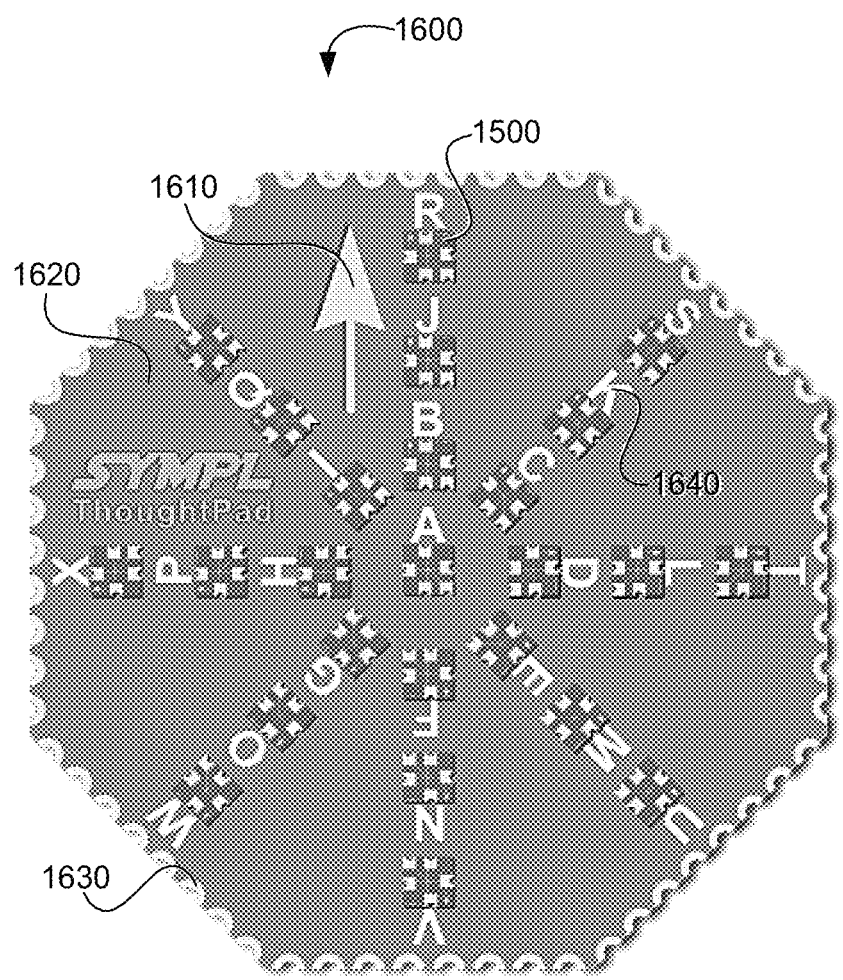
FIG. 16 is computer rendering of a proposed surface-mount "ThoughtPad" multi-chip carrier comprising an array of ThoughtChips mounted on its surface.

FIG. 16 is computer rendering of a proposed surface-mount "ThoughtPad" multi-chip carrier comprising an array of ThoughtChips mounted on its surface. The novel ThoughtPad 1600 includes multiple, radially arranged ThoughtChips 1500 mounted on a printed circuit board (PCB) 1620. Like the ThoughtChip 1500, it also has an arrow 1610 etched into its surface for the same reasons. This particular version's PCB 1620 is also surface mountable, wherein it has enough semi-circular pads 1630 to bring out all the required signals from each ThoughtChip and make them accessible to the circuit board on which it is mounted. Additionally, each of the ThoughtChips 1500 is labeled with a unique symbol 1640 for the same reasons that the substrate 115 of transistor 1300 has a symbol 105. In this example, the symbols comprise the first 25 letters of the English alphabet, capitalized.

At first glance, it would seem this arrangement would only support psychotronic control of a target machine, by way of direction and magnitude on just the X and Y axis. However, it may be possible to train an artificial neural network in an aircraft to pitch up, for example, if ThoughtChips labeled "U," "V," and "W" are simultaneously perturbed as a group, pitch down if ThoughtChips labeled "Y," "R," and "S" are simultaneously perturbed as a group, bank left if ThoughtChips labeled "W," "X," and "Y" are simultaneously perturbed as a group, and bank right if ThoughtChips labeled "S," "T," and "U" are simultaneously perturbed as a group, such that only these extreme outer ThoughtChips, when perturbed collectively as a specified group, have an effect on pitch and roll, while the others affect only yaw control, for example.

Figure 17:
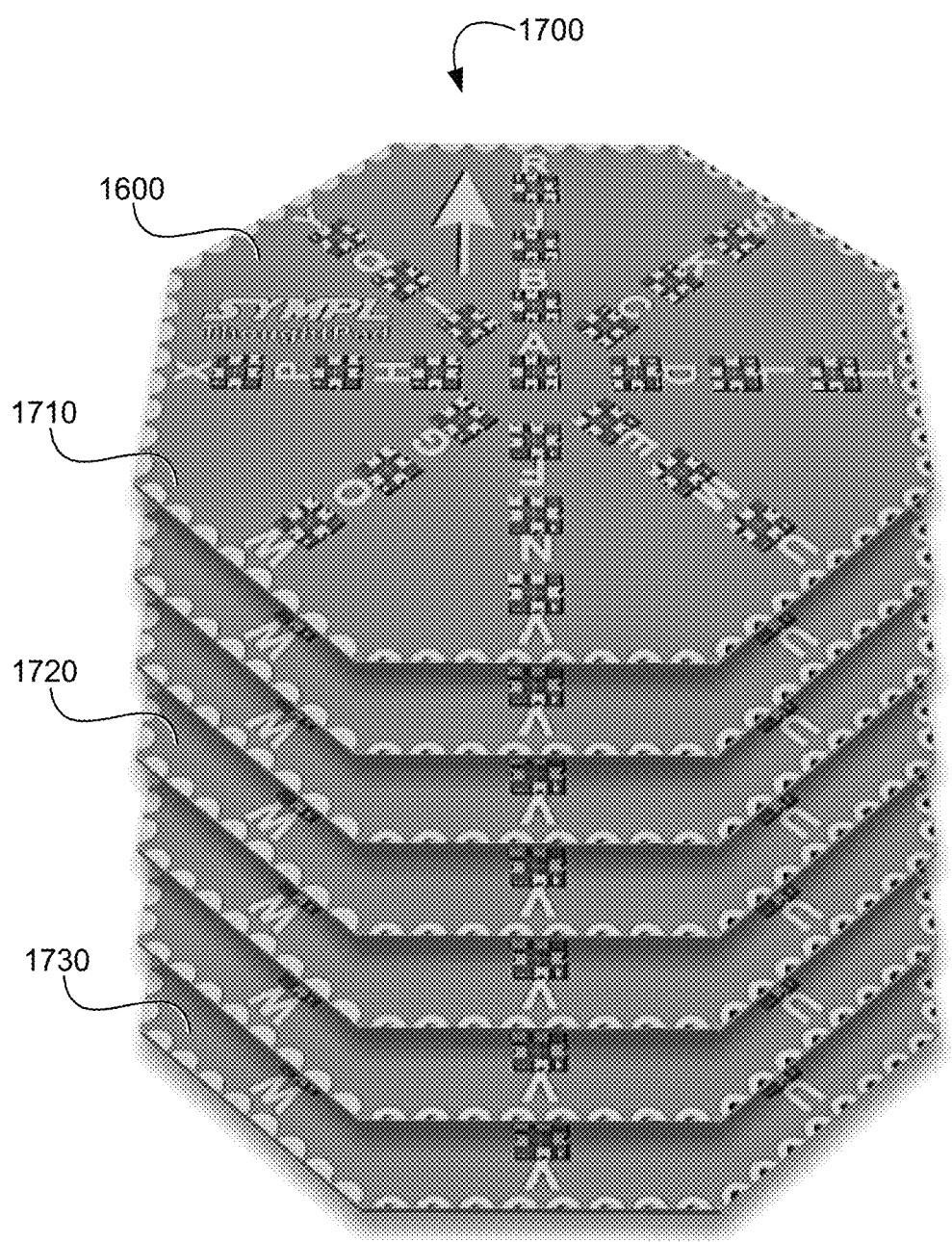
FIG. 17 is a computer rendering of a proposed "ThoughtStack" comprising multiple ThoughtPads to form a multi-dimensional thought input device for artificial neural networks and conscious machines.

FIG. 17 is a computer rendering of a proposed "Thought-Stack" comprising multiple ThoughtPads to form a multi-dimensional thought input device for artificial neural networks and conscious machines. The novel ThoughtStack 1700 includes multiple ThoughtPads 1600 stacked on top of each other to form a stack, such that there is a top Thought-Pad 1710, a middle ThoughtPad 1720, and a bottom ThoughtPad 1730. In this manner, a percipient has a means to impose a volition to move in 3D space and at various magnitudes.

Figure 18:
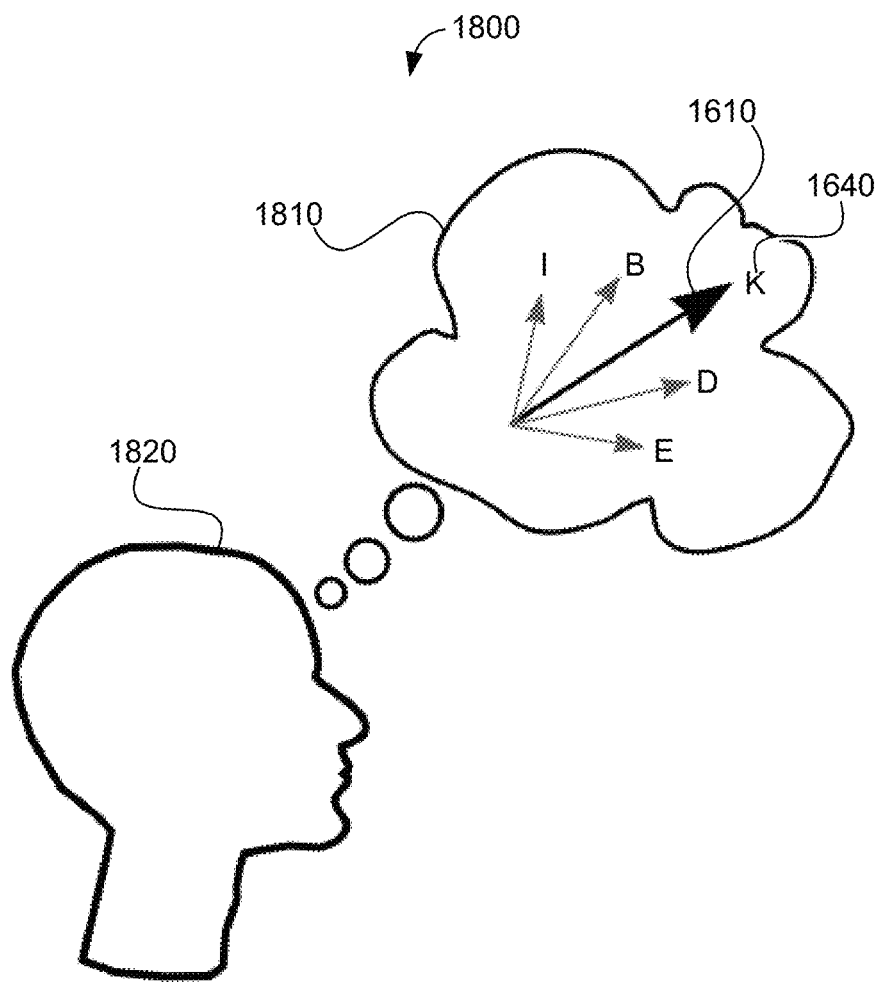
FIG. 18 is a graphic showing how a percipient directs his thoughts and volition to "steer" the output of a ThoughtPad to produce a spike or spike train in the "K" direction, which can be used to train a spiking artificial neural network.

FIG. 18 is a graphic 1800 showing how a percipient directs his thoughts and volition to "steer" the output of a ThoughtPad to produce a spike or spike train in the "K" direction, which can be used to train a spiking artificial neural network. The graphic shows how a percipient 1820 might impose his volition on ThoughtPad 1600 to cause a machine to move in the "K" direction relative to its current inertial direction. He does this by imagining in his mind 1810 arrow 1610 moving to the right so as to superimpose it onto symbol "K" 1640. Ideally, during training and/or operationally, percipient should have some real-time audio, visual, and/or tactile feedback so that he can make corrections as necessary.

Figure 19:
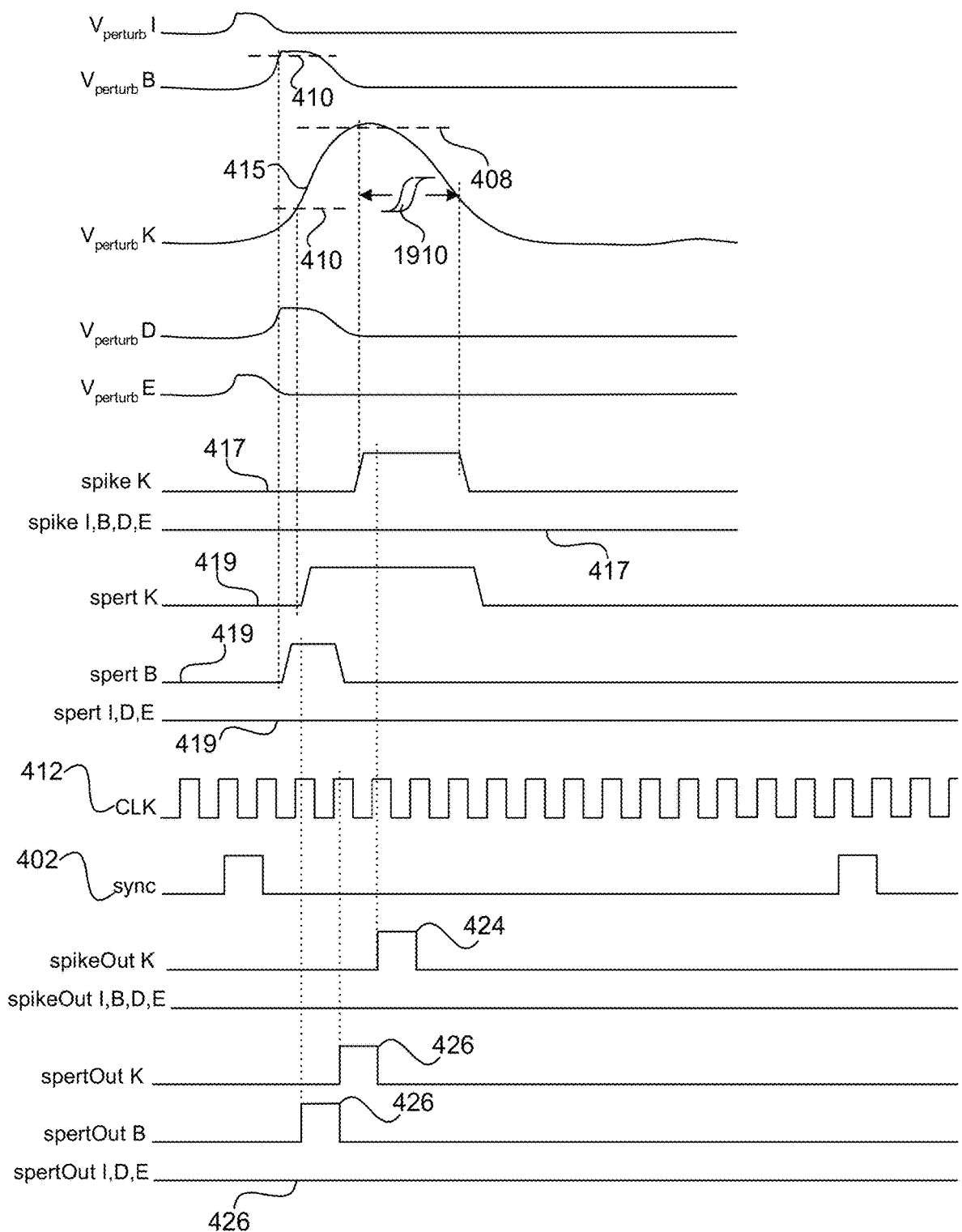
FIG. 19 is an exemplary timing diagram showing the relationship between a system clock, sync signal and exemplary outputs, both analog and digital, of a ThoughtPad in response to the percipient of FIG. 18 imposing a volition upon the ThoughtPad to steer in the "K" direction.

FIG. 19 is an exemplary timing diagram showing the relationship between a system clock, sync signal, and exemplary outputs (both analog and digital) of a ThoughtPad in response to the percipient of FIG. 18 imposing a volition upon the ThoughtPad to steer in the "K" direction. This timing diagram shows an exemplary timing relationship between various signals produced by the logic of spiker circuit 400 in response to psychotronic stimulus provided by percipient 1820 when imposing his volition upon Thought-Pad 1600 to cause a target machine to change course. The system clock CLK 412 is a free-running clock. Sync 402 synchronizes the capture of data so as to create a data frame (or spike train) 16 clocks deep, every 16 clocks in this instance. From sync 402, it can be seen that the sync pules are spaced 16 clocks apart, although different implementations may have fewer or more clocks, depending on the requirements of a given implementation.

Each instrumentation amplifier 414 (See FIG. 4) produces a buffered and amplified analog $V_{perturb}$ signal 415 reflecting the amount of current passing through its series resistor 406 (FIG. 4). If the amount of current changes, this change will be reflected in the output 415 of that amplifier 414. In the example timing diagram of FIG. 19 and FIG. 4, it can be seen that the output of the amplifier associated with the transistor labeled "B" exceeds the spert Schmitt trigger threshold voltage 410, which results in the spert pulse on the output 419 of "B's" spert Schmitt trigger, which in turn goes through a synchronous one-shot circuit 422 to produce a single spert pulse exactly one clock cycle in duration and will not fire again until the next sync pulse comes along.

As can be seen from the timing diagram, the Vperturb amplifier outputs associated with ThoughtChips labeled "I", "D", and "E" never reach the pre-programmed spert Schmitt trigger threshold 410. As a result, a spert pulse is not generated for those particular ThoughtChips during this frame/spike train. If a given ThoughtChip does not spert during a given frame, a spike will not be produced for that ThoughtChip.

Again referring to the timing diagram of FIG. 19 and to FIG. 4, notice that although "B's" output level does reach its spert Schmitt trigger threshold 410, it nonetheless does not generate a spike 417 on its respective spike output. This is because there is not enough current flowing through its respective instrumentation amplifier's series resistor 406 to yield a voltage high enough to trigger its respective "spike" Schmitt trigger 416.

As can be seen from the timing diagram, when percipient 1820 directs his volition at the ThoughtPad to move in the direction of labeled "K", current is psychotronically diverted away from one or more other ThoughtChips so as to increase the current flowing through "K's" series resistor 406 sufficiently enough to produce a voltage level that exceeds its respective spike Schmitt trigger threshold level 408.

In this instance, due to "K's" Vperturb 415 rise time, "K's" spert Schmitt trigger will fire 419 roughly one clock before its spike Schmitt trigger fires 417. As with "B", once "K's" spert Schmitt trigger fires, the spert pulse will trigger a synchronous one-shot that produces a spertOut pulse 426 exactly one clock cycle in duration and will not fire again until after the next sync pulse 402 comes along. As can be seen from the timing diagram of FIG. 19, "K" is the only ThoughtChip that produces a spikeOut pulse during this frame, while both "B" and "K" ThoughtChips produce a respective spertOut pulse 426 during this frame.

The symbol labeled 1910 indicates the Schmitt trigger has hysteresis, meaning the output will not switch back to zero until after the input drops substantially lower than the upper trigger point that originally caused the Schmitt trigger to fire. Hysteresis is a way of providing some noise immunity to help prevent false triggering on the down slope of the input.

In sum, percipient 1820 caused the production of a spike train comprising one spikeOut 424 and two spertOuts 426. "B's" spertOut occurred on the second clock after sync 402 went high. "K's" spertOut occurred on the third clock after sync 402 went high, while its spikeOut went active on the fourth clock after sync went high. This forms a spike train that can be used to identify with particularity percipient's 1820 volition. This spike train can be used as is, or it can be run through an artificial spiking neural network and used to train a machine to correctly respond to percipient's 1820 volition.

Figure 20:
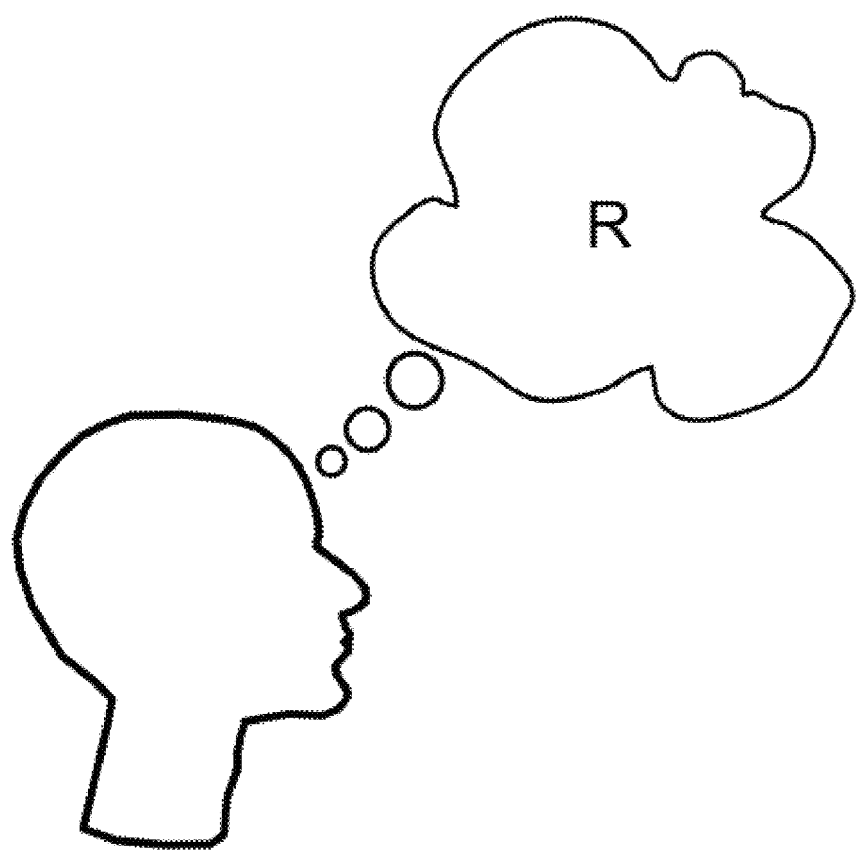
FIG. 20 is an exemplary graphic showing a percipient imposing a volition upon a ThoughtPad to spike an "R" on its output, without any directional or magnitude component to the volition.

FIG. 20 is an exemplary graphic showing a percipient imposing a volition upon a ThoughtPad or ThoughtChip to spike an "R" on its output, without any directional or magnitude component to the volition. This is essentially the same as a simple key press on a keyboard or keypad. This, of course, could be the first character of a text message or password, for example.

Figure 21:
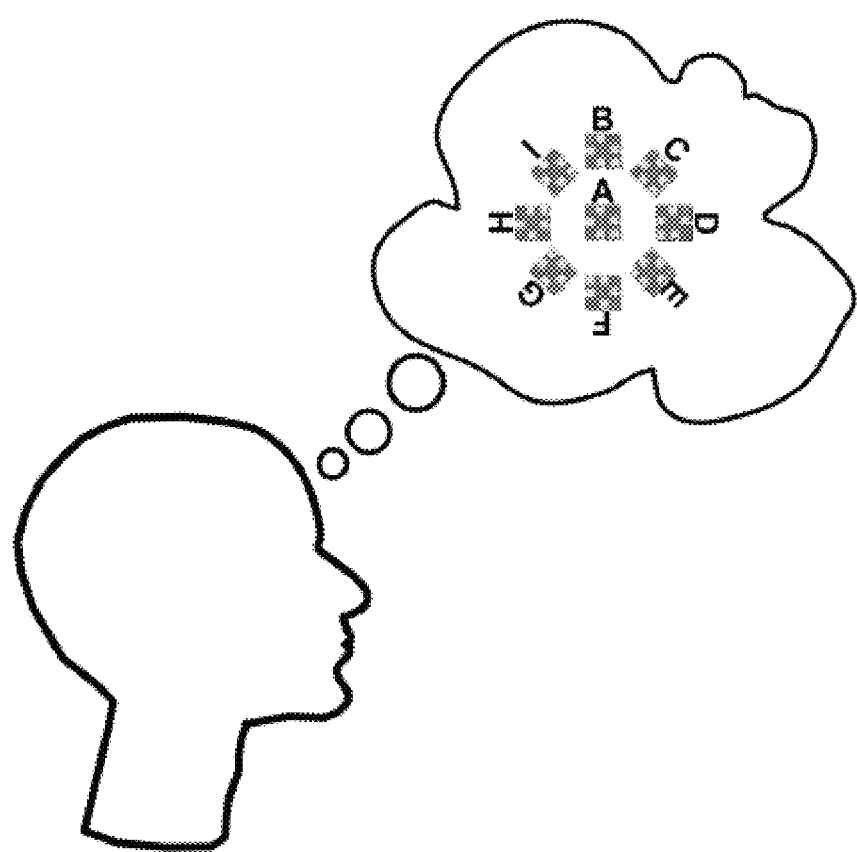
FIG. 21 is an exemplary graphic showing a percipient imposing a volition upon a ThoughtPad to simultaneously spike an "A, B, C, D, E, F, G, H, I" on its output, without any directional or magnitude component to the volition.

FIG. 21 is an exemplary graphic showing a percipient imposing a volition upon a ThoughtPad to simultaneously spike an "A, B, C, D, E, F, G, H, I" on its output, without any directional or magnitude component to the volition. The percipient directs his volition at ThoughtChips "A-I" simultaneously. Such an action may be utilized functionally, for example, like pressing CNTL-ALT-DEL on a computer keyboard as a way to reboot a computer.

Figure 22:
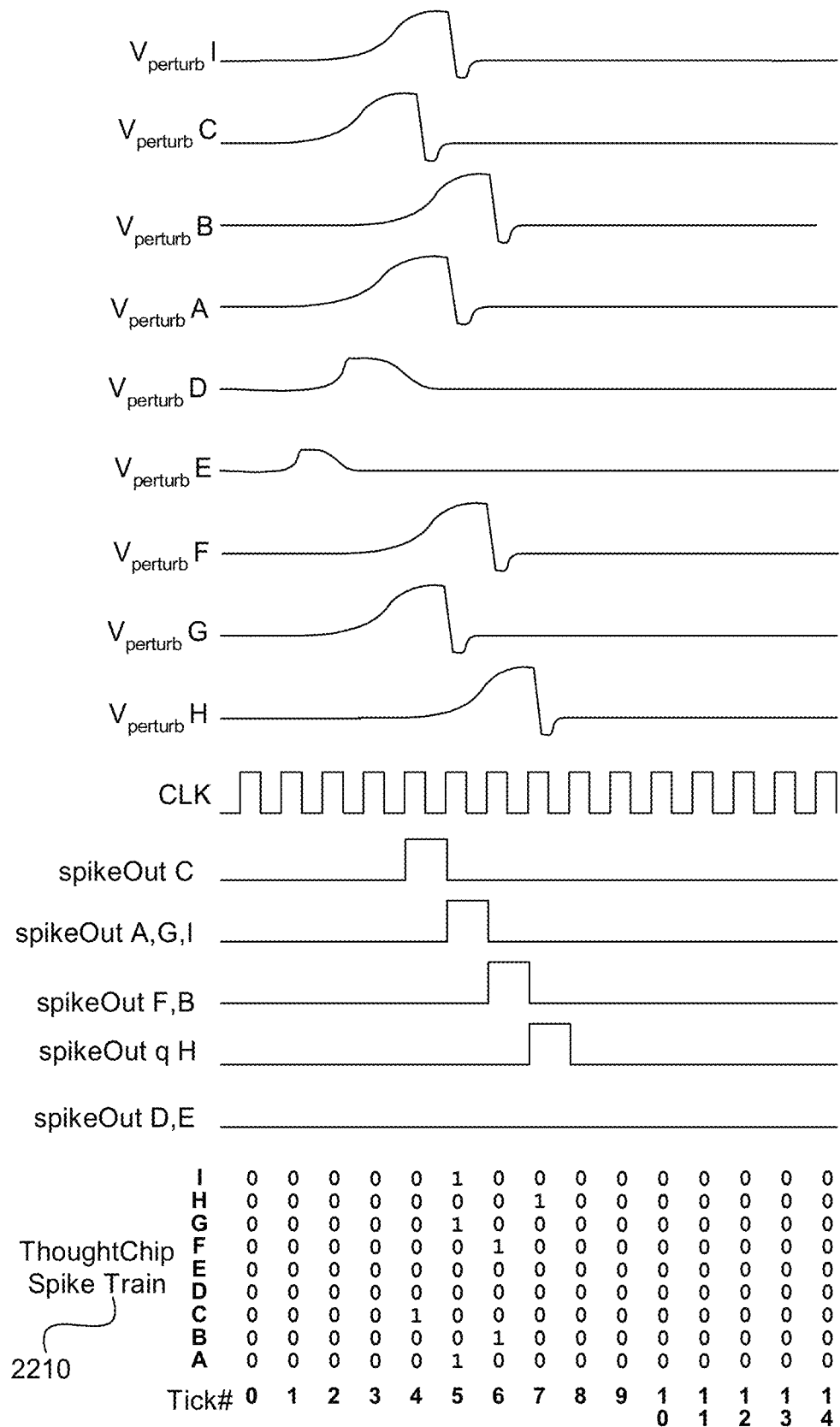
FIG. 22 is an exemplary timing diagram showing the relationship between a system clock and outputs, both analog and digital, of a ThoughtPad in response to the percipient of FIG. 21 imposing a volition up the ThoughtPad to produce a spike train on its output that then can be fed into an artificial spiking neural network.

FIG. 22 is an exemplary timing diagram showing the relationship between a system clock and outputs, both analog and digital, of a ThoughtPad in response to the percipient of FIG. 21 imposing a volition upon the ThoughtPad to produce a spike train on its output that then can be fed into an artificial spiking neural network. FIG. 22 shows the effect the action depicted in FIG. 21 had on the ThoughtChips of the targeted ThoughtPad. Observe how all but two of the ThoughtChips produced a spikeOut and how the pulses are staggered. When this spike train 2210 is fed into a properly trained artificial spiking neural network, that network will be able to deduce that pressing buttons "A-I" is what percipient really meant, especially if "D" and "E" both produced a spertOut, which is also part of the spike train fed into the spiking neural network.

Figure 23:
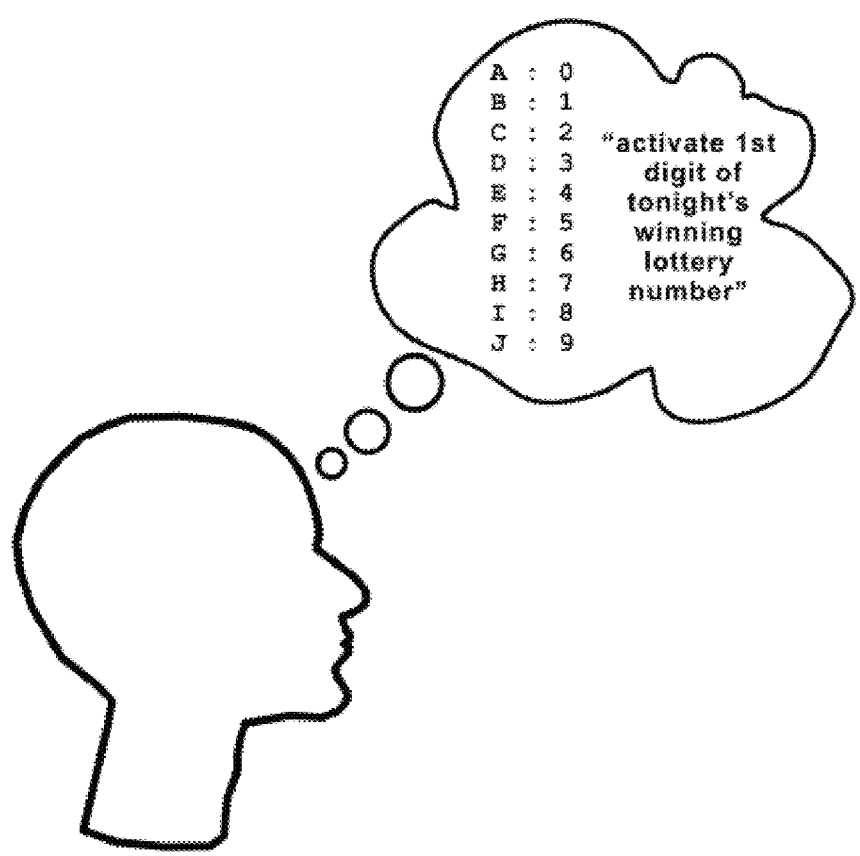
FIG. 23 is an exemplary graphic showing a percipient imposing a volition upon a ThoughtPad to produce a spike on the output of one of its ThoughtChips whose label/symbol corresponds to a single numeral associated with it by percipient, such that the emitted spike's symbol corresponds to that evenings lottery number first digit, such lottery drawing not having happened yet.

FIG. 23 is an exemplary graphic showing a percipient imposing a volition upon a ThoughtPad to produce a spike on the output of one of its ThoughtChips whose label/symbol corresponds to a single numeral associated with it by percipient. The emitted spike's symbol may correspond, for example, to the first digit of that evening's lottery number, such lottery number not having been drawn yet. This exemplary graphic illustrates just a few examples of things that can be done when a volition is directed at the ThoughtPad, wherein the percipient associates a symbol for something else. In this case, percipient is volitioning the ThoughtPad to spikeOut on ThoughtChip "A" if the first digit of that evening's winning lottery number is zero, or spikeOut on "B" if the first digit is one, and so on. Here, the percipient has no knowledge of the winning lottery number because the lottery drawing has not occurred yet. Instead, the percipient is relying on the fact that the ThoughtPad's ThoughtChips have direct access to the vacuum state, in that such information can be accessed and unfolded into information that can be output in human and/or machine-readable form.

Figure 24:
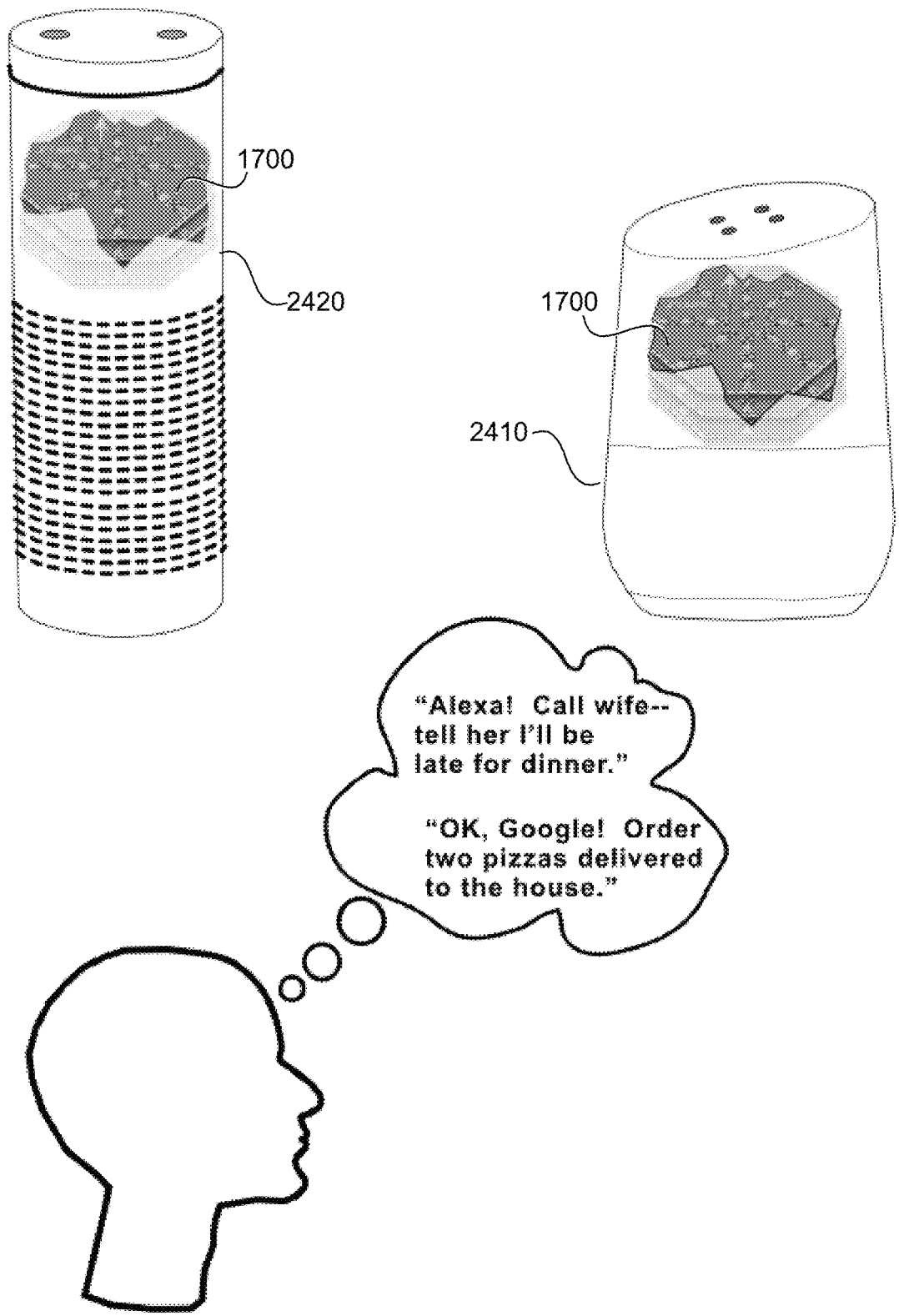
FIG. 24 is an exemplary graphic showing how existing virtual assistants can be adapted to include a ThoughtPad or ThoughtStack so they can become responsive to a percipient's volition alone.

FIG. 24 is an exemplary graphic showing how existing virtual assistants can be adapted to include a ThoughtPad or ThoughtStack so they can become responsive to a percipient's volition alone. In this example, the percipient is volitioning a first virtual assistant 2420, adapted with a ThoughtPad 1700 internal to it, to call the percipient's wife and inform her that the percipient will be late for dinner. Next, the percipient directs his volition to a second virtual assistant 2410, which also has a ThoughtPad installed internal to it, and volitions it to order two pizzas delivered to the percipient's house. It should be understood that the virtual assistants need not be in the same room or building as the percipient, in that the ThoughtPad, comprising at least in part the vacuum state information unfolder of 600 or 900, for example, obtains its information and instructions from the vacuum state and possibly ssDNA of the percipient that decorates some or all of the psychlotrons and/or bifurcated transistors included in the ThoughtPad.

Figure 25:
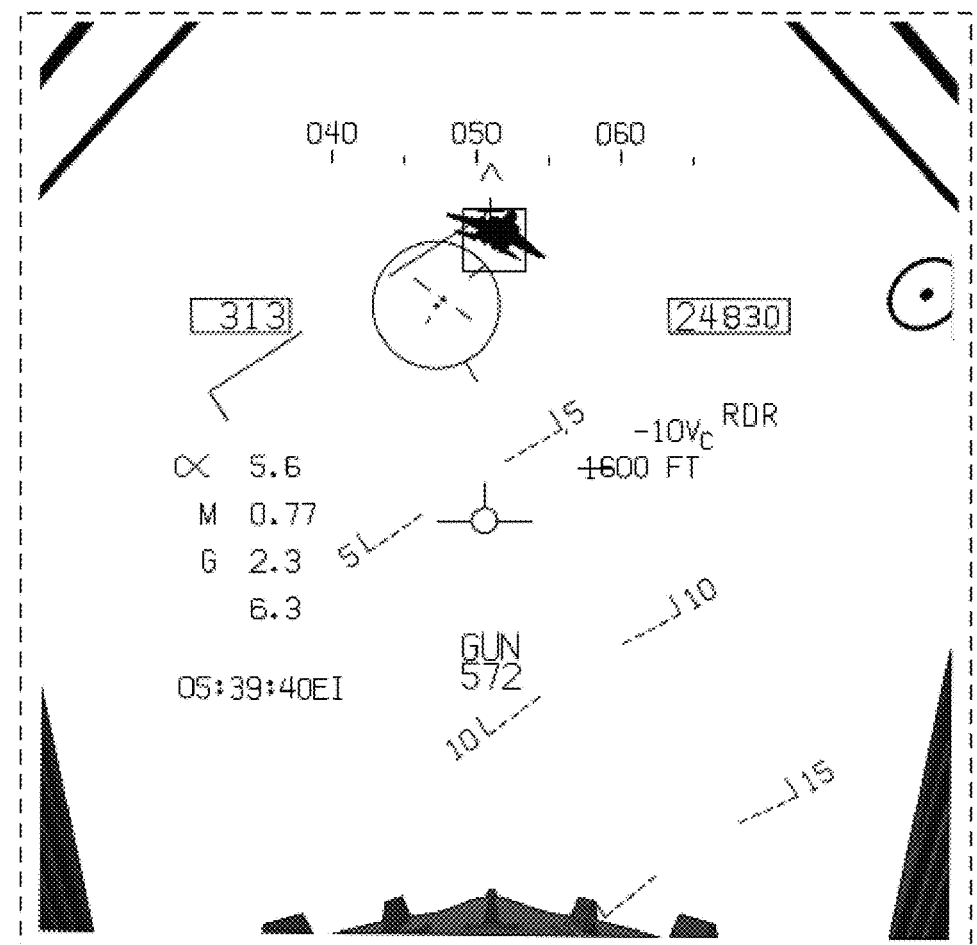
FIG. 25 is an exemplary graphic showing how weapon systems can be adapted to include a ThoughtPad or ThoughtStack so they can become responsive to a percipient's volition alone and that percipient can be remotely situated with respect to the weapon system, ThoughtPad/Stack, and/or physical war zone.
Figure 25:
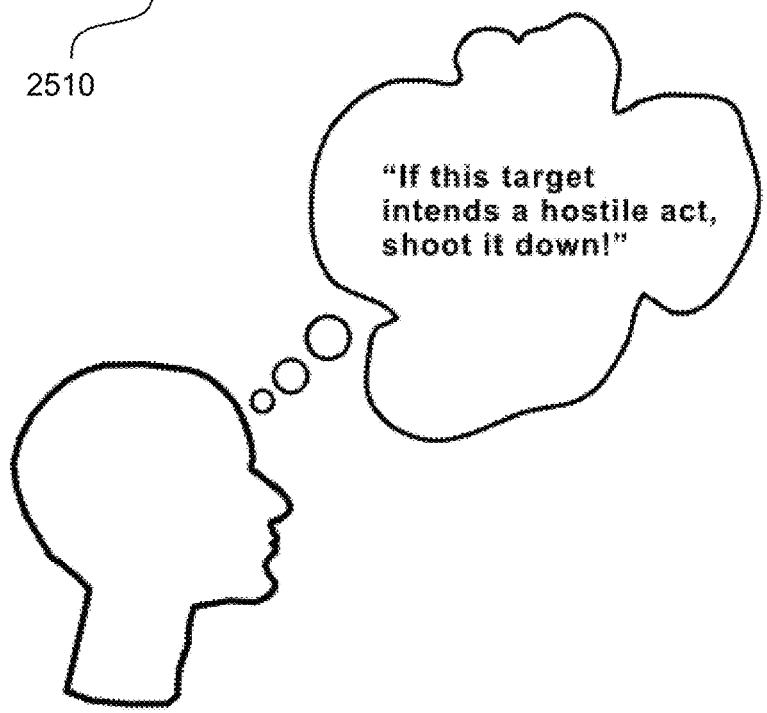

FIG. 25 is an exemplary graphic showing how weapon systems can be adapted to include a ThoughtPad or ThoughtStack so they can become responsive to a percipient's volition alone. The percipient may be remotely situated with respect to the weapon system, ThoughtPad/Stack, and/or physical war zone. In this example, a military pilot percipient is volitioning his aircraft to assess whether the potential hostile target appearing in his heads-up display (HUD) 2510 has manifested (or will manifest) hostile intentions and, if so, to shoot it down before the target carries out the hostile intention. It should be understood that the pilot percipient need not be physically located inside the cockpit of the aircraft/weapon system and may be located anywhere on or off planet in relation to the weapon system. In fact, the ThoughtPad that is having the pilot percipient's volition directed at it, need not be physically located within the percipient pilot's aircraft or even in the same room or building as pilot percipient.

HUD 2510 provides percipient with a valuable and useful feedback mechanism, not only for real-world operational missions, but also for training, in that such display, running simulations, can be used to train not only percipient pilots, but also artificial spiking neural networks processing spike trains supplied by a pilot percipient's ThoughtPad or ThoughtStack.

Figure 26:
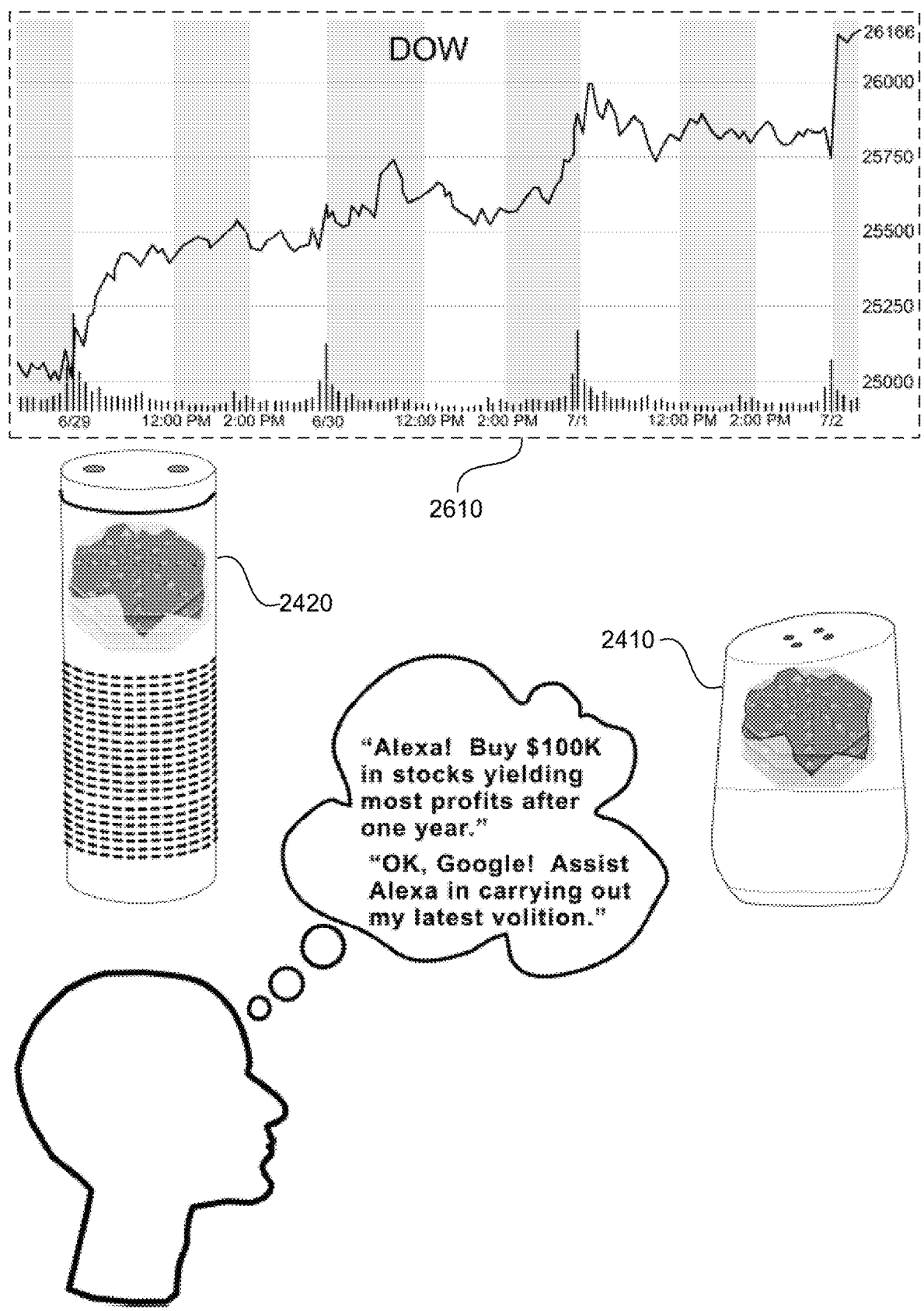
FIG. 26 is an exemplary graphic showing how the present invention can be incorporated into modern virtual assistants and employed to predict future stock market swings and make purchases accordingly to maximize profits of investors.

FIG. 26 is an exemplary graphic showing how the present invention can be incorporated into modern virtual assistants and employed to predict future stock market swings and make purchases accordingly to maximize profits of investors. In this example, percipient is volitioning the first virtual assistant 2420 to buy $100,000 in stocks that will yield the most profits (compared to all other stocks) after one year 2610. The percipient then directs his volition at the second virtual assistant 2410 to assist the first virtual assistant 2420 in carrying out the first volition. In this example, the percipient has no idea which stocks will yield the most profits after one year and is relying on the virtual assistants to make that determination. This is an example of how a percipient can get two virtual assistants to work together to carry out an ultimate volition, which is to make the most profit in the stock market 2610 after an initial investment of $100,000 and held for one year.

Figure 27:
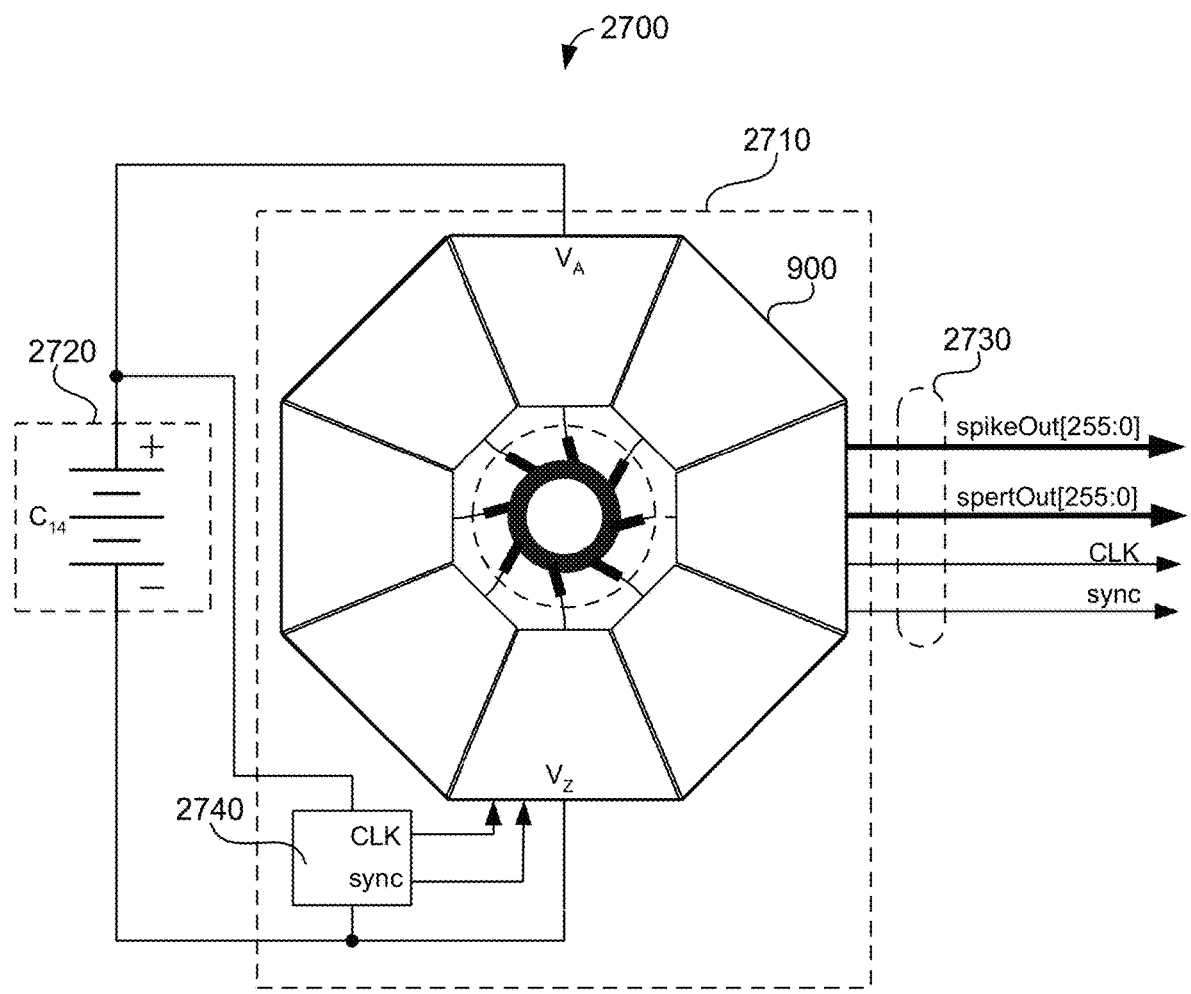
FIG. 27 is an exemplary diagram of an electrically-isolated, immortal vacuum state information unfolder that can be connected via opto-couplers to a computer, in that it includes a carbon-14 battery, which has an estimated half-life of 5000 years.

FIG. 27 is an exemplary diagram of an electrically-isolated, immortal vacuum state information unfolder 2700 that can be connected via opto-couplers to a computer, in that it includes a carbon-14 battery, which has an estimated half-life of 5,000 years. The unfolder 2700 includes a self-contained vacuum state information unfolder 2710 and a carbon-14 (radioactive diamond) battery 2720. The exemplary self-contained vacuum state information unfolder 2710 includes either a vacuum state information unfolder 600 or 900 (for example) and a built-in clock and sync generator 2740.

By optically isolating the outputs of unfolder 2710 using opto-coupler bridge 2730, the unfolder is protected from accidental electrical damage while interfacing to different systems, which get older over time and must eventually be upgraded or replaced. Power for the output drivers (photo transistors) of the bridge 2730 may be supplied by an external source when connected to it. With the addition of the clock and sync generator circuit 2740 and carbon-14 battery, the vacuum state information unfolder 2700 is completely self-contained and will continue to run even when not connected to anything. Thus, the sync output of 2740 can be looked at as a heartbeat that will beat at a steady pace for about 5,000 years, which is roughly the half-life of carbon-14.

In the drawings and specification, there have been disclosed typical preferred embodiments of the disclosure and, although specific terms are employed, they are used in a generic and descriptive sense only and not for purposes of limitation, the scope of the invention being set forth in the following claims.

What is claimed is:

1. A complex nanostructure forming a bidirectional nanostructure multiplexer, said complex nanostructure comprising:
   a circular carbon nanotorus comprising a first carbon nanotube formed into a circle thereby forming a circular carbon nanotube, the circular carbon nanotube having a plurality of apertures in a side thereof facing radially outward from a center of the nanotorus;
   a plurality of linear carbon nanotubes having first and second ends and a diameter smaller than a diameter of the circular carbon nanotube, wherein the first end of each of the plurality of linear carbon nanotubes is inserted through one of the plurality of apertures in the circular carbon nanotube, thereby forming a plurality of junctions;
   wherein one of the plurality of linear carbon nanotubes forms an axon of the bidirectional nanostructure multiplexer while the remaining linear carbon nanotubes form a plurality of dendrites of the bidirectional nanostructure multiplexer;
   voltage means for creating at least one difference in potential between the second end of the linear carbon nanotube forming the axon and at least one of the second ends of the linear carbon nanotubes forming the plurality of dendrites; and
   wherein, when at least one of the plurality of linear carbon nanotubes is of a semiconducting variety, the nanostructure further comprises gate means for forming at least one electrical field in proximity to the at least one semiconducting linear carbon nanotube, said at least one electrical field being sufficiently strong to enable current to flow through the bidirectional nanostructure multiplexer in a direction from higher potential to lower potential.

2. The complex nanostructure as recited in claim 1, wherein:
   the circular carbon nanotube forming the circular carbon nanotorus is metallic; and
   the plurality of linear carbon nanotubes forming the axion and dendrites are semiconducting.

3. The complex nanostructure as recited in claim 1, wherein the circular carbon nanotube forming the circular carbon nanotorus is decorated with a genetic material.

4. The complex nanostructure as recited in claim 1, wherein each of the plurality of linear carbon nanotubes is decorated with a genetic material.

5. A complex nanostructure forming a bidirectional nanostructure multiplexer, said complex nanostructure comprising:
   a first hollow nanotube formed into a circle thereby forming a circular hollow nanotube, the circular hollow nanotube having at least two apertures made in a side thereof facing outward from a center of the circle;
   a second hollow nanotube having a first end and a second end and having a diameter smaller than a diameter of a first of said apertures, wherein the first end of the second hollow nanotube is inserted through the first of said apertures into an interior of the circular hollow nanotube, thereby forming a first junction; and
   at least one third hollow nanotube having a first end and a second end and having a diameter smaller than a diameter of at least one second of said apertures, wherein the first end of the at least one third hollow nanotube is inserted through the at least one second of said apertures into the interior of the circular hollow nanotube, thereby forming at least one second junction;
   wherein the second hollow nanotube forms an axon of the bidirectional nanostructure multiplexer and the at least one third hollow nanotube forms at least one dendrite of the bidirectional nanostructure multiplexer;
   voltage means for creating at least one difference in potential between the second end of the second hollow nanotube forming the axon and the second end of the at least one third hollow nanotube forming the at least one dendrite; and
   wherein, when the second hollow nanotube or the at least one third hollow nanotube is of a semiconducting variety, the nanostructure further comprises gate means for forming at least one electrical field in proximity to the second hollow nanotube or the at least one third semiconducting hollow nanotube, said at least one electrical field being sufficiently strong to enable current to flow through the bidirectional nanostructure multiplexer in a direction from higher potential to lower potential.

6. The complex nanostructure as recited in claim 5, wherein the circular, second, and at least one third hollow nanotubes are hollow carbon nanotubes.

7. The complex nanostructure as recited in claim 5, wherein:
the circular hollow nanotube is a conductor; and
the second and at least one third hollow nanotubes are semiconductors.

8. The complex nanostructure as recited in claim 5, wherein the circular, second, and at least one third hollow nanotubes are conductors.

9. The complex nanostructure as recited in claim 5, wherein the circular hollow nanotube is decorated with a genetic material.

10. The complex nanostructure as recited in claim 5, wherein the circular, second, and at least one third hollow nanotubes are decorated with a genetic material.

11. The complex nanostructure as recited in claim 5, wherein the axon and any dendrite of the bidirectional nanostructure multiplexer together form a bidirectional artificial neuron.

12. A complex nanostructure forming a bidirectional nanostructure multiplexer, said complex nanostructure comprising:
a first hollow nanotube formed into a circle thereby forming a circular hollow nanotube, the circular hollow nanotube having at least two apertures made in a side thereof facing outward from a center of the circle;
a genetic material wire having a first end and a second end and having a diameter smaller than a diameter of a first of said apertures, wherein the first end of the wire is inserted through the first of said apertures into an interior of the circular hollow nanotube, thereby forming a first junction; and
at least one second hollow nanotube having a first end and a second end and having a diameter smaller than a diameter of at least one second of said apertures, wherein the first end of the at least one second hollow nanotube is inserted through the at least one second of said apertures into the interior of the circular hollow nanotube, thereby forming at least one second junction;
wherein the genetic material wire forms an axon of the bidirectional nanostructure multiplexer and the at least one second hollow nanotube forms at least one dendrite of the bidirectional nanostructure multiplexer;
voltage means for creating at least one difference in potential between the second end of the genetic material wire forming the axon and the second end of the at least one second hollow nanotube forming the at least one dendrite; and
wherein, when the at least one second hollow nanotube is of a semiconducting variety, the nanostructure further comprises gate means for forming at least one electrical field in proximity to the at least one second semiconducting hollow nanotube, said at least one electrical field being sufficiently strong to enable current to flow through the bidirectional nanostructure multiplexer in a direction from higher potential to lower potential.

13. The complex nanostructure as recited in claim 12, wherein the circular and at least one second hollow nanotubes are hollow carbon nanotubes.

14. The complex nanostructure as recited in claim 12, wherein:
the circular hollow nanotube is a conductor; and
the at least one second hollow nanotubes are semiconductors.

15. The complex nanostructure as recited in claim 12, wherein the circular and at least one second hollow nanotubes are conductors.

16. The complex nanostructure as recited in claim 12, wherein the circular hollow nanotube is decorated with a genetic material.

17. The complex nanostructure as recited in claim 12, wherein the circular and at least one second hollow nanotubes are decorated with a genetic material.

18. The complex nanostructure as recited in claim 12, wherein the axon and any dendrite of the nanostructure multiplexer together form a bidirectional artificial neuron.

19. The complex nanostructure as recited in claim 1, wherein a chirality of the circular carbon nanotube determines whether the circular carbon nanotube experiences a persistent current therein, and when there is no persistent current in the circular carbon nanotube, the nanostructure further comprises field means for providing in proximity to the circular carbon nanotube, an electric field sufficiently strong to cause the persistent current.

20. The complex nanostructure as recited in claim 5, wherein a chirality of the circular hollow nanotube determines whether the circular hollow nanotube experiences a persistent current therein, and when there is no persistent current in the circular hollow nanotube, the nanostructure further comprises field means for providing in proximity to the circular hollow nanotube, an electric field sufficiently strong to cause the persistent current.

21. The complex nanostructure as recited in claim 12, wherein a chirality of the circular hollow nanotube determines whether the circular hollow nanotube experiences a persistent current therein, and when there is no persistent current in the circular hollow nanotube, the nanostructure further comprises field means for providing in proximity to the circular hollow nanotube, an electric field sufficiently strong to cause the persistent current.

* * * * *